US012643126B2

(12) United States Patent
Bayram et al.

(10) Patent No.: US 12,643,126 B2
(45) Date of Patent: Jun. 2, 2026

(54) ELECTRICAL CROSSTALK REDUCTION FOR A CAPACITIVE MICROMACHINED ULTRASONIC TRANSDUCER ARRAY

(71) Applicant: ORTA DOGU TEKNIK UNIVERSITESI, Ankara (AR)

(72) Inventors: Baris Bayram, Ankara (AR); Berkay Karacaer, Ankara (AR)

(73) Assignee: ORTA DOGU TEKNIK UNIVERSITESI, Ankara (TR)

( * ) Notice: Subject to any disclaimer, the term of this patent is extended or adjusted under 35 U.S.C. 154(b) by 339 days.

(21) Appl. No.: 18/566,775

(22) PCT Filed: Jun. 4, 2021

(86) PCT No.: PCT/TR2021/050536
§ 371 (c)(1),
(2) Date: Dec. 4, 2023

(87) PCT Pub. No.: WO2022/255958
PCT Pub. Date: Dec. 8, 2022

(65) Prior Publication Data
US 2024/0286171 A1 Aug. 29, 2024

(51) Int. Cl.
*B06B 1/02* (2006.01)
*A61B 8/00* (2006.01)

(52) U.S. Cl.
CPC .......... *B06B 1/0292* (2013.01); *A61B 8/4488* (2013.01); *B06B 2201/76* (2013.01)

(58) Field of Classification Search
CPC . B06B 1/0292; B06B 2201/76; A61B 8/4488; H10N 39/00
(Continued)

(56) References Cited

U.S. PATENT DOCUMENTS 5,473,218 A * 12/1995 Moyer .................... H01J 3/021
313/309
6,204,595 B1 3/2001 Falabella
(Continued)

FOREIGN PATENT DOCUMENTS

EP 2697160 A2 2/2014
TR 2013/12896 A 11/2013
WO 2021118476 A1 6/2021

OTHER PUBLICATIONS

Brig RS Moorthy, Doppler ultrasound, Medical Journal Armed Forces India, 2002, pp. 1-2, vol. 58.
(Continued)

*Primary Examiner* — Jeremy A Luks
(74) *Attorney, Agent, or Firm* — Bayramoglu Law Offices LLC

(57) ABSTRACT

A novel capacitive micromachined ultrasonic transducer (CMUT) array is provided and the CMUT array employs an additional electrically-addressable conductive shield that isolates each array element individually, hence the novel array is coined as Faraday Caged CMUT array. The state of this conductive shield corresponding to each array element can be set as floating for reduced parasitic and cross-coupling capacitance or grounded for reduced electrical crosstalk. Perpetual, reliable operation in floating state without the risk of catastrophic dielectric electric field breakdown event is enabled by the self-discharging mechanism through diamond emitters featuring high field emission efficiency and acting as lightning rods in a cavity. The lightning rod structure features a movable diamond membrane, which deflects towards the diamond emitter due to electrostatic force (acting as a charge-controlled capacitive device) closing the gap to facilitate the safe intermittent discharging.

5 Claims, 33 Drawing Sheets

(58) Field of Classification Search

USPC ......................................................... 310/309

See application file for complete search history.

(56) References Cited

U.S. PATENT DOCUMENTS

| | | | |
|---|---|---|---|
| 7,274,623 B2 | 9/2007 | Bayram et al. | |
| 7,545,075 B2 * | 6/2009 | Huang .................. | B06B 1/0292 |
| | | | 367/181 |
| 7,741,686 B2 | 6/2010 | Khuri-Yakub et al. | |
| 7,745,973 B2 | 6/2010 | Bayram et al. | |
| 8,398,554 B2 | 3/2013 | Degertekin | |
| 8,421,170 B2 | 4/2013 | Bayram | |
| 8,973,250 B2 * | 3/2015 | Jahnes ................. | B81C 1/0015 |
| | | | 29/609.1 |
| 9,375,850 B2 | 6/2016 | Hajati | |
| 2005/0200241 A1 * | 9/2005 | Degertekin ........... | B06B 1/0292 |
| | | | 310/334 |
| 2005/0234342 A1 | 10/2005 | Bayram et al. | |
| 2008/0259725 A1 | 10/2008 | Bayram et al. | |
| 2010/0201222 A1 * | 8/2010 | Adachi ................ | A61B 8/4483 |
| | | | 310/317 |
| 2010/0249605 A1 | 9/2010 | Degertekin | |
| 2012/0074509 A1 | 3/2012 | Berg | |
| 2012/0187508 A1 * | 7/2012 | Adler .................... | B06B 1/0292 |
| | | | 438/51 |
| 2012/0256517 A1 * | 10/2012 | Bayram ................ | B06B 1/0292 |
| | | | 310/300 |
| 2014/0219063 A1 | 8/2014 | Hajati | |
| 2018/0116632 A1 * | 5/2018 | Yoo .................... | G01N 29/2437 |

OTHER PUBLICATIONS

Rosa M.S. Sigrist, et al., Ultrasound Elastography: Review of Techniques and Clinical Applications, Theranostics, 2017, pp. 1303-1329, vol. 7, No. 5.

Pedo Santos, et al., Natural Shear Wave Imaging in the Human Heart: Normal Values, Feasibility, and Reproducibility, IEEE Transactions on Ultrasonics, Ferroelectrics, and Frequency Control, 2019, pp. 442-452, vol. 66, No. 3.

Mickael Tanter, Ultrafast Imaging in Biomedical Ultrasound, IEEE Transactions on Ultrasonics, Ferroelectrics, and Frequency Control, 2014, pp. 102-119, vol. 61, No. 1.

Jemma Brown, et al., Investigation of Microbubble Detection Methods for Super-Resolution Imaging of Microvasculature, IEEE Transactions on Ultrasonics, Ferroelectrics, and Frequency Control, 2019, pp. 676-691, vol. 66, No. 4.

K. Christensen-Jeffries, et al., Super-resolution ultrasound imaging, Ultrasound Med Biol., 2020, pp. 865-891, vol. 46.

Xuejun Qian, et al., In vivo Visualization of Eye Vasculature Using Super-resolution Ultrasound Microvessel Imaging, IEEE Transactions on Biomedical Engineering, 2020, pp. 1-11, vol. 67, No. 10.

D. Buonsenso, et al., Point-of-Care Lung Ultrasound findings in novel coronavirus disease-19 pnemoniae: a case report and potential applications during COVID-19 outbreak, European Review for Medical and Pharmacological Sciences, 2020, pp. 2776-2780.

Pei-Yu Chen, et al., Characterization of Hand Tendons Through High Frequency Ultrasound Elastography, IEEE Transactions on Ultrasonics, Ferroelectrics, and Frequency Control, 2020, pp. 37-48, vol. 67, No. 1.

S.P. Arjunan, et al., A Review of Ultrasound Imaging Techniques for the Detection of Down Syndrome, IRBM, 2020, pp. 115-123, vol. 41.

Alireza Nabavizadeh, et al., Noninvasive Young's modulus visualization of fibrosis progression and delineation of pancreatic ductal adenocarcinoma (PDAC) tumors using Harmonic Motion Elastography (HME) in vivo, Theranostics, 2020, pp. 4614-4626, vol. 10.

Claire Rabut, et al., 4D functional ultrasound imaging of whole-brain activity in rodents, Nature Methods, 2019, pp. 994-997, vol. 16.

A. Novell, et al., A new safety index based on intrapulse monitoring of ultra-harmonic cavitation during ultrasound-induced blood-brain barrier opening procedures, Scientific Reports, 2020, vol. 10.

Yuhang Tian, et al., New Aspects of Ultrasound-Mediated Targeted Delivery and Therapy for Cancer, International Journal of Nanomedicine, 2020, pp. 401-418, vol. 15.

Matthew I. Haller, et al., A Surface Micromachined Electrostatic Ultrasonic Air Transducer, IEEE Ultrasonics Symposium, 1994, pp. 1241-1244.

Peter-Christian Eccardt, et al., Surface micromachined ultrasound transducers in CMOS technology, IEEE Ultrasonics Symposium, 1996, pp. 959-962.

Baris Bayram, et al., A new regime for operating capacitive micromachined ultrasonic transducers, IEEE Transactions on Ultra-sonics, Ferroelectrics, and Frequency Control, 2003, pp. 1184-1190, vol. 50, No. 9.

Baris Bayram, et al., Capacitive Micromachined Ultrasonic Transducer Design for High Power Transmission, IEEE Transactions on Ultrasonics, Ferroelectrics, and Frequency Control, 2005, pp. 326-339, vol. 52, No. 2.

Kevin Brenner, et al., Advances in Capacitive Micromachined Ultrasonic Transducers, Micromachines, 2019, vol. 10.

Rob Van Schaijk, CMUT and PMUT: New Technology Platform for Medical Ultrasound, Philips Innovation Services MEMS&Micro Devices Report, 2018.

Akifumi Sako, et al., Development of Ultrasonic Transducer 'Mappie' with cMUT Technology, Medix, 2009, pp. 31-34, vol. 51.

Amirabbas Pirouz, et al., An Analysis Method for Capacitive Micromachined Ultrasound Transducer (CMUT) Energy Conversion During Large Signal Operation, Sensors, 2019, vol. 19.

Goksen G. Yaralioglu, et al., Calculation and Measurement of Electromechanical Coupling Coefficient of Capacitive Micromachined Ultrasonic Transducers, IEEE Transactions on Ultrasonics, Ferroelectrics, and Frequency Control, 2003, 449-456, vol. 50.

Baris Bayram, et al., Finite Element Modeling and Experimental Characterization of Crosstalk in 1-D CMUT Arrays, IEEE Transactions on Ultrasonics, Ferroelectrics, and Frequency Control, 2007, pp. 418-430, vol. 54, No. 2.

Alex Sampaleanu, et al., Top-Orthogonal-to-Bottom-Electrode (TOBE) CMUT Arrays for 3-D Ultrasound Imaging, IEEE Transactions on Ultrasonics, Ferroelectrics, and Frequency Control, 2014, pp. 266-276, vol. 61, No. 2.

A. Buhrdorf, et al., Fabrication and characterization of a new capacitive micromachined ullrasonic transducer (cMUT) using polysilicon as membrane and sacrificial layer material, IEEE Ultrasonics Symposium, 2003, pp. 1951-1953.

Xuefeng Zhuang, et al., Through-Wafer Trench-Isolated Electrical Interconnects for CMUT Arrays, IEEE Ultrasonics Symposium, 2005, pp. 475-478, vol. 1.

Xuefeng Zhuang, et al., Interconnection and Packaging for 2D Capacitive Micromachined UltrasonicTransducer Arrays Based on Through-Wafer Trench Isolation, 19th IEEE International Conference on Micro Electro Mechanical Systems, 2006, pp. 270-273.

Xuefeng Zhuang, et al., Integration of trench-isolated through-wafer interconnects with 2d capacitive micromachined ultrasonic transducer arrays, Sensors and Actuators A, 2007, pp. 221-229, vol. 138.

Xuefeng Zhuang, et al., Trench-Isolated CMUT Arrays with a Supporting Frame, IEEE Ultrasonics Symposium, 2006, pp. 1955-1958.

Xuefeng Zhuang, et al., Trench-Isolated CMUT Arrays with a Supporting Frame: Characterization and Imaging Results, IEEE Ultrasonics Symposium Proceedings, 2007, pp. 507-510.

Xuefeng Zhuang, et al., Wafer-Bonded 2-D CMUT Arrays Incorporating Through-Wafer Trench-Isolated Interconnects with a Supporting Frame, IEEE Transactions on Ultrasonics, Ferroelectrics, and Frequency Control, 2009, pp. 182-192, vol. 56, No. 1.

Xuefeng Zhuang, et al., Fabrication of Flexible Transducer Arrays With Through-Wafer Electrical Interconnects Based on Trench Refilling With PDMS, Journal of Microelectromechanical Systems, 2008, pp. 446-452, vol. 17, No. 2.

Peiyu Zhang, et al., Double-SOI Wafer-Bonded CMUTs With Improved Electrical Safety and Minimal Roughness of Dielectric

(56)           References Cited

OTHER PUBLICATIONS and Electrode Surfaces, Journal of Microelectromechanical Systems, 2012, pp. 668-680, vol. 21, No. 3.

Byung Chul Lee, et al., Fabrication of CMUTs with Substrate-embedded Springs, Joint UFFC, EFTF and PFM Symposium, 2013, pp. 1733-1736.

Rasim O. Guldiken, Dual-Electrode Capacitive Micromachined Ultrasonic Transducers for Medical Ultrasound Applications,Doctoral dissertation, Georgia Institute of Technology, 2008.

Ryan K. W. Chee, et al., Top Orthogonal to Bottom Electrode (TOBE) 2-D CMUT Arrays for 3-D Photoacoustic Imaging, IEEE Transactions on Ultrasonics, Ferroelectrics, and Frequency Control, 2014, pp. 1393-1395, vol. 61, No. 8.

James C. M. Hwang, Reliability of Electrostatically Actuated RF MEMS Switches, IEEE International Workshop on Radio-Frequency Integration Technology, 2007, pp. 168-171.

Oleg A. Ivanov, et al., Emission properties of undoped and boron-doped nanocrystalline diamond films coated silicon carbide field emitter arrays, Journal of Vacuum Science & Techology B, Nanotechnology and Microelectronics: Materials, Processing, Measurement, and Phenomena, 2018, vol. 36.

Filippo Giubileo, et al., Field Emission from Carbon Nanostructures, Applied Sciences, 2018, pp. 1-21, vol. 8.

Kamatchi Jothiramalingam Sankaran, et al., Boron-Doped Nanocrystalline Diamond-Carbon Nanospike Hybrid Electron Emission Source, ACS Applied Materials & Interfaces, 2019, pp. 48612-48623, vol. 11.

X. Jiang, et al., Ultrahigh boron doping of nanocrystalline diamond films and their electron field emission characteristics, Journal of Applied Physics, 2002, pp. 2880-2883, vol. 92, No. 5.

V. T Srikar, et al., Materials Selection in Micromechanical Design: An Application of the Ashby Approach, Journal of Microelectromechanical Systems, 2003, pp. 3-10, vol. 12, No. 1.

P. Ashcheulov, et al., Conductivity of boron-doped polycrystalline diamond films: influence of specific boron defects, The European Physical Journal B, 2013, pp. 1-9, vol. 86.

Baris Bayram, et al., Plasma-activated direct bonding of diamond-on-insulator wafers to thermal oxide grown silicon wafers, Diamond & Related Materials, 2010, pp. 1431-1435, vol. 19.

Baris Bayram, et al., Microfabrication of vacuum-sealed cavities with nanocrystalline and ultrananocrystalline diamond membranes and their characteristics, Diamond & Related Materials, 2011, pp. 1149-1154, vol. 20.

Baris Bayram, Fabrication of SiO2-stacked diamond membranes and their characteristics for microelectromechanical applications, Diamond & Related Materials, 2011, pp. 459-463, vol. 20.

Baris Bayram, Diamond-based capacitive micromachined ultrasonic transducers, Diamond & Related Materials, 2012, pp. 6-11, vol. 22.

Ahmet Murat Cetin, et al., Diamond-based Capacitive Micromachined Ultrasonic Transducers in Immersion, IEEE Transactions on Ultrasonics, Ferroelectrics, and Frequency Control, 2013, pp. 414-420, vol. 60, No. 2.

Uryan Isik Can, et al., Plasma-activated direct bonding of patterned silicon-on-insulator wafers to diamond-coated wafers under vacuum, Diamond & Related Materials, 2014, pp. 53-57, vol. 47.

* cited by examiner

Metal

Diamond NCD

Doped PolySilicon

HTO

LTO

Thermal Oxide

Silicon Crystal

ELECTRICAL CROSSTALK REDUCTION FOR A CAPACITIVE MICROMACHINED ULTRASONIC TRANSDUCER ARRAY

CROSS-REFERENCE TO THE RELATED APPLICATIONS

This application is the national phase entry of International Application No. PCT/TR2021/050536, filed on Jun. 4, 2021, the entire contents of which are incorporated herein by reference.

TECHNICAL FIELD

This invention relates to capacitive micromachined ultrasonic transducers (CMUT) that feature electrical crosstalk reduction between the array elements via an additional conductive shield isolating each array element individually. These electrically-addressable conductive shields can maintain perpetual, reliable operation in floating state without the risk of catastrophic dielectric breakdown event thanks to the self-discharging mechanism through diamond emitters acting as lightning rods in a cavity.

BACKGROUND

Medical ultrasound (1-50 MHz) has applications in imaging (e.g. fetal sonogram), therapeutics (e.g. kidney stone ablation), and detection (e.g. brain hemorrhage). Today, medical ultrasound is not only a standalone technology worth of >$7B but also an integral part of other emerging (e.g. photoacoustic) medical applications using ultrasound techniques such as continuous or pulsed wave Doppler (color, power and spectral) [1], shear wave elastography (point, 1D and 2D) [2, 3], contrast-enhanced ultrafast and super resolution ultrasound (microbubbles for blood and neurovascular imaging) [4-7]. Medical ultrasound is expected to grow 23% annually in the next five years. Diagnostic imaging used for detection of anomaly in lungs [8], characterization of hand tendons [9], determination of Down Syndrome [10], visualization of fibrosis in pancreatic ductal adenocarcinoma [11], functional neuroimaging and therapy used for blood-brain barrier opening procedures [13], cancer treatment are only a few of the advanced medical ultrasound applications to present the immense potential of ultrasound for public health and well-being.

All these current and emerging medical ultrasound technologies rely on discrete devices called ultrasonic transducers. A capacitive micromachined ultrasonic transducer (CMUT) is a microelectromechanical system (MEMS) based device that converts electrical energy to mechanical energy and vice versa [15, 16]. Compared to traditional ultrasound based on piezoelectric technology, CMUTs offer CMOS compatible wafer level microfabrication and wide operating temperature range [17-19]. CMUTs are being developed by research institutions (Stanford, Fraunhofer, VTT, Leti, Imec), foundries (Philips, Global Foundries, Micralyne, Silex) and companies (Hitachi, Siemens, General Electric, Samsung, Vermon, Kolo, Butterfly) due to their fascinating potential in wide range of areas such as ultrasonic imaging, therapy, industrial cleaning, photoacoustic imaging, and air-coupled ultrasonic applications. CMUT-based medical ultrasound units were produced by Hitachi (2008), Butterfly (2017), Kolo (2018) and Vermon (2019) [20, 21]. Commercial production of CMUTs for medical use demonstrate the potential of the capacitive devices against mature piezoelectric counterparts.

The working principle of a CMUT is based on the electrostatic force between two electrodes, top and bottom electrodes, that are separated by a vacuum sealed cavity between them. When a DC voltage is applied between these electrodes, the moveable top electrode moves towards the fixed bottom electrode due to the electrostatic force. In the transmit operation of a CMUT, in addition to the DC bias, an AC signal is applied between the electrodes, and vibration of the top electrode generates the acoustic wave. In the receive operation, the incoming acoustic wave moves the top electrode, and the change in the capacitance between the electrodes is sensed via a transimpedance amplifier, which generates the voltage signal in response. In the immersion operation of the CMUT arrays, the top electrodes are mostly grounded for safety issues. Thus, the DC bias and the AC signal are applied to the bottom electrodes. Conventional, collapse, resistive-collapse and collapse-snapback modes of the CMUT can be used for transmit and receive operations [17-18, 22-23].

The active capacitance of a CMUT cell is the capacitance between the bottom electrode and the moveable region of the top electrode. However, the total capacitance between the bottom and the top electrodes is more than the active capacitance of the CMUT cell because of the parallel parasitic capacitance. In the transmit operation, the parasitic capacitance is of little concern, however, the parasitic capacitance drastically reduces the receiving sensitivity and the coupling efficiency of a CMUT [24, 25].

Crosstalk is the coupling of energy between the elements of a CMUT array. There are two main types of crosstalk, acoustical and electrical, in CMUT arrays. Acoustic crosstalk is the crosstalk mechanism caused by the mechanical wave propagation affecting the other element through the substrate and the immersed medium, whereas electrical crosstalk is the crosstalk mechanism caused by the coupling of the electromagnetic wave from one array element to another [26]. Since the applied voltage is much higher in transmit operation compared to the detected voltage in receiving operation, the electrical crosstalk is much more effective in transmit operation of the CMUT array. The electrical crosstalk increases the noise in the system, and it degrades the focusing and imaging performance.

Bayram et. al. proposed a new microfabrication method to reduce acoustic crosstalk by 12 dB via introducing a passive membrane in the separation region between neighboring array elements [27].

For top-orthogonal-to-bottom-electrode (TOBE) and interleaved CMUT arrays, the cross-coupling capacitance and the electrical crosstalk are significantly increased [28]. In the literature there are several publications and patents related to the electrical crosstalk reduction in CMUTs [28-44].

Burhdorf et al. developed a new microfabrication method for CMUT arrays with polysilicon membrane [29]. In the proposed method, both the bottom and the top electrodes of each array element are separated from the corresponding electrodes of the other elements to provide electrical isolation.

Zhuang et al. reported a microfabrication method for trench isolated CMUT arrays [30-32]. In this method, the electrical connection of CMUT elements, where elements are constructed on the device layer of the silicon-on-insulator (SOI) wafer, is provided from the backside of the handle wafer. Deep trenches throughout the handle wafer are etched to construct hot electrodes, which are the electrodes that carry signals from the backside of the handle wafer to the CMUT array. Thus, by those deep trenches between the hot electrodes, electrical isolation between CMUT elements is provided. Electrical crosstalk and electrical cross-coupling capacitance of the microfabricated CMUT arrays are measured and reported as −53 dB and 29 fF, respectively [30]. Moreover, the change in the electrical cross-coupling capacitance with the trench width is examined, and it is observed that electrical cross-coupling capacitance is inversely proportional to trench width. There is no conductive shield around the array elements in the reported work.

Compared to trench isolated CMUT array, further reduction in the electrical crosstalk was reported by Zhuang et al., where they developed a microfabrication method for trench isolated CMUT arrays with supporting frame [33-36]. In the suggested microfabrication method, in addition to the hot electrodes (the electrodes that carry signals from the backside of the handle wafer to the CMUT array), a continuous supporting frame is constructed by the deep trenches etched in the handle wafer. Similar to the hot electrodes, the supporting frame is also conductive. Also, between neighboring hot electrodes there is a conductive supporting frame. This conductive supporting frame that covers hot electrodes is continuous throughout the structure and is grounded. In this design, the electrical crosstalk between neighboring elements is found as −65 dB [33]. An improvement of 12 dB (from −53 dB to −65 dB) in the element to element electrical crosstalk has been explained as a result of the inherent electrical shielding provided by the conductive silicon supporting frame. On the other hand, a grounded supporting frame increases parasitic capacitance, which degrades CMUT performance. It is stated that the parasitic capacitance increases with the supporting frame width.

Zhuang et al. proposed another microfabrication method for providing mechanical support in trench isolated CMUT arrays. [37]. This microfabrication is similar to one developed for trench isolated CMUT arrays. However, different from the previous trench isolated CMUT array microfabrication, in the proposed microfabrication, an organic, flexible, and dielectric material (PDMS) was filled into deep trenches to provide structural integrity to silicon wafers. Since PDMS is a dielectric material, electrical isolation between CMUT arrays is provided. No measurement on electrical crosstalk or cross-coupling capacitance is given.

Zhang et al. developed another method to define individually addressable electrodes and finer isolation of electrodes from the environment for safety issues [38]. The surface roughness of the electrodes and dielectrics is minimized to reduce the surface charging. Since the surface charging of electrodes and dielectrics is minimized, and electrodes are fully covered in a dielectric, and finer isolation of electrodes is provided. However, no comment about electrical crosstalk or cross-coupling capacitance is given.

Berg et al. developed a microfabrication method for CMUT array wherein the membranes of individual elements are grounded, and electrical signal to elements are provided from the backside of the substrate utilizing conductive vias [39]. Thermally grown silicon dioxide is used to isolate the vias from each other. Also, in the structure, there are trenches of silicon dioxide for isolation between the array elements. Thus, the CMUT elements and the conductive vias of the CMUT elements are electrically isolated from each other. No measurement about electrical crosstalk or cross-coupling capacitance is given.

Lee et al. proposed a novel microfabrication process flow for post-CMUT [40]. Post-CMUT technology is similar to CMUT technology. However, additionally in the post-CMUT technology there are substrate-embedded springs in the structure. In post-CMUT technology, a grounded conductive frame electrode is placed between each array element, which reduces the electrical crosstalk. However, this grounded conductive shield is shared between two neighboring elements and increases the parasitic capacitance. No measurement about electrical crosstalk, parasitic capacitance, and cross-coupling capacitance is given.

Degertekin proposed a new microfabrication method for harmonic CMUT. In the proposed fabrication, there are three electrodes for each CMUT array element [41,42]. Two of the electrodes are embedded in the membrane, and the remaining electrode is the bottom electrode. The electrodes on the membrane are named as central and side electrodes due to their positions on the membrane respectively. Since the membrane is a dielectric material, the central and side electrodes are electrically isolated. The DC bias is applied between the central and bottom electrodes whereas the transmit and receive operation is performed between side and bottom electrodes. The parasitic capacitance and electrical crosstalk between the electrodes of the same CMUT array element are examined.

Sampleanu et al. proposed a novel imaging scheme for 3-D imaging with TOBE CMUT array [28]. In the proposed imaging scheme, a bias voltage is given from the selected row, whereas transmit and receive is realized from the selected columns. The electrical crosstalk of the proposed imaging scheme is compared with the electrical crosstalk of the existing imaging scheme for 3-D imaging with TOBE CMUT arrays. The average electrical crosstalk of the proposed and existing imaging scheme is found out to be −29 dB and −12.5 dB, respectively.

Chee et al. proposed modulation-encoded TOBE CMUT [43]. In this proposed method, the receiving signal was modulated with higher frequencies. It was observed that due to high frequency operation, electrical crosstalk was increased. A solution to implement isolation amplifiers between each intersecting row and column of TOBE CMUT array was suggested to reduce the electrical crosstalk. No measurement about electrical crosstalk or cross-coupling capacitance is given.

Hajati et al. proposed a new microfabrication technique for micromachined ultrasonic transducer devices with metal to semiconductor contact to reduce the electrical crosstalk [44]. In the proposed microfabrication, electrical crosstalk is reduced through grounding of the device layer of the SOI wafer over which the arrays are constructed. Metal to semiconductor contact is formed in the grounded device layer, which helps to suppress the electrical crosstalk due to forming ohmic contact that would have a contact resistance that is lower than the impedance of the parasitic capacitance. The working principle of the micromachined ultrasonic device is based on the piezoelectric instead of capacitive. The grounded device layer is common for neighboring CMUT array elements, and there is no individual conductive shield for each CMUT array element.

SUMMARY

A new electrical crosstalk reduction in CMUT arrays is presented in this document. Our invention relates to electrical crosstalk, parasitic and cross-coupling capacitance reduction based on electrically-addressable conductive shield that feature discharging in the floating state through diamond emitters acting as lightning rods in a cavity.

This invention includes an individual Faraday cage (conductive shield) and an individual third terminal for each CMUT array element to provide control over the state of the Faraday cage: grounded (GND) or floating (FLT). The Faraday cage is placed under the bottom electrode. In the proposed operation method, during the transmit operation, the Faraday cage is grounded whereas in the receive operation the Faraday cage is floating. In the literature, there is no prior art that includes an individual floating conductive shield (Faraday cage), which can be controlled by a third electrode, for each CMUT array element.

Floating conductive shields are not preferred in the structures because of the famous phenomenon called as "dielectric breakdown" [45]. A floating conductor (Faraday cage) embedded in a dielectric under a high voltage electrode (bottom electrode of the CMUT) might accumulate charges due to leakage currents in time. Once the electric field inside the dielectric caused by the gradual accumulation of the charges in the floating conductor exceeds the breakdown electric field of the dielectric, the notwithstanding dielectric might discharge through the dielectric. Afterwards, the dielectric would not be able to operate properly anymore following the destructive dielectric breakdown event. Floating conductors in microstructures are not preferred due to these events. Because the charge accumulation in the structure due to the leakage current might rise into self-destructive breakdown electric field levels for the floating conductors embedded in dielectric medium. These effects of a floating conductor limit the high voltage operation and the lifetime of the device. Thus, a safe discharging path of the floating Faraday cage is required.

In this invention, floating operation of the Faraday cage for each CMUT array element, based on a safe discharging path through diamond emitters in a cavity, is presented for the first time in the literature Diamond emitters, having very low turn-on field value (<20 V/μm [46]), are utilized as lightning rods (apex diameter <50 nm) to eliminate the accumulated excess charges on the floating Faraday cage throughout the receiving operation of the CMUT array element. Therefore, floating Faraday cage use in CMUT arrays is enabled reliably, overcoming the obstacles due to dielectric breakdown caused by charge accumulation in the floating conductors.

The field emission efficiency, which is a critical factor for an emitter of a lightning rod structure, is determined by factors such as the surface work function, the height, and sharpness of the emitting tips, the conductivity of the emitter, and resistance of the emitter-substrate interface [47]. An ideal field emitter should have a low work function, high enhancement factor, good electrical conductivity, and be stable at high emission current density where according to given properties, diamond is an excellent material for a field electron emitter [48]. Compared to metals and semiconductors, carbon nanostructures such as carbon nanotubes, carbon nanosheets, nanodiamonds, and graphene are unique and very special material that show enhanced field electron emission characteristics and are perfect as a field electron emission material [49]. Both undoped and heavily doped nanocrystalline diamond films feature high emission current and low turn-on voltage. The grain size can be adjusted to control the turn-on field value of a nanocrystalline diamond [50]. Thus, boron doped diamond pillars with a diameter less than 50 nm on top of the Faraday cage will safely discharge to the ground before the charge on the Faraday cage reaches the critical limit of dielectric breakdown field strength during the floating state.

Diamond is a semiconductor material with extreme mechanical properties that make it an attractive material for MEMS. It is one of the materials with a very high Young's modulus to density ratio, which is beneficial in MEMS since this ratio increases the probability of obtaining quasistatic mechanical response that improves the signal-to-noise ratio (SNR) of the MEMS device [51]. The electrical properties of diamond are also very interesting. The resistivity of diamond films can be controlled for a very large range with Boron (p-type) and Phosphorus (n-type) doping [52]. Furthermore, among the other semiconductors, diamond films are advantageous in terms of high operation frequency, high output power, high thermal conductivity, and thus less heating. Also, diamond is an inert material used in a MEMS device without being oxidized over the years. Another advantage of the diamond is being biocompatible so that it is available to be used in medical devices. Bayram et al., microfabricated diamond membrane CMUT array using wafer bonding technique [53-61].

Another aspect of the invention is the microfabrication method of a diamond membrane CMUT array with individual Faraday cage and lightning rod structure based on the diamond emitters. The proposed Faraday Caged CMUT array microfabrication is based on the sacrificial etching technique. The microfabrication is realized on an SOI wafer. SOI wafer includes the highly doped handle wafer, 1 μm thick buried oxide, and highly doped silicon device layer. The process requires 13 lithography masks and 15 lithography steps in total. Polysilicon is used as the sacrificial material, whereas diamond, silicon dioxide are the structural materials. $XeF_2$ plasma is a chemical etchant for polysilicon, whereas silicon dioxide and diamond are not etched with $XeF_2$ etching. Since $XeF_2$ is a plasma at room temperature, during the sacrificial etching of polysilicon, the risk of stiction of the structural layers due to capillary force effect is safely avoided. Furthermore, silicon and polysilicon layers, which construct the Faraday cage and bottom electrode of the CMUT array element, are enclosed with silicon dioxide and diamond so that those layers are not etched during the sacrificial etching of polysilicon in $XeF_2$ plasma.

There are three polysilicon depositions in the proposed microfabrication, where two of the polysilicon layers are sacrificial layers and the other layer is the bottom electrode of the CMUT. There are two boron doped nanocrystalline diamond (BNCD) depositions where one of the BNCD layers is for the diamond emitter, whereas the other layer constructs the membrane and top electrode of the CMUT and the grounded side of the lightning rod structure. There is one thermally grown silicon dioxide layer on the patterned device layer of the SOI wafer. There are four low temperature silicon dioxide (LTO) depositions, where two of the LTO layers are hard masks for diamond etching with the reactive ion etching (RIE) technique, one LTO layer forms the anchor of the CMUT structure, and the remaining LTO layer is for sealing of the CMUT cavities after sacrificial etching. There is one high temperature silicon dioxide (HTO) layer deposition, where the HTO layer provides electrical and chemical isolation for the CMUT cell and the underneath polysilicon layer during the sacrificial etching. Finally, there is one metal deposition for providing required electrical pad connections.

Simulation results that were obtained from Semulator3D (Coventor, USA), ADS (Keysight, USA), and EMPro (Keysight, USA) are provided to show the benefit of the grounded and floating operation of the individual Faraday cage of the CMUT array element during the transmit and receive operations. The simulations show that floating Faraday cage decreases the parasitic capacitance by up to 51.4% and coupling capacitance by 27.6% compared to comparable regular CMUT. In the grounded operation Faraday cage, the electrical crosstalk between neighboring arrays is improved by up to 97.72 dB compared to comparable regular CMUT arrays. The advantage of the grounded and floating state of the Faraday cage according to the transmit (grounded Faraday cage) and receive (floating Faraday cage) operation of the CMUT array element, is increasing both the receiving sensitivity and decreasing the electrical crosstalk. Thus, improving the overall device performance is achieved. The benefit of the third electrode of the CMUT array element is to individually adjust the state of the Faraday cage of the array element as grounded or floating according to the operation (transmit or receive) of each array element individually, regardless of the operation of neighboring array element.

BRIEF DESCRIPTIONS OF THE DRAWINGS

The points and benefits of this invention will be understood by reading the following detailed description in conjunction with the figures, in which:

FIG. 1A shows the cross-sectional view of prior art regular CMUT array with isolation line passing between two neighboring array elements.

FIG. 1B shows the cross-sectional view of prior art trench isolated CMUT array with supporting frame.

FIG. 1C shows the cross-sectional view of prior art post-CMUT structure.

FIGS. 5A-5O show the microfabrication of a Faraday Caged CMUT array featuring diamond emitters acting as lightning rods.

FIG. 5A shows the cross-sectional view of the structure after the device layer of the SOI wafer is patterned with deep reactive ion etching (DRIE).

FIG. 5O shows the cross-sectional view of the structure after the metal deposition and patterning with metal lift-off technique.

FIG. 8A shows the cross-sectional view of the structure built for regular CMUT array.

FIG. 8B shows the cross-sectional view of the structure built for Faraday Caged CMUT array.

FIG. 9A shows the representative capacitance circuitry of the 2-element regular CMUT array.

FIG. 9B shows the simplified version of representative capacitance circuitry of the 2-array regular CMUT array.

FIG. 10A shows the representative capacitance circuitry of the 2-element Faraday Caged CMUT array.

FIG. 10B shows the simplified version of representative capacitance circuitry of the 2-array Faraday Caged CMUT array.

FIG. 11A shows the electrical crosstalk performance based on the capacitance circuitries of the regular and Faraday Caged CMUT arrays for floating substrate.

FIG. 11B shows the electrical crosstalk performance based on the capacitance circuitries of the regular and Faraday Caged CMUT arrays for grounded substrate.

FIG. 12A shows the electrical crosstalk performance based on the 3-D built structures of the regular and Faraday Caged CMUT arrays for floating substrate.

FIG. 12B shows the electrical crosstalk performance based on the 3-D built structures of the regular and Faraday Caged CMUT arrays for grounded substrate.

DETAILED DESCRIPTION OF THE EMBODIMENTS

Although the following detailed description contains many specifics for the purposes of illustration, anyone of ordinary skills in the art will readily appreciate that many variations and alterations to the following exemplary details are within the scope of the invention.

Accordingly, the following preferred embodiment of the invention is set forth without any loss of generality to, and without imposing limitations upon, the claimed invention.

The invention offers a novel design as Faraday Caged CMUT array, which features an additional conductive shield to isolate each array element individually. This electrically-addressable conductive shield (a.k.a. Faraday Cage) in floating state reduces the parasitic capacitance and cross-coupling capacitance to boost receive sensitivity, and this shield in grounded state reduces the electrical crosstalk. Because the state of this shield is electrically controlled as floating or grounded via a third terminal for each array element, the Faraday Caged CMUT array has elements, where each element is having a top electrode (grounded), a bottom electrode (transmit: DC bias+AC signal applied, receive: DC bias+AC signal detected via a transimpedance amplifier) and a third terminal (grounded or floating). The shield is connected to a novel lightning rod structure having diamond emitters in a cavity. Therefore, the shield in the reliable floating state can be perpetually maintained without the risk of dielectric failure due to exceeding the electrical field breakdown strength around the shield.

Our invention includes the following embodiments:

7) An individual Faraday cage placed below the bottom electrode and separated by an insulating dielectric layer for each CMUT array element.

8) Electrical isolation of Faraday cage from the other two electrodes (top and bottom) of the CMUT array element.

9) Grounded state of the Faraday cage during the transmit operation of the corresponding CMUT array element.

10) Floating state of the Faraday cage during the receive operation of the corresponding CMUT array element.

11) A safe discharging path for the Faraday cage in the floating state using diamond emitters as lightning rods in a cavity.

12) Diamond membrane CMUT array microfabrication based on the sacrificial etching of silicon in $XeF_2$ plasma.

Figure 1A:
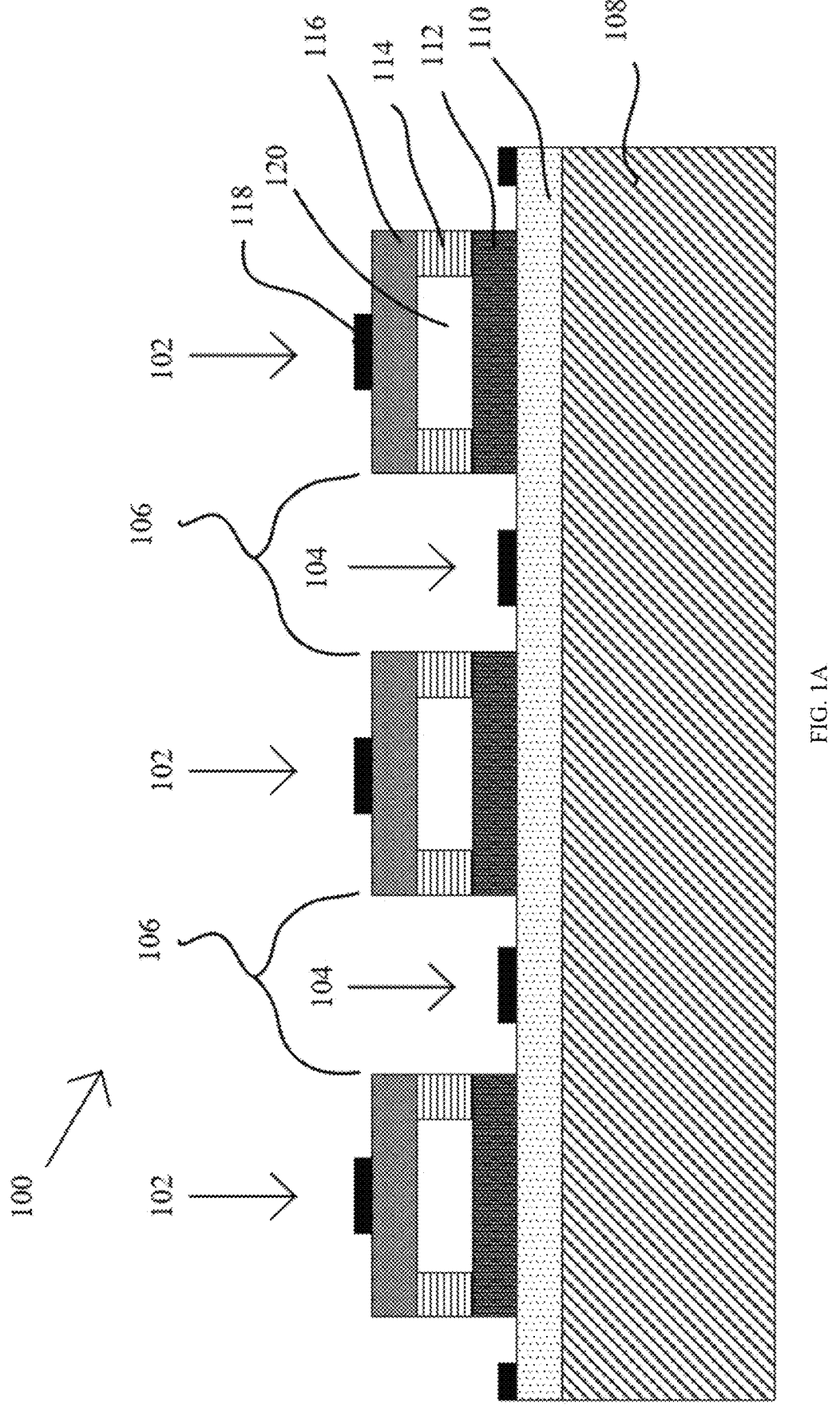
FIGS. 1A-1C show the prior art regular CMUT arrays.

The cross-sectional view of the regular CMUT array 100 found in the prior art is given in FIG. 1A. Three neighboring regular CMUT array elements 102 are shown in FIG. 1A where there is an isolation line 104 in the separation region 106 of each neighboring CMUT array element 102. The isolation line 104 is continuous throughout the structure and is grounded. The regular CMUT array 100 is realized on the silicon substrate 108. There is an isolation layer 110 on top of the silicon substrate 108, which electrically isolates the bottom electrode 112 of CMUT array elements from the silicon substrate 108. Doped polysilicon might be used as the bottom electrode 112 of the CMUT array element. There is an anchor layer 114, which is made of a dielectric material such as silicon dioxide, and it provides the mechanical support to membrane 116. The anchor layer 114 electrically isolates the bottom electrode 112 and the membrane 116. The membrane 116 material might be a conductor (such as metal or doped polysilicon), a doped semiconductor (such as silicon or diamond), or a dielectric (such as silicon nitride). When a voltage is applied between the bottom electrode 112 and the top electrode 118, the membrane 116 can move in the cavity 120 of the CMUT cell. The top electrode 118, which is metal, is placed on the top of the membrane 116 and provides the required electrical connections to the CMUT cell.

Figure 1B:
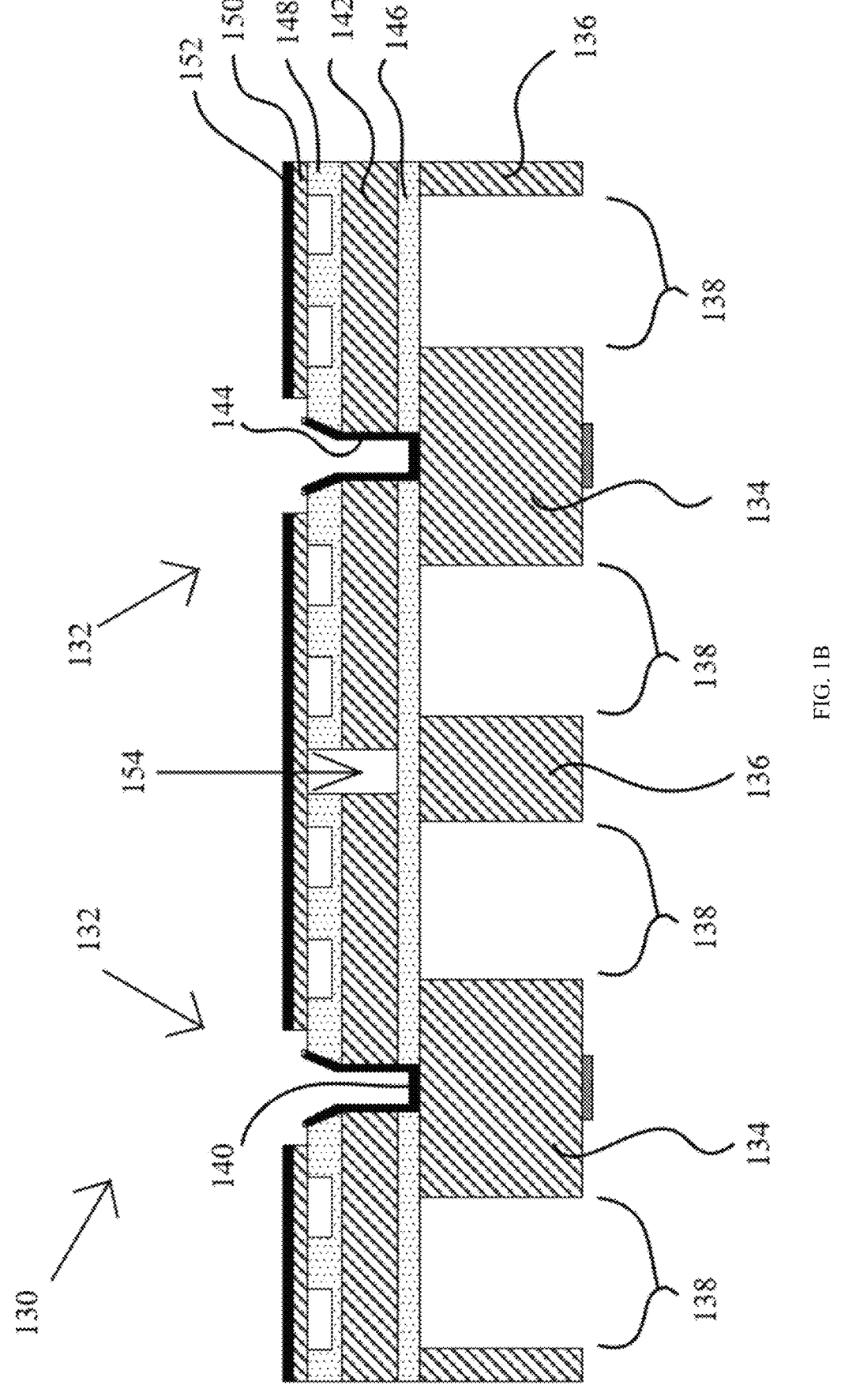

FIG. 1B shows the cross-sectional view of the trench isolated CMUT array 130 with supporting frame. The electrical connections of the CMUT array elements 132 are provided from the backside of the handle wafer. Deep trenches throughout the handle are etched to construct the hot electrodes 134, which carry the electrical signals to the CMUT array elements 132, and the supporting frame 136, which provides the mechanical support to the structure. The supporting frame 136 is continuous like a meshwork throughout the structure, and it is grounded. Thus, the separation 138 between the hot electrodes 134 and the supporting frame 136 is constructed. Both the hot electrodes 134 and supporting frame 136 are conductive. The hot electrode 134 carries the electrical signal to CMUT array elements 132 through the deposited metal that is contacting the hot electrodes from the top side 140 and bottom electrode 142 of the CMUT array element from the side wall 144. The bottom electrode 142 of the CMUT array is the etched device layer of the SOI wafer. The bottom electrodes of the CMUT array elements are separated from each other with etching of the device layer wherein the separation 146 is shown in FIG. 1B. There is buried oxide 146, silicon dioxide anchor layer 148, doped silicon membrane 150, and metal top electrode 152 in the design. The top electrodes 152 of two neighboring CMUT array elements are common in the structure, and they are grounded. The bottom electrode 144 of neighboring CMUT array elements are isolated from each other, wherein the separation zone 154 is shown in FIG. 1B.

Figure 1C:
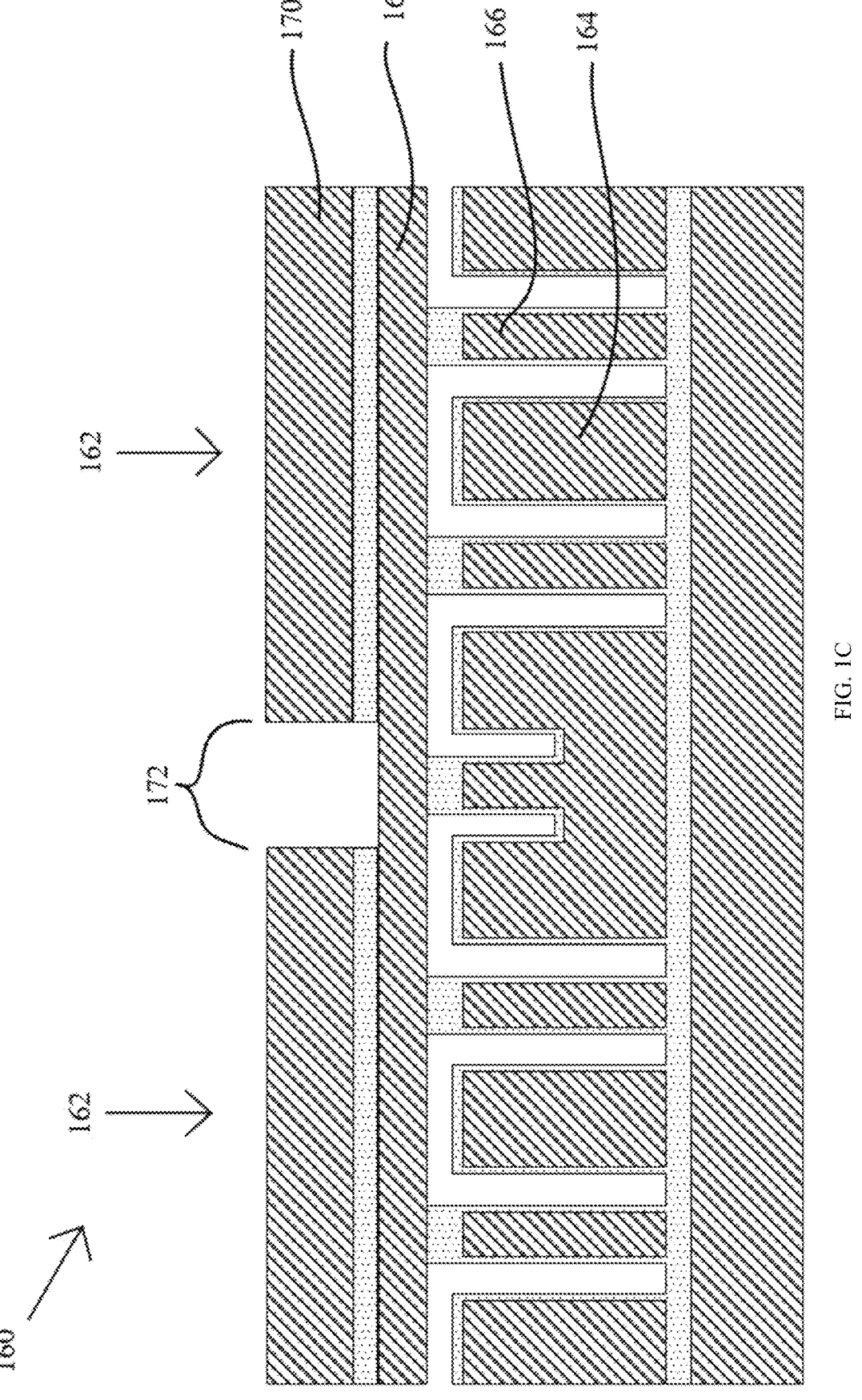

FIG. 1C shows the cross-sectional view of the post-CMUT array 160 structure. Two neighboring CMUT array element 162 is shown in FIG. 1C. The fabrication technique of the structure is based on the wafer bonding of two SOI wafers. The deep trenches on the device layer of the bottom SOI wafer are etched to construct the bottom electrode 164 and the supporting frame 166. The signal is applied to the bottom electrode 164. The supporting frame 166 is continuous throughout the structure, and it is grounded. The bottom electrodes 164 and the supporting frame 166 are isolated from each other, and both are encapsulated with thermally grown silicon dioxide. The device layer 168 and the handle wafer 170 of the top SOI wafer are thin top plate 168 and piston top plate 170 of the structure, respectively. The top thin plate 168 behaves as the top electrode of the CMUT cell, and it is grounded, whereas the piston top plate 170 provides nonflexural plate movement, which resembles the ideal piston movement. The piston top plates of neighboring arrays are separated from each other, wherein the separation 172 is shown in FIG. 1C.

Figure 2:
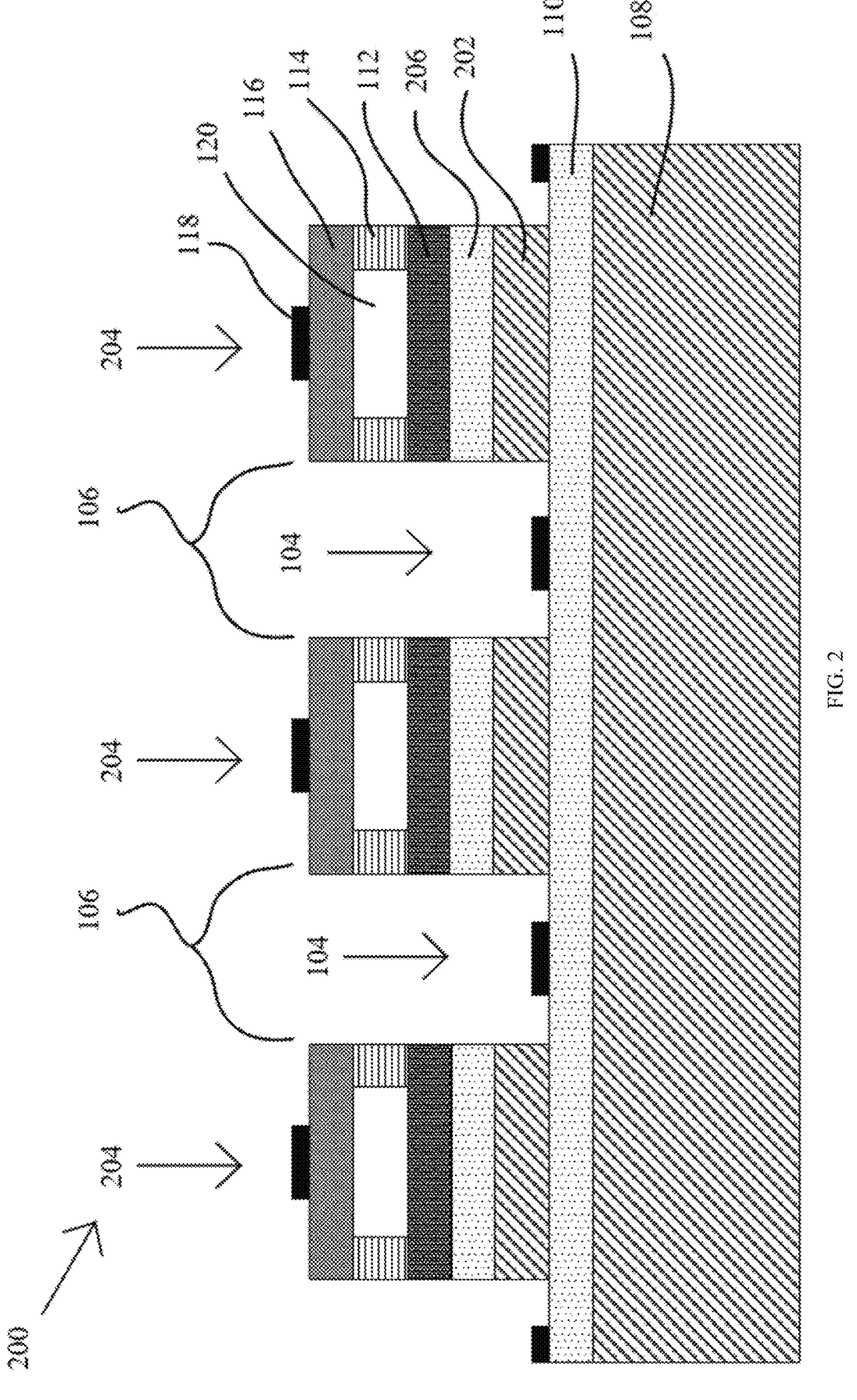
FIG. 2 shows the cross-sectional view of the novel Faraday Caged CMUT array.

The parasitic capacitance, coupling capacitance, and electrical crosstalk are phenomena that affect the CMUT performance adversely. The parasitic capacitance is the additional constant capacitance to the signal to ground capacitance of a CMUT array element. The coupling capacitance is the capacitance between two neighboring array elements. The electrical crosstalk is the coupling of the electromagnetic waves of a CMUT array element to another element. The neighboring array element would affect the parasitic capacitance, the coupling capacitance, and the electrical crosstalk through the silicon substrate. Thus, placing an individual Faraday cage underneath the CMUT array element would suppress the effects coming through the silicon substrate significantly. The cross-sectional view of the Faraday Caged CMUT array 200 that includes individual Faraday cage 202 for each CMUT array element 204 is shown in FIG. 2. The Faraday Caged CMUT array 200 has some matching parts with the regular CMUT array 100 shown in FIG. 1A. The main difference between the arrays is the existence of a Faraday cage 202 underneath the bottom electrode 112 of each CMUT array element 204. Faraday cages 202 are constructed from the device layer of the SOI wafer, which is doped silicon, whereas each Faraday cage 202 of a CMUT array element is separated from the other, wherein the separation 106 is shown in FIG. 2. The Faraday cages 202 are electrically isolated from the bottom electrodes 112 and the silicon substrate 108 with above 206 and below 110 thermally grown silicon dioxide layers. The individual Faraday cage 202 of a CMUT array element 204 requires a third electrode that controls the Faraday cage 202.

The FEA simulations of the regular CMUT array and Faraday Caged CMUT array are performed to compare the electrical crosstalk and capacitive performance of the arrays wherein the same size and materials are used for the matching parts of the arrays. The details of the FEA simulations are explained in the following. It is observed from the FEA simulations that:

4) Compared to the regular CMUT array in the Faraday Caged CMUT array, the parasitic capacitance is reduced by 35.7% and 51.4% for a floating and grounded silicon substrate when the individual Faraday cages are floating, respectively.

5) Compared to the regular CMUT array in the Faraday Caged CMUT array, the coupling capacitance is reduced by 27.6% when the individual Faraday cages are floating, regardless of floating or grounded silicon substrate.

6) Compared to the regular CMUT array in the Faraday Caged CMUT array, the electrical crosstalk is reduced by 97.72 dB and 6.75 dB for floating and grounded silicon substrate when the individual Faraday cages are grounded, respectively.

Figure 3:
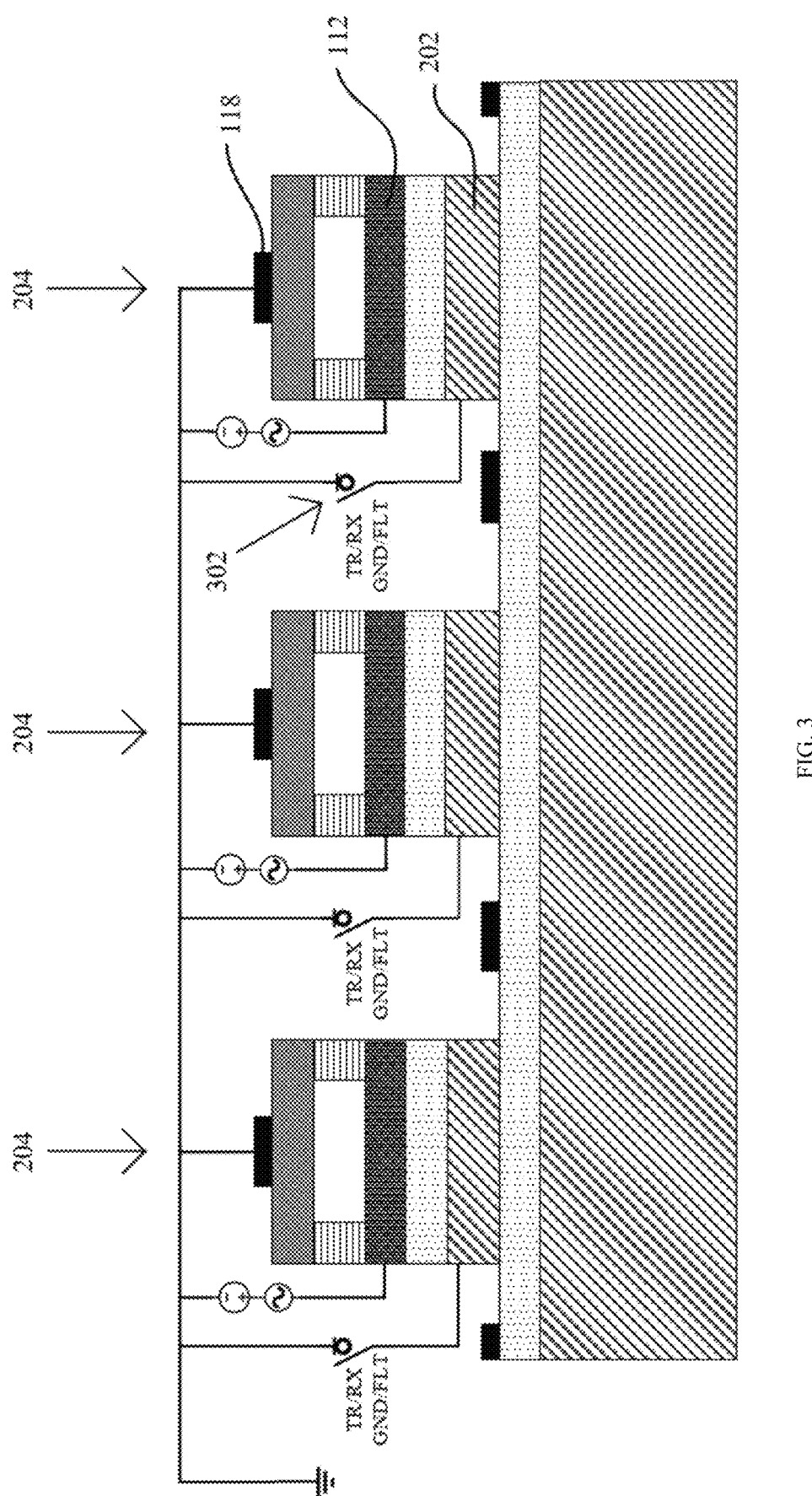
FIG. 3 shows the proposed operational method of the Faraday Caged CMUT array.

The CMUT array elements can perform transmit or receive operations regardless of the operation of the neighboring array element. During the receive operation, small changes in the capacitance are to be detected, whereas, in the transmit operation, a high voltage is applied to create the acoustic waves. Thus, the parasitic and coupling capacitance is more important in the receive operation of the CMUT array. On the other hand, the coupling of the electromagnetic waves from the current array element to the neighboring array element is more important in the transmit operation of the CMUT array. From these facts stated above, a floating operation of the Faraday cage during the receive operation is beneficial, whereas the grounded Faraday cage is advantageous during the transmit operation. FIG. 3 shows the proposed operational method of the Faraday Caged CMUT array. The DC bias and the AC signal are applied to the bottom electrode 112, where the top electrodes 118 of the CMUT array elements 204 are all grounded. The third electrode of the CMUT array element controls the state of the Faraday cage 202. The state of each Faraday cage is optimally selected based on the operation of the corresponding CMUT array element. When the CMUT array element is in transmit (TR) mode, the switch 302, which is connected to the ground and Faraday cage, is closed, and thus, the Faraday cage is in grounded (GND) state, whereas when the array element is in receive (RX) mode, the switch 302 is open, and thus, the Faraday cage is in floating (FLT) state.

Figure 4:
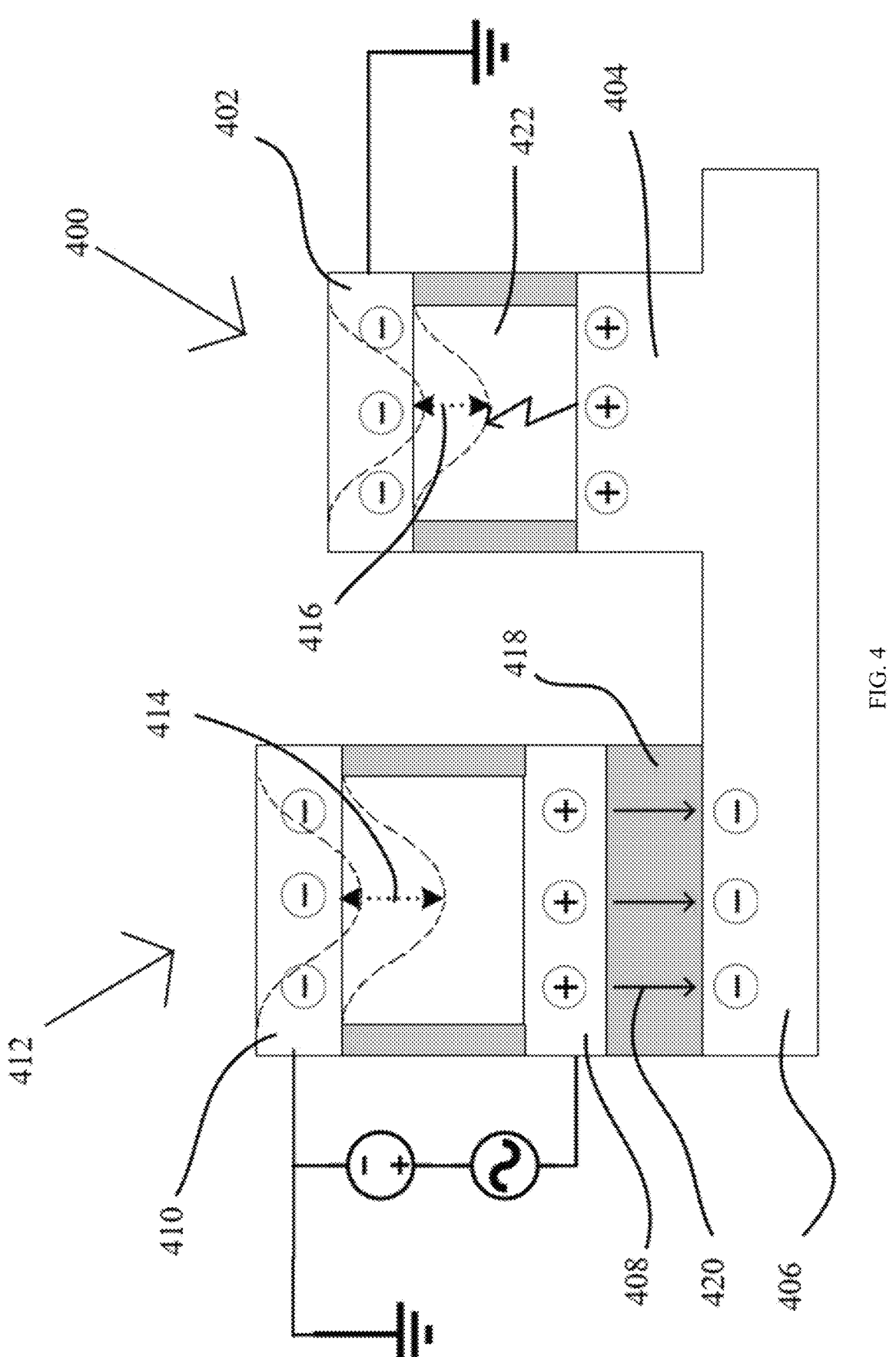
FIG. 4 shows the working principle for charge polarization and gradual charging of the floating Faraday cage via the leakage current through the dielectric and the discharging of the floating Faraday cage through the lightning event in the cavity.

The floating state of a conductor in a structure might be harmful to the device due to the dielectric breakdown. The floating conductor might acquire a higher voltage than it should, or charge might be accumulated during the usage of the device due to the leakage current in the structure. This would result in discharging of the floating conductor through the dielectric, which is a catastrophic failure for the device. This has a negative impact on the high voltage operation and lifetime of the device. The current invention includes a safe discharging path for the Faraday cage during the floating state based on a lightning rod structure for the first time in CMUT arrays. FIG. 4 shows the working principle of the lightning rod structure 400. The lightning rod has two sides, top side 402 and bottom side 404. The top side 402 of the lightning rod structure is BNCD and connected to the ground. The bottom side 404 of the lightning rod is the diamond emitter and connected to the floating conductor 406. When positive DC bias and AC signal is applied to the bottom electrode 408 where the top electrode 410 of the CMUT cell 412 is grounded, the bottom electrode would be positively charged, whereas the negative charges will be accumulated in the top electrode due to the DC bias. Thus, the electrostatic force would be formed between the electrodes, and top electrode would move towards the bottom electrode, wherein the movement 414 of the top electrode is shown in FIG. 4 with a double-sided arrow. Due to the positive DC bias applied to the bottom electrode 408, the negative charges on the floating conductor 406 would be accumulated near to bottom electrode, whereas the same amount of positive charges would be pushed away to the bottom side 404, which is the diamond emitter, of the lightning rod structure 400. Therefore, charge is acquired on the floating conductor depending on the DC bias applied to the bottom electrode. Then, the negative charges would be accumulated in the top side 402 of the lightning rod structure. Thus, the moveable top side 402 of the lightning rod would move towards the bottom side 404, wherein the movement 416 of the top side 402 is shown in FIG. 4 with a double-sided arrow. After that, according to the turn-on field value of the diamond emitter, which is less than 20 V/μm, the floating Faraday cage will be discharged to the top side of the lightning rod 402 through the diamond emitter 404.

Furthermore, the top electrode 410 of a CMUT cell would vibrate due to the applied AC signal. This vibration and DC bias already applied on the bottom electrode 408 would cause the leakage current from the bottom electrode 408 to the floating conductor 406 through the dielectric 418, wherein the leakage current 420 is shown with arrows in FIG. 4. This leakage current might be small in value, but with long time operation of the CMUT array, there might be severe charge accumulation in the floating conductor 406. The accumulated charges in the floating conductor would induce charges on the top side 402 of the lightning rod increasing electrostatic force between the top 402 and bottom 404 sides of the lightning rod structure. Then, the top side 402 would move towards bottom side 404, wherein the movement 416 of the top side 402 is shown in FIG. 4 with a double-sided arrow. After that, according to the turn-on field value of the diamond emitter, which is less than 20 V/μm, the floating Faraday cage will be discharged to the top side of the lightning rod 402 through the diamond emitter 404. The turn-on voltage can be controlled by the features of the diamond emitter 404 and the gap between the top side 402 and bottom side 404 of the lightning rod. Also, the thickness of the dielectric 418 is effective on the leakage current and the voltage acquired on the floating conductor.

The movability of the top side of the lightning rod facilities discharging of the floating conductor by reducing the gap between the top and bottom sides. The gap 422 between the top side 402 and bottom side 404 can be vacuum or air; the cavity can be vacuum-sealed or can have partial atmospheric pressure. An important similarity between the CMUT and the lightning rod structures is the fact that both of them feature a grounded top electrode that can move towards the bottom electrode due to electrostatic forces. An important distinction between them is that the CMUT is a voltage-controlled device, whereas the lightning rod structure is a charge-controlled device. This charge-controlled device accumulates charges in time through the leakage currents 420 based on the voltages applied on the bottom electrode 408 of the CMUT, and diamond emitters within the lighting rod structure can intermittently discharge once the critical breakdown field in the cavity is reached. This discharge event in the cavity, unlike the dielectric breakdown, is completely safe and does not harm the MEMS structure in any way. Therefore, floating state of a conductor can be reliably maintained perpetually for a CMUT array with the intermittent discharging through the diamond emitters within the lightning rod structure.

Another aspect of the invention, wherein the dimensions of the CMUT array design are as follows:

Handle wafer thickness ($t_{subs}$) is 400 μm

Buried oxide thickness ($t_{BOX}$) is 1 μm

Device layer (Faraday cage) thickness ($t_{Faraday}$) is 2 μm

Thermally grown silicon dioxide thickness ($t_{therox}$) is 1 μm

Bottom electrode thickness ($t_{bottom}$) is 500 nm

Pillar shaped diamond emitter thickness ($t_{emitter}$) is 500 nm

Diamond emitter radius ($r_{emitter}$) is 50 nm.

Electrical insulation thickness ($t_{ins}$) is 150 nm

Anchor thickness ($t_{anc}$) is 1 μm

Etch channel thickness ($t_{etc}$) is 250 nm

Gap thickness ($t_{gap}$) is 1.1 μm

Membrane thickness ($t_{mem}$) is 1 μm

Metal thickness ($t_{metal}$) is 500 nm

Radius of the circular shaped membrane ($r_{mem}$) is 18 μm

Radius of the circular shaped etch via ($r_{etchvia}$) is 2 μm

Distance between two neighboring CMUT cell ($d_{C2C}$) is 7.3 μm

Width of the CMUT array ($w_A$) is 116 μm

Thickness of the dimples ($t_{dimple}$) is 250 nm

Width of the isolation line ($w_{iso}$) is 10 μm

Radius of the dimples ($r_{dimple}$) is 2 μm

Distance between two neighboring CMUT array ($d_{A2A}$) is 28 μm

Width of the lightning rod ($w_{LR}$) is 4 μm

The method for microfabrication of a diamond membrane Faraday Caged CMUT, with above mentioned dimensions, is performed through following the steps, where the microfabrication is realized on SOI wafer with 400 μm thick n-type handle wafer <100> 502, 1 μm thick buried oxide 504 and 2 μm thick highly doped n-type device layer <100> 506:

24) Patterning of the device layer 506 to construct the Faraday cage of the CMUT array element with lithography and DRIE.

"Mask #1-DRIE" mask is used during the exposure of the photoresist.

Figure 5A:
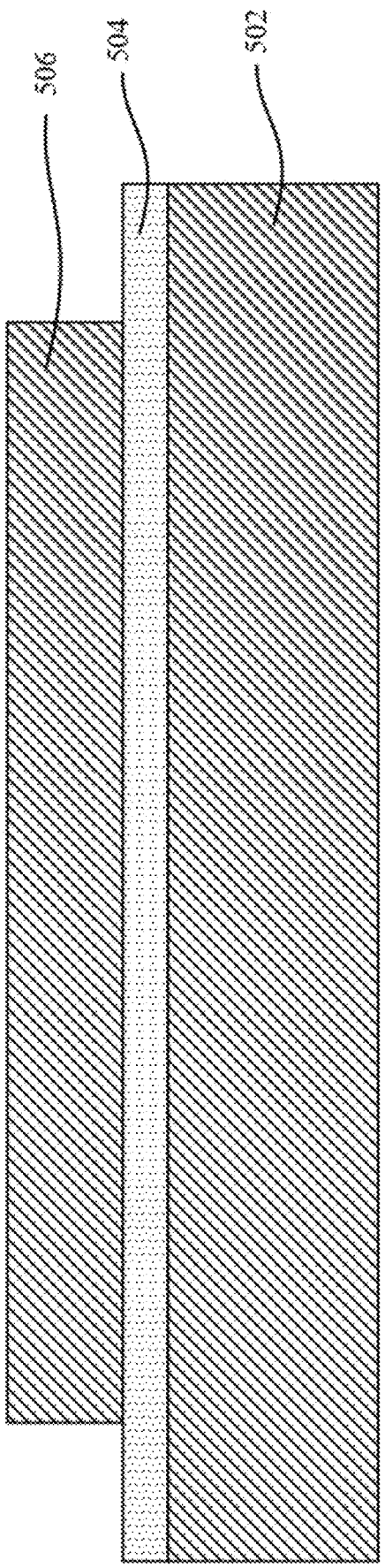
Figure 5B:
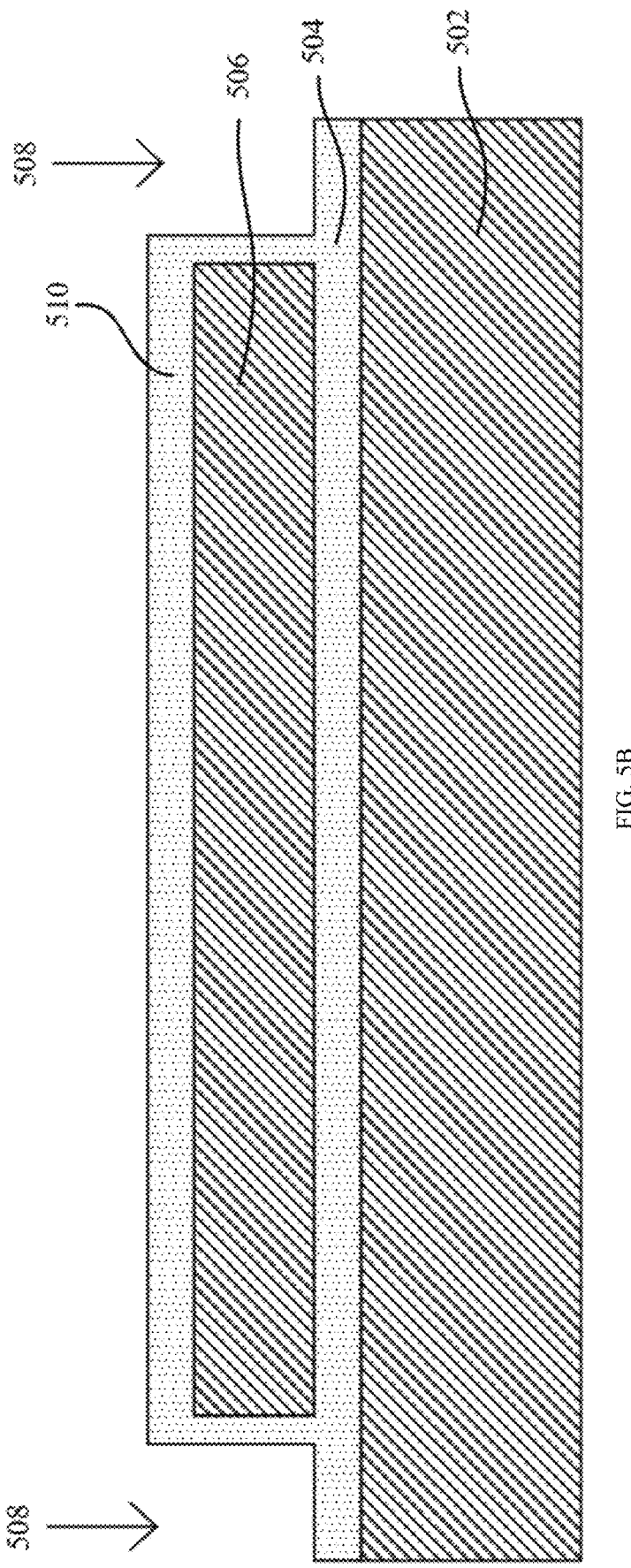
FIG. 5B shows the cross-sectional view of the structure after the silicon dioxide is thermally grown.

The silicon in the separation zone is etched away, wherein half of the separation zone 508 is shown in FIGS. 5A-5B.

25) 1 μm thick silicon dioxide 510 is thermally grown as depicted in FIG. 5B.

The recipe of the thermal oxidation is;

i. dry oxidation for 30 minutes ii. wet oxidation iii. final thermal oxidation for 30 minutes The thickness of the silicon dioxide layer is determined with the dry-wet-dry oxidation steps.

The initial and last dry oxidations improve the quality of the silicon dioxide.

The silicon dioxide grown at the backside of the handle wafer is removed in this step.

26) 500 nm thick first polysilicon layer deposition with low temperature chemical vapor deposition (LPCVD) followed doping of the polysilicon with phosphorus.

Figure 5C:
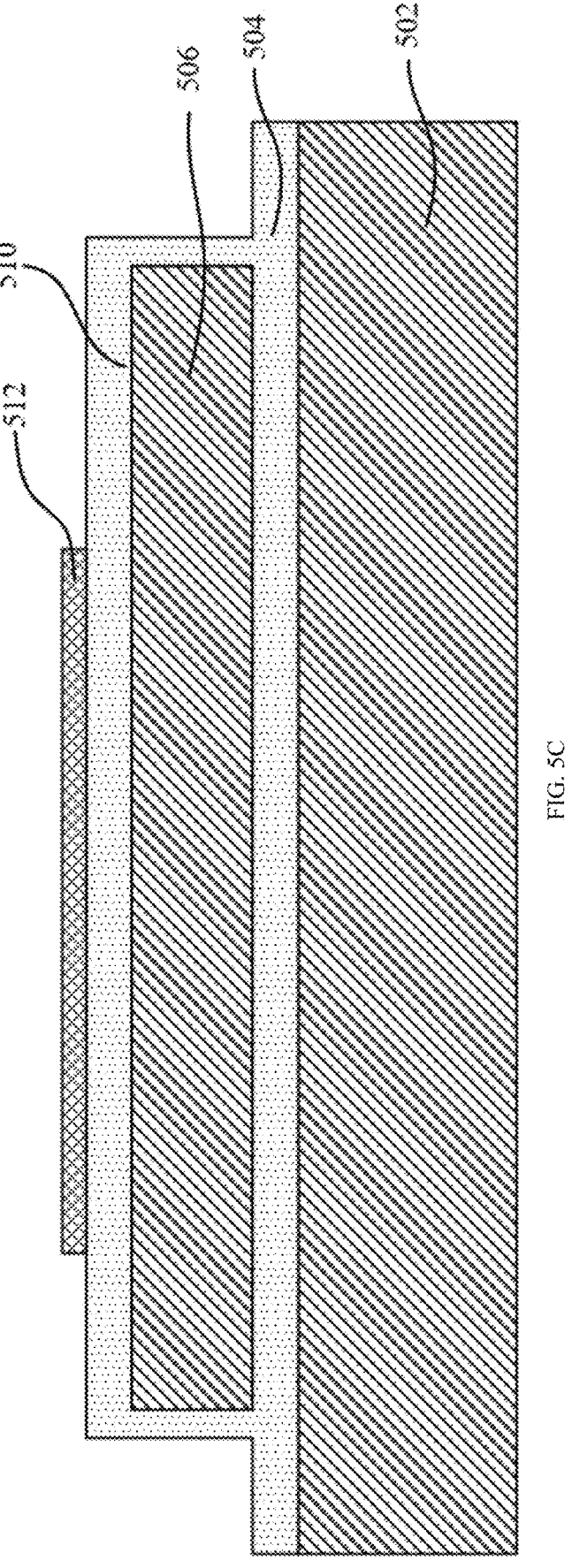
FIG. 5C shows the cross-sectional view of the structure after the first polysilicon deposition and patterning with RIE.

Then patterning of the deposited polysilicon layer with lithography and RIE as depicted in FIG. 5C.

The aim of this step is to define the bottom electrode 512 of the CMUT cell.

"Mask #2-BottomElectrode" mask is used during the exposure of the photoresist.

27) 1 μm thick first LTO layer deposition with LPCVD followed by annealing at 1050° C. for 1 hour in argon. Then patterning of the deposited LTO layer with lithography and RIE.

Figure 5D:
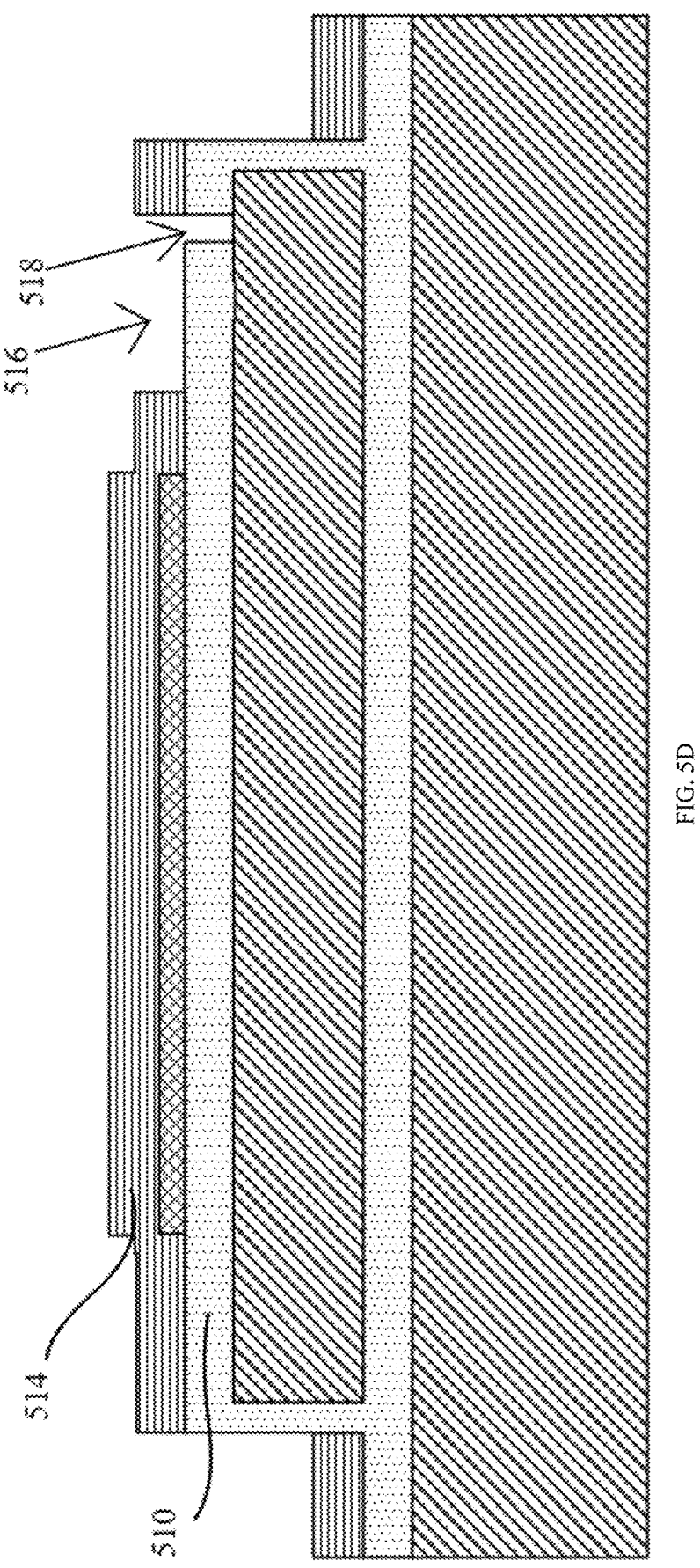
FIG. 5D shows the cross-sectional view of the structure after the first LTO deposition and silicon dioxide patterning with RIE.

This LTO layer will construct the anchor of the CMUT cell, wherein the LTO layer 514 is shown in FIG. 5D.

LTO inside of the area of the bottom side of the lightning rod is etched away with RIE, wherein the area of the bottom side 516 is shown in FIG. 5D.

The RIE is performed to etch the 1 μm silicon dioxide.

"Mask #3-LightningRod" mask is used during the exposure of the photoresist.

28) Patterning of the thermally grown silicon dioxide layer 510 with lithography and RIE as depicted in FIG. 5D.

The goal is to construct the required via 518 on top of the Faraday cage to be able to provide electrical contact between the Faraday cage and the diamond emitter.

"Mask #4-Diamond2Cage" mask is used during the exposure of the photoresist.

29) 1 μm thick first BNCD layer deposition with hot filament chemical vapor deposition (HFCVD).

The resistivity of the deposited BNCD layer is 0.02 ohm·cm.

This layer will be the bottom side of the lightning rod and will include the diamond emitters.

30) 1 μm thick second LTO layer deposition with LPCVD followed by patterning of the deposited LTO layer with lithography and RIE.

This layer will be the hard mask for BNCD patterning with RIE since photoresist cannot be used for diamond RIE.

The LTO outside of the area of the bottom side 516 of the lightning rod is etched away with RIE.

"Mask #3-LightningRod" mask is used during the exposure of the photoresist. The opposite polarity of the mask is used compared to its use in step 4.

31) Patterning of the underneath BNCD layer with RIE while the patterned LTO is the hard mask.

32) Patterning of the remaining LTO hard mask with lithography and RIE.

Figure 5E:
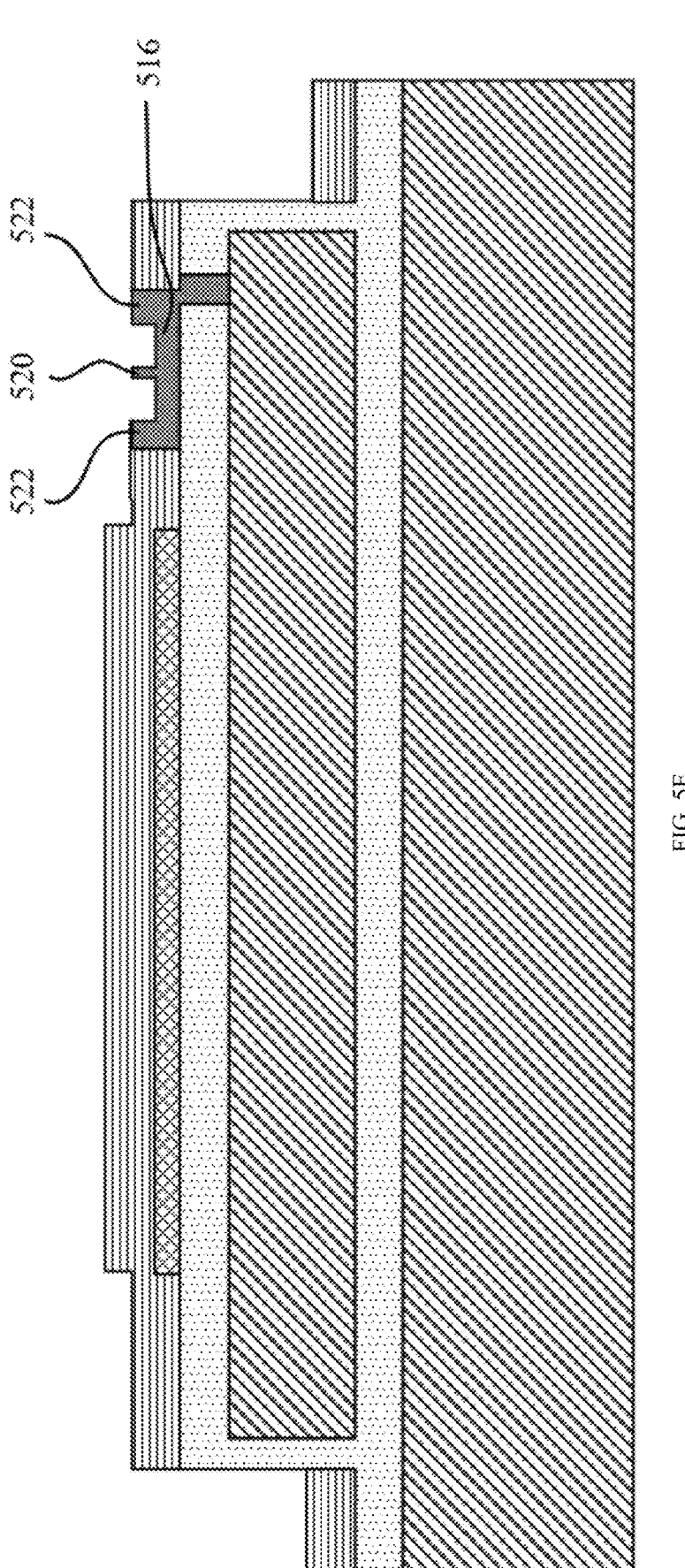
FIG. 5E shows the cross-sectional view of the structure after the pillar shaped diamond emitters are constructed after the first BNCD deposition and patterning with RIE (LTO is used as the hard mask and removed afterwards).

This step aims to define the diamond emitters and the diamond sidewalls of the bottom side of the lightning rod structure wherein the diamond emitters 520 and the diamond sidewalls 522 are shown in FIG. 5E.

LTO hard mask remaining in the inside of the area bottom side 516 and outside of the area of diamond emitters 520 and the diamond sidewalls 522 is etched away with RIE.

"Mask #5-DiamondEmitters" mask is used during the exposure of the photoresist.

33) Patterning of the remaining BNCD layer with RIE while patterned LTO is the hard mask to construct 500 nm thick diamond emitter 520. The RIE is performed to etch the 500 nm BNCD staying inside the area of the bottom side 516 and outside the area of diamond emitters 520 and the diamond sidewalls 522.

34) Removal of the LTO hard mask with lithography and buffered hydrofluoric acid (BHF) as depicted in FIG. 5E.

Photoresist covers the silicon dioxide outside the area of the bottom side 516.

"Mask #3-LightningRod" mask is used during the exposure of the photoresist. The polarity of the mask is the same as its use in step 6.

Figure 5F:
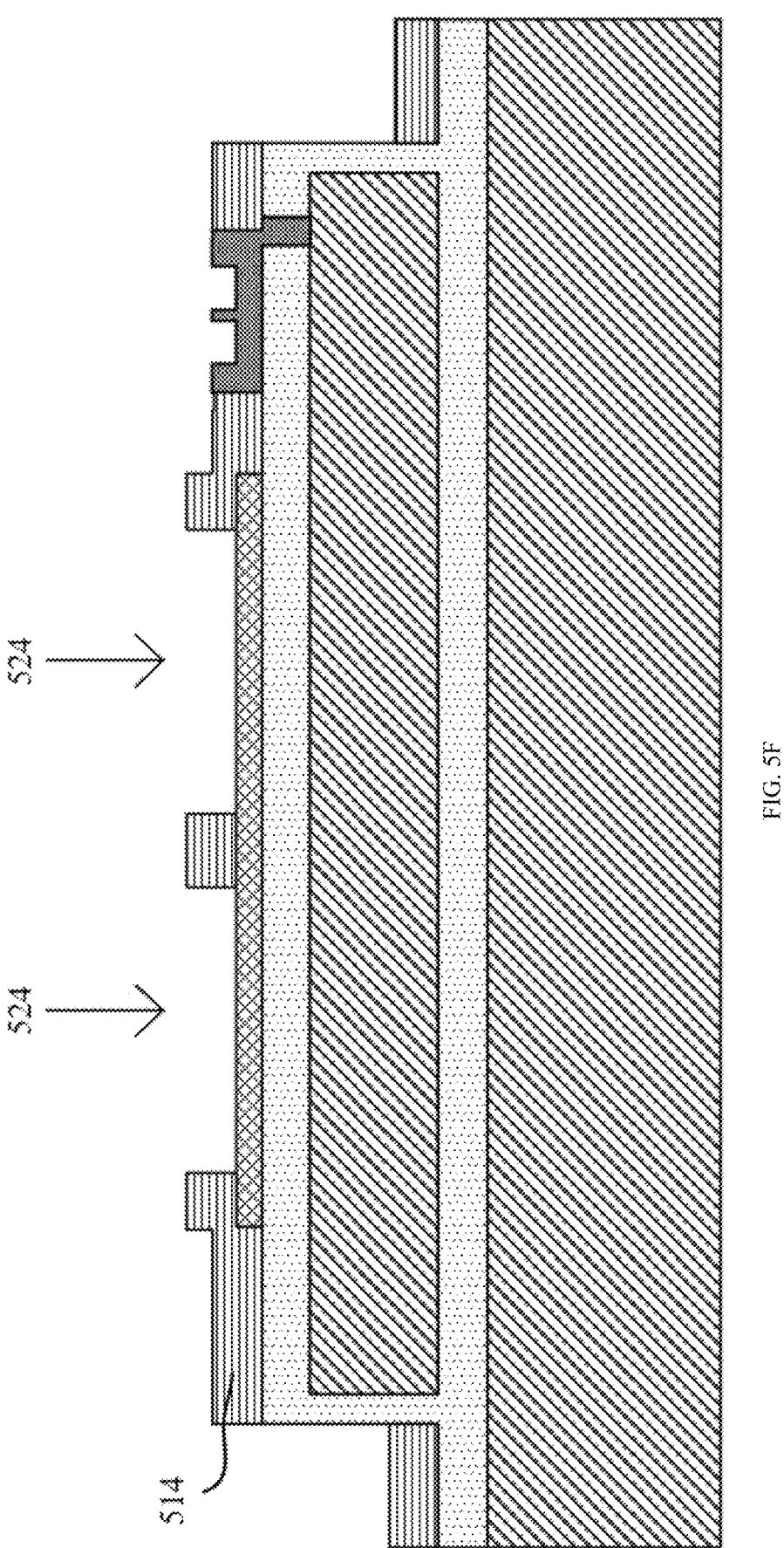
FIG. 5F shows the cross-sectional view of the structure after the patterning of LTO with RIE.

35) Patterning of the first LTO layer 514 with lithography and RIE as depicted in FIG. 5F.

The aim of this step is to construct the anchor for the CMUT cell and define the active area 524 of the CMUT cell.

"Mask #6-CMUTcell" mask is used during the exposure of the photoresist.

Figure 5G:
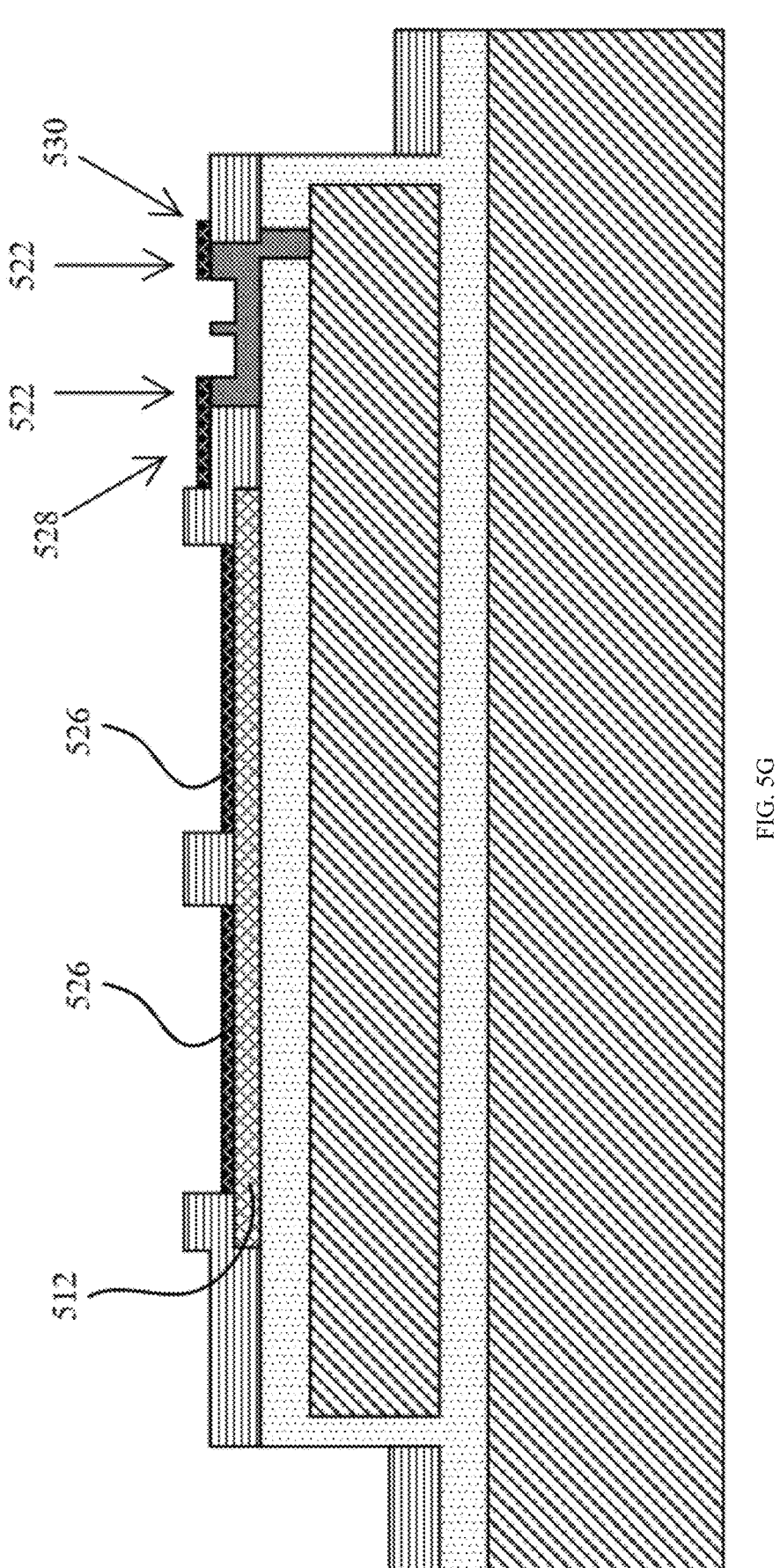
FIG. 5G shows the cross-sectional view of the structure after the HTO deposition and patterning with RIE.

36) 150 nm thick HTO deposition with LPCVD followed by patterning of the deposited HTO layer with lithography and RIE as depicted in FIG. 5G.

The HTO in the active area of the CMUT cell 526 provides chemical coverage for bottom electrode 512 to protect it from being etched during the sacrificial release of polysilicon in the $XeF_2$ plasma process step.

The HTO layer 526 prevents a short circuit between the bottom electrode and the top electrode during the collapse mode of operation or enables resistive-collapse mode of operation for a thin HTO layer (<50 Å) for a membrane with dimples.

The HTO on top of the diamond sidewalls 522 will be the anchor for the lightning rod.

There is HTO in the separation zone 528 of the CMUT array and lightning rod and in the etch channel area 530 of the lightning rod.

The remaining HTO outside the said areas is etched away with RIE.

RIE is performed to etch 150 nm HTO.

"Mask #7-HTO" mask is used during the exposure of the photoresist.

Figure 5H:
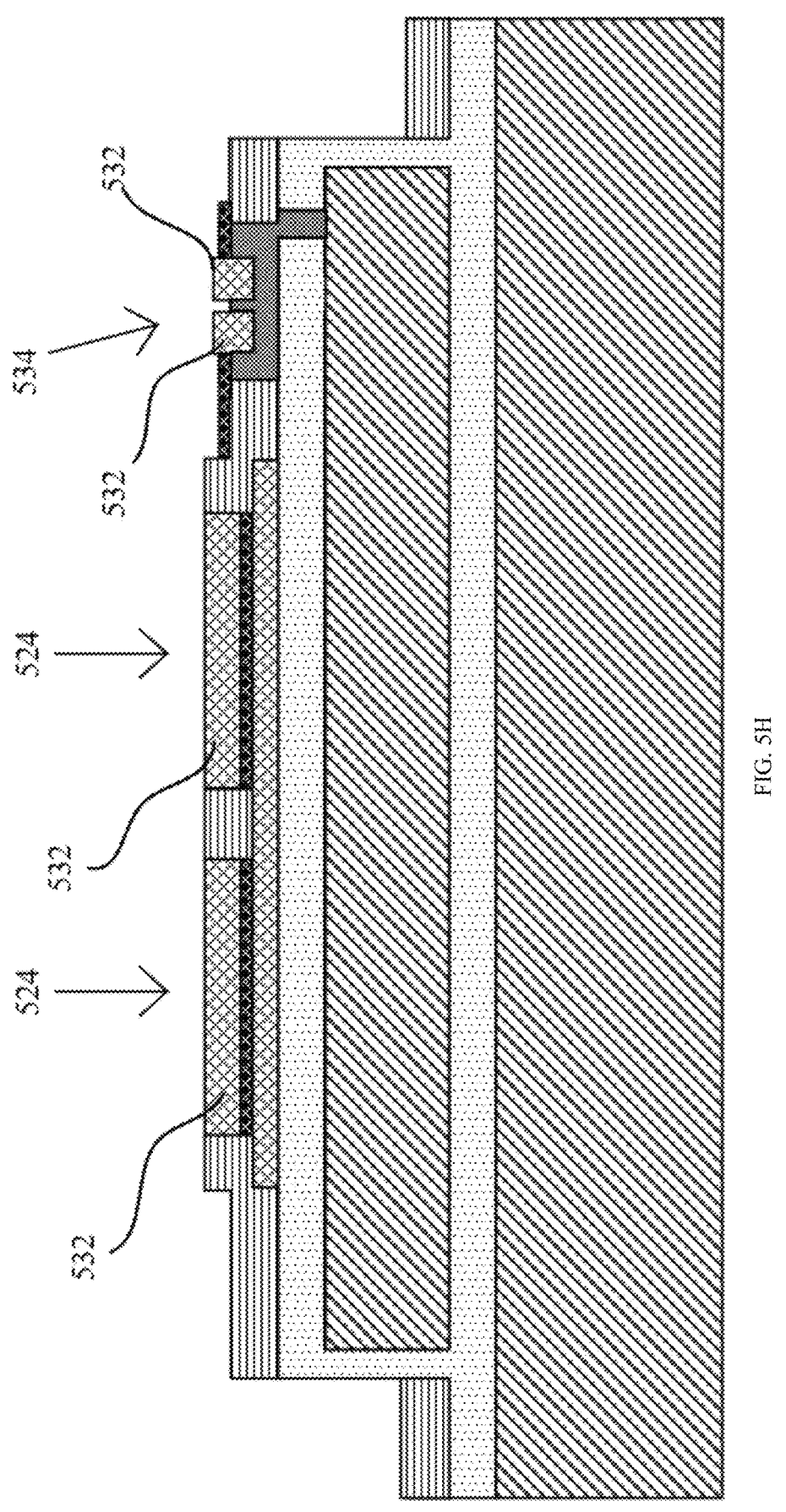
FIG. 5H shows the cross-sectional view of the structure after the second polysilicon deposition and patterning with RIE.

37) 850 nm thick second polysilicon deposition with LPCVD followed by patterning of the deposited polysilicon layer with lithography and RIE as depicted in FIG. 5H.

The aim of this step to construct the sacrificial polysilicon 532 in the active area of CMUT cell 524 and the active area of the lightning rod structure 534.

"Mask #8-ActiveArea" mask is used during the exposure of the photoresist.

38) 250 nm thick second polysilicon deposition with LPCVD followed by patterning of the deposited polysilicon layer with lithography and RIE.

This step aims to define the etch channels for sacrificial etching of polysilicon.

Figure 5I:
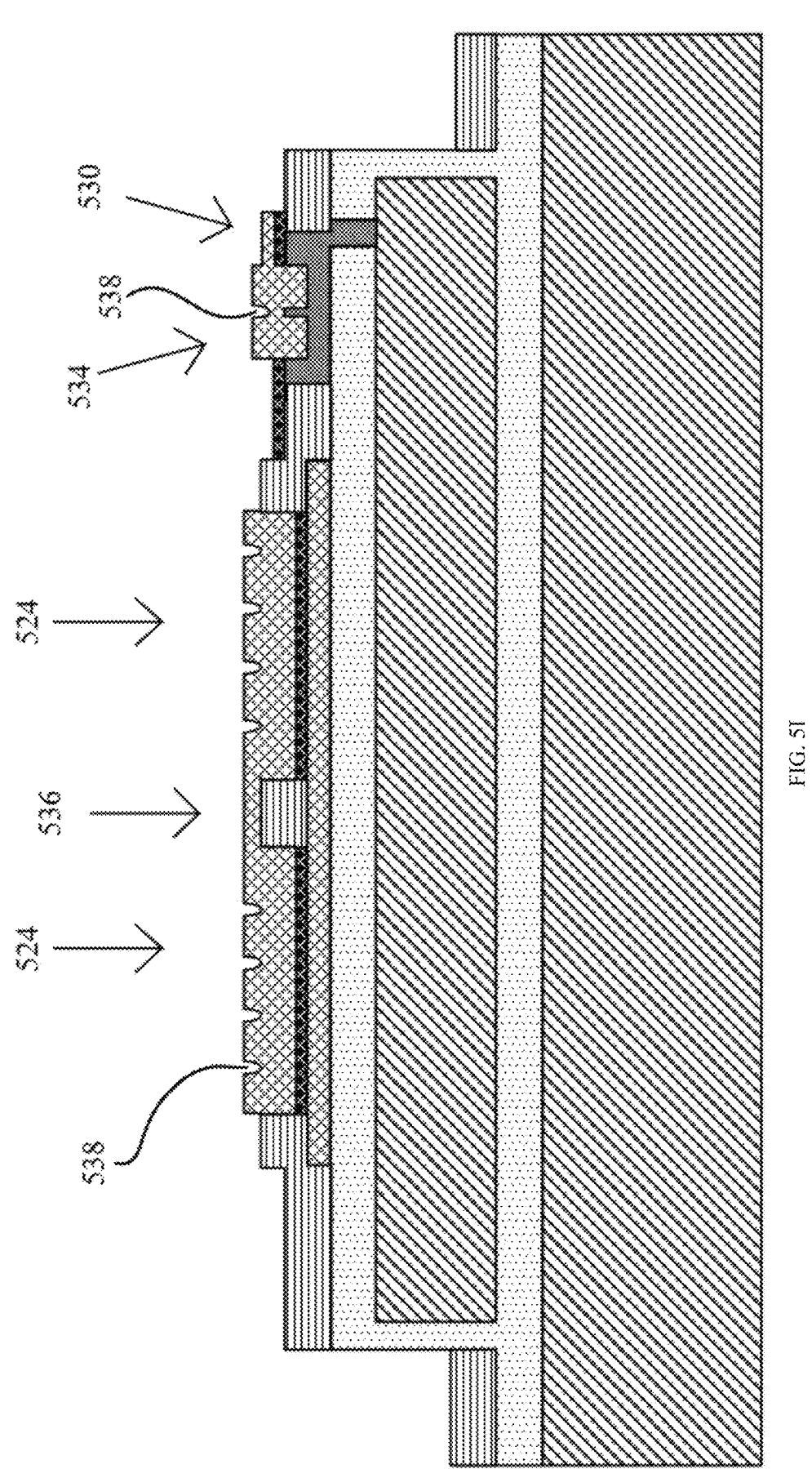
FIG. 5I shows the cross-sectional view of the structure after the third polysilicon deposition and patterning with RIE.

The polysilicon outside of the active area of the CMUT cell 524, the active area of the lightning rod 534, the etch channel of CMUT cell 536, the etch channel of the lightning rod 530, and the area of the diamond emitter 520 is etched away wherein the said areas are shown in FIG. 5I.

"Mask #9-EtchChannel" mask is used during the exposure of the photoresist.

39) The remaining polysilicon is patterned with lithography and RIE to construct the dimples 538 as depicted in FIG. 5I.

Dimples would lessen the probability of stiction of the membrane during the collapse operation or enable resistive-collapse operation for a thin HTO layer (<50 Å).

RIE is performed to etch 250 nm polysilicon.

"Mask #10-Dimple" mask is used during the exposure of the photoresist.

Figure 5J:
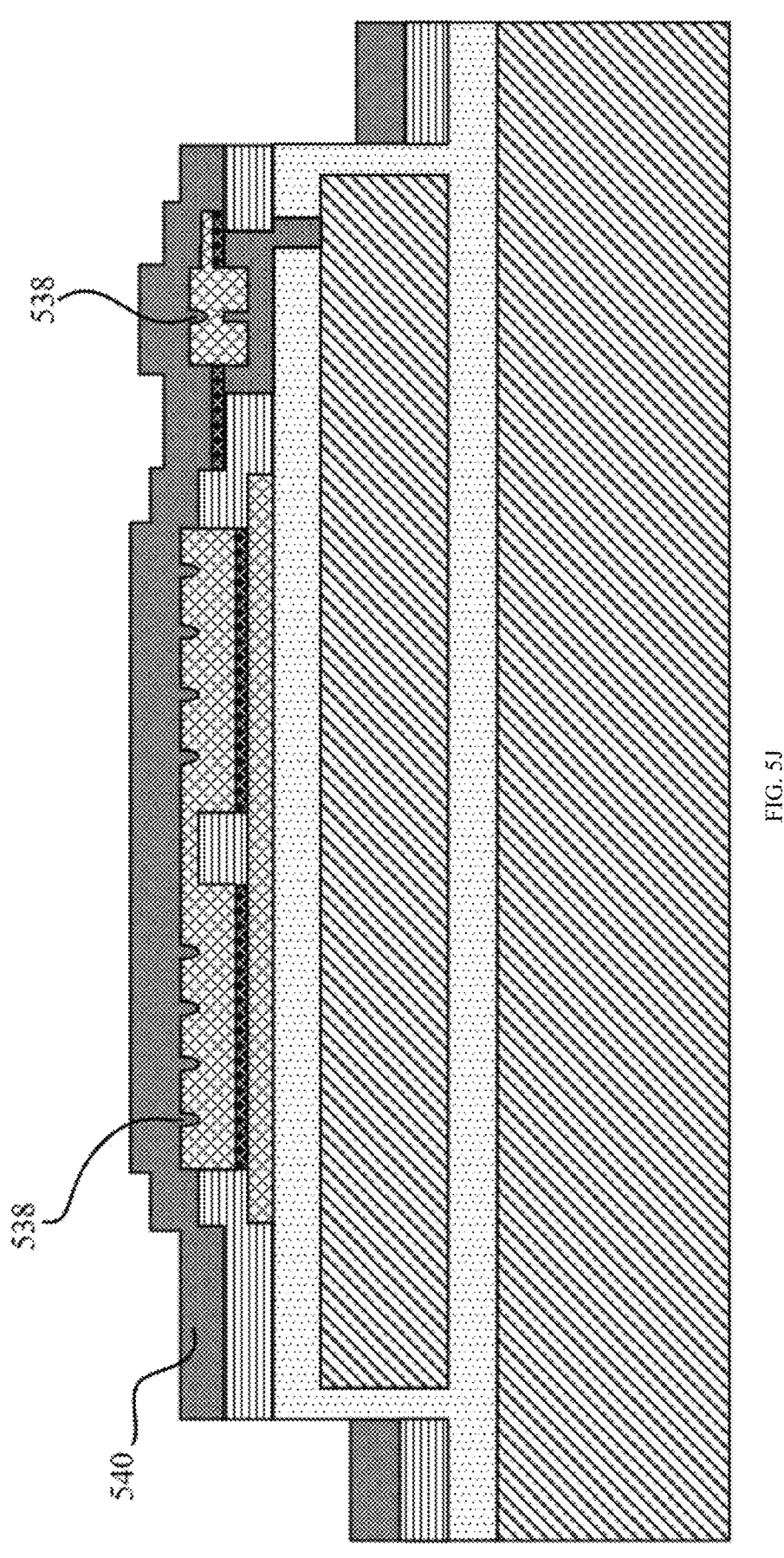
FIG. 5J shows the cross-sectional view of the structure after the second BNCD deposition.

40) 1 μm thick second BNCD 540 deposition with HFCVD as depicted in FIG. 5J.

The resistivity of the deposited BNCD layer is 0.02 ohm·cm.

This layer will be the membrane of the CMUT cell and the top side of the lightning rod.

41) 1 μm thick third LTO deposition with LPCVD as hard mask followed by patterning of the deposited hard mask LTO layer with lithography and RIE.

Figure 5K:
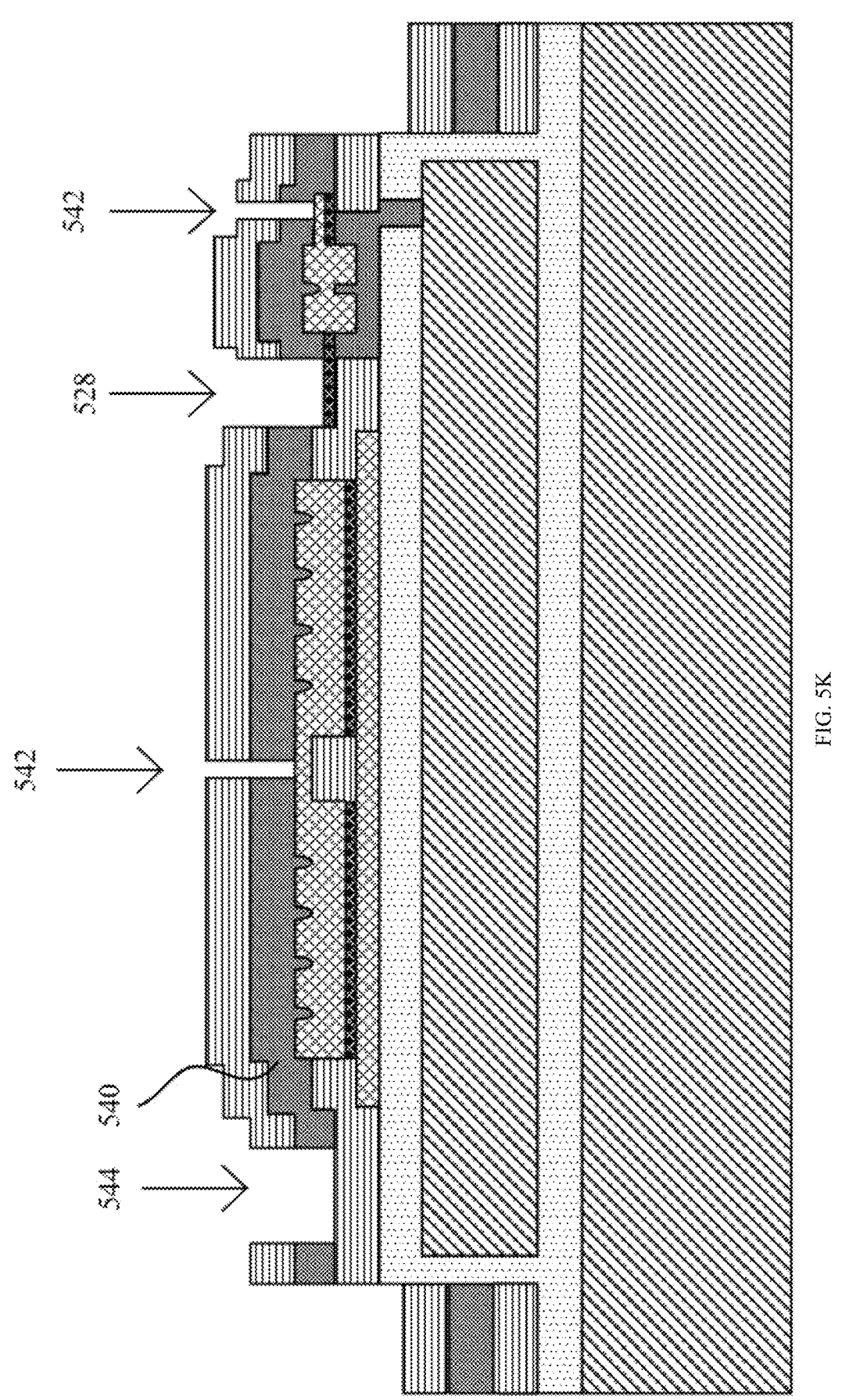
FIG. 5K shows the cross-sectional view of the structure after the patterning of BNCD layer with RIE (LTO is used as the hard mask and is kept in the structure).

The goal of this layer is to define the etch via 542 and the opening for metal pad connections 544 and the separation zone 528 between the membrane of the CMUT cell and the top side of the lightning rod wherein said are shown in FIG. 5K.

"Mask #11-DiamondEtch" mask is used during the exposure of the photoresist.

42) Patterning of the underneath BNCD layer with RIE while the patterned LTO is the hard mask as depicted in FIG. 5K.

Figure 5L:
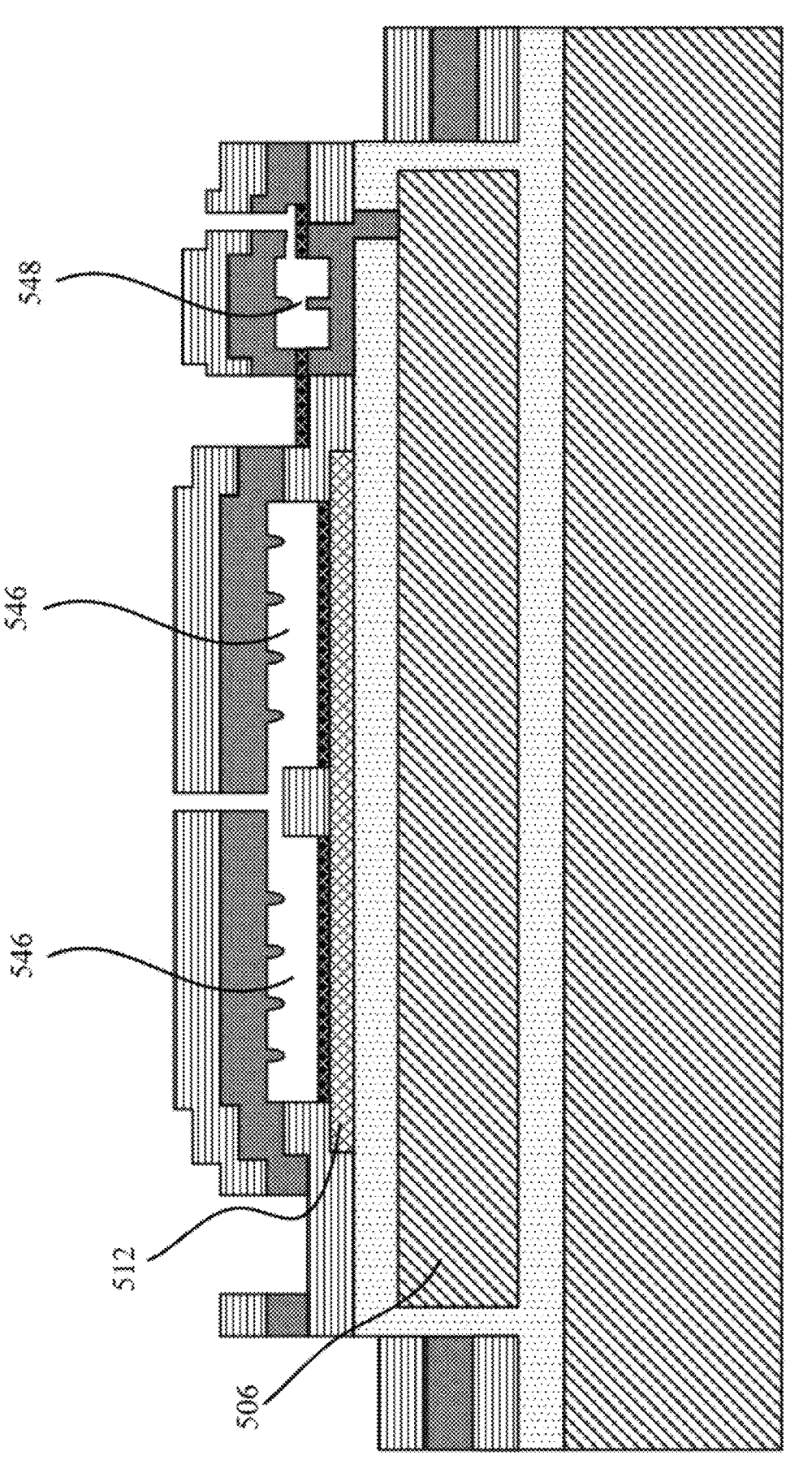
FIG. 5L shows the cross-sectional view of the structure after the polysilicon sacrificial etching in $XeF_2$ plasma.
Figure 5M:
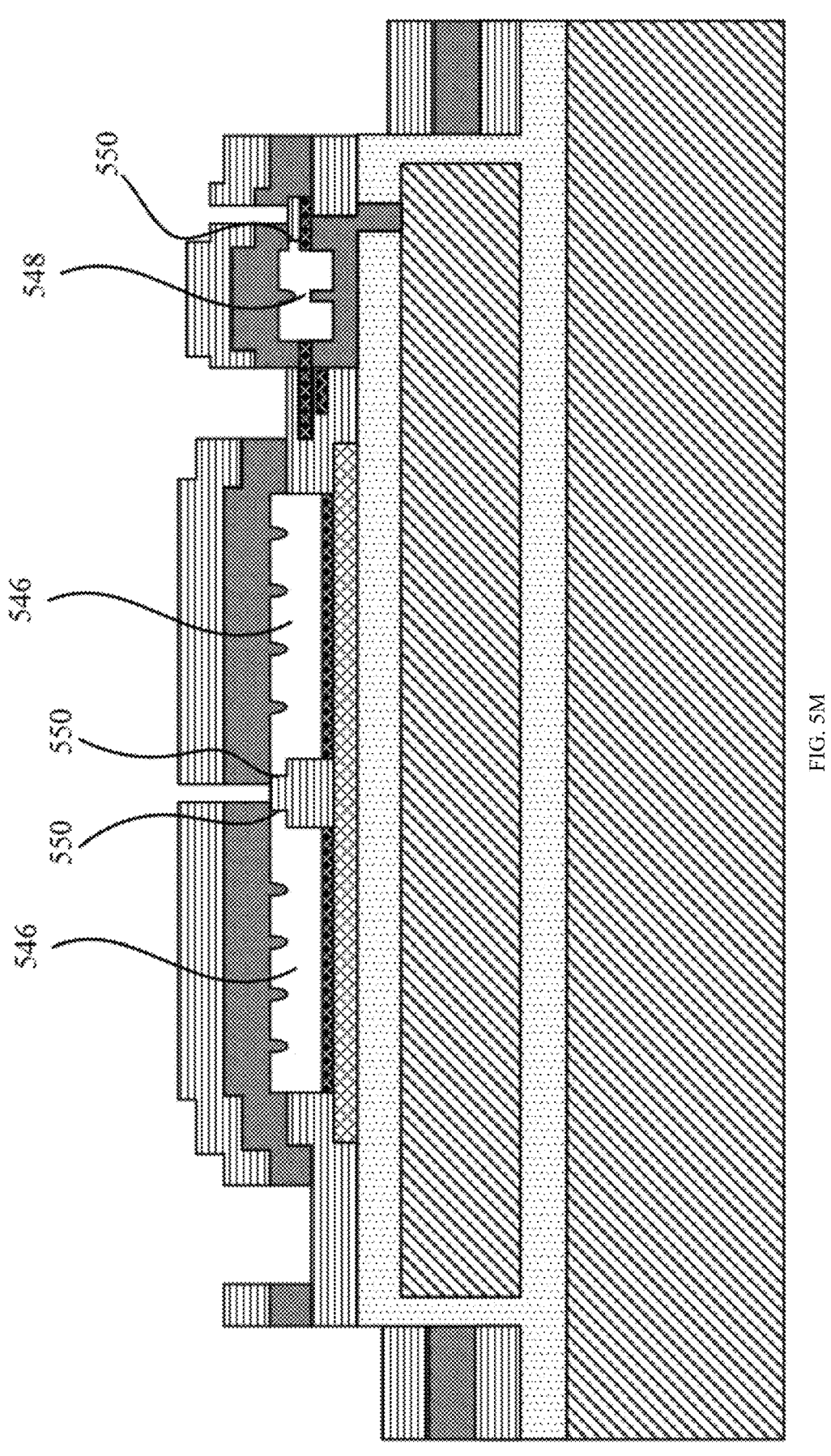
FIG. 5M shows the cross-sectional view of the structure after the third LTO deposition in which the sealing of the cavities is realized.

43) Removal of the sacrificial polysilicon in $XeF_2$ plasma as depicted in FIG. 5L.

The etch duration depends on the size of the CMUT cell and the lightning rod.

Sacrificial polysilicon 532 is etched away to create the CMUT cell cavity 546 and lightning rod cavity 548.

The bottom electrode 512 and the Faraday cage 506 are not etched because they are covered with silicon dioxide, and $XeF_2$ does not etch silicon dioxide (or very slowly etches) and diamond.

44) 200 nm thick fourth LTO layer deposition to provide the sealing of the CMUT cell cavity 546 and lightning rod cavity 548.

The CMUT cell cavity 546 and lightning rod cavity 548 are sealed from the opening of the etch channel 550.

LTO is not deposited inside the CMUT cell cavity 546 and the lightning rod cavity 548, since etch channels are labyrinth-shaped.

Figure 5N:
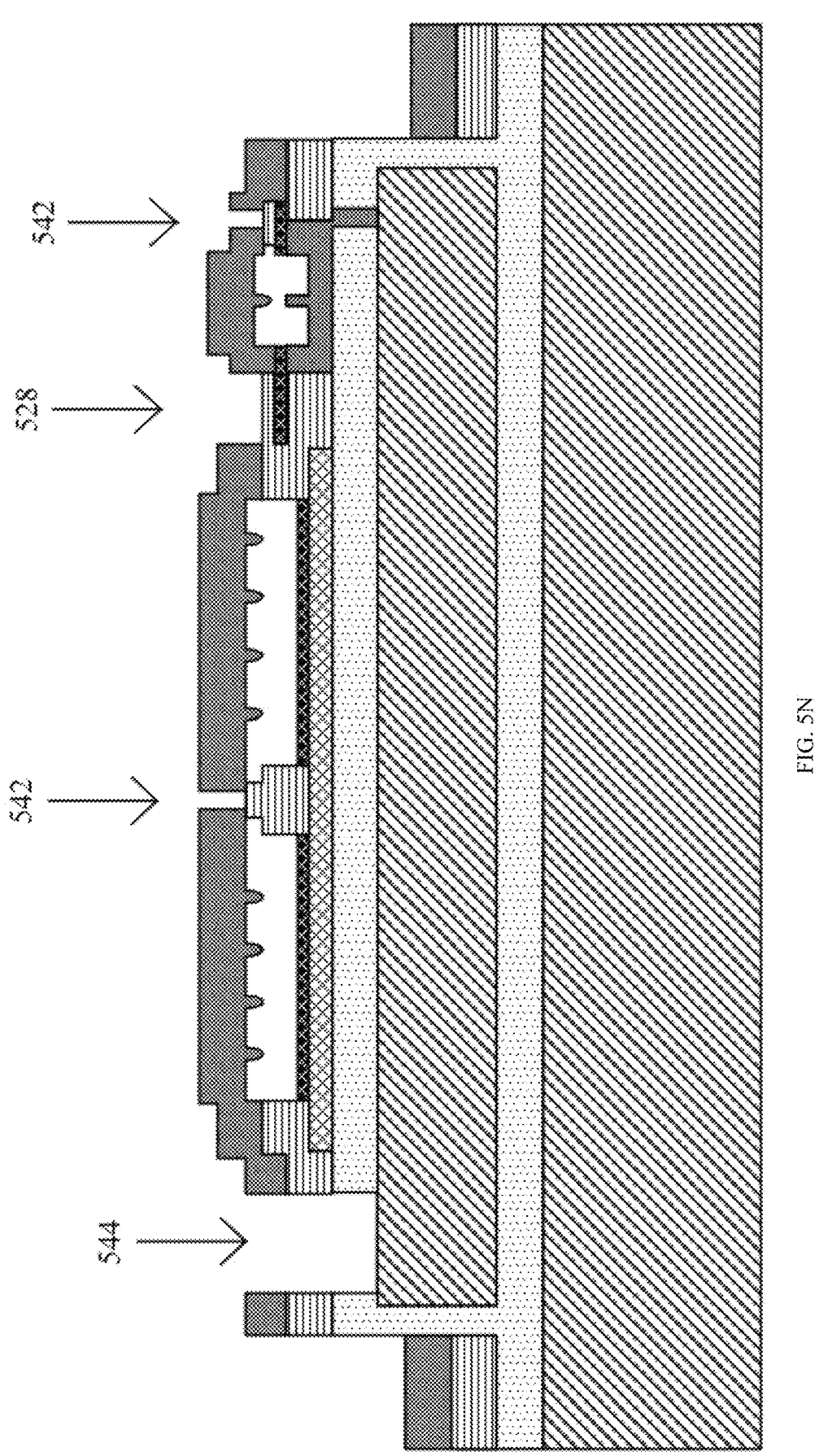
FIG. 5N shows the cross-sectional view of the structure after the removal of unnecessary silicon dioxide in HF based solution.
Figure 50:
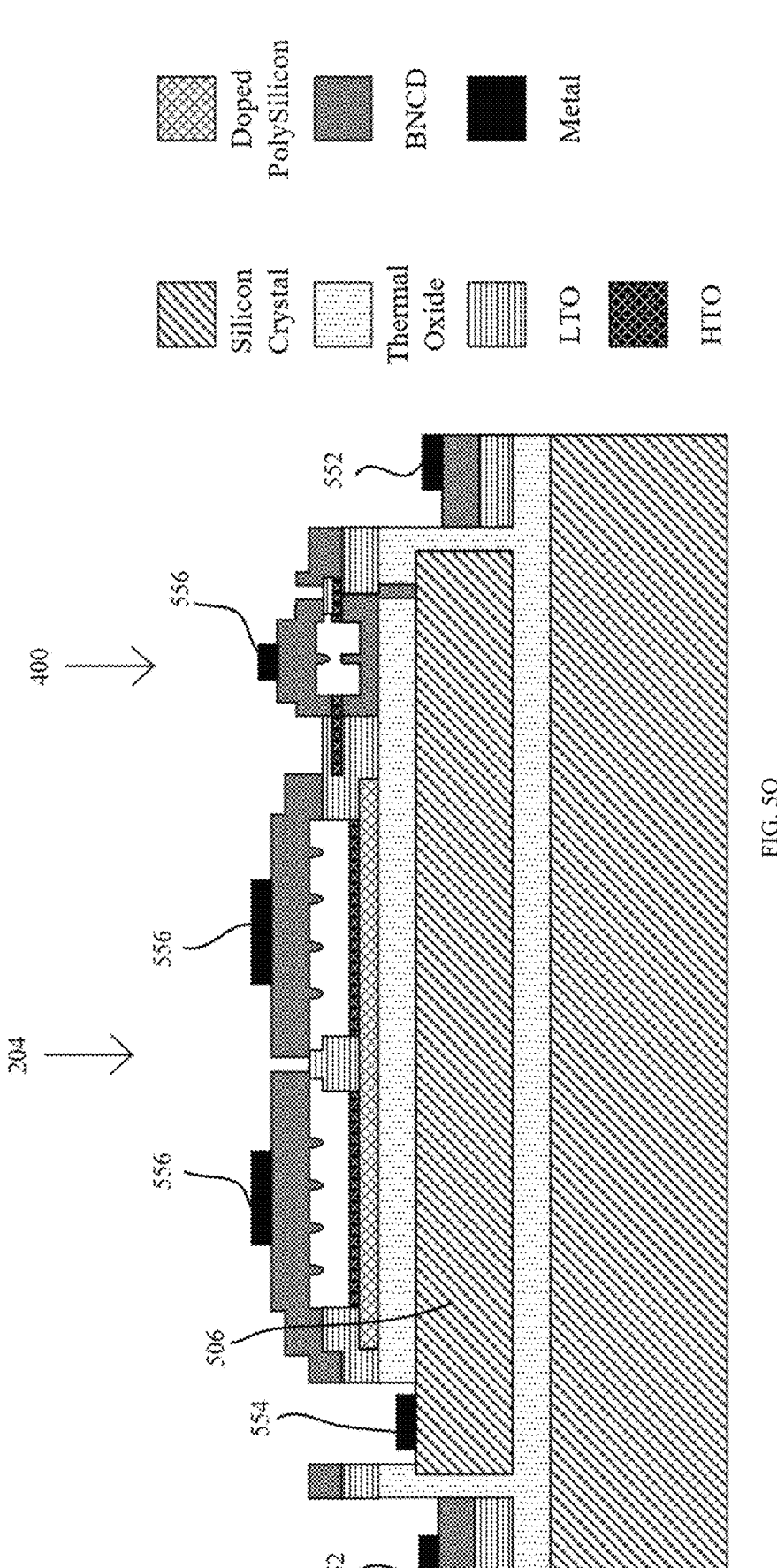

45) Removal of the unnecessary silicon dioxide with lithography and BHF as depicted in FIG. 5N.

Silicon dioxide underneath the diamond and polysilicon would not be etched away.

The photoresist is used to cover and prevent silicon dioxide in etch via 542 and the separation zone 528 between CMUT array and lightning rod from being etched.

Silicon dioxide remaining on top of the BNCD and inside the area of the metal pad connections 544 is etched away.

"Mask #12-Etch Via" mask is used during the exposure of the photoresist.

46) Metallization is performed as depicted in FIG. 5O.

Tri-metal (30 nm Titanium, 20 nm Copper, and 500 nm Gold) is evaporated on the wafer.

Patterning of this metal layer is performed by the metal lift-off technique.

The isolation line 552, in the separation zone between CMUT array elements 204, the third electrode 554 for the Faraday cage 506, the top electrode 556 of the CMUT cell, and the lightning rod are shown in FIG. 5O.

"Mask #13-Metal" mask is used during the exposure of the photoresist.

Annealing for the second, third and fourth LTO layers is not performed. The deposited second LTO layer (step 7) is the hard mask for diamond processing and is removed from the structure after diamond RIE (step 11). Since there is not any hot temperature process step between steps 7 and 11, annealing is not required. Also, after the third LTO layer (step 18) deposition, there is not any hot temperature process step, thus, annealing third and fourth LTO layers is not required.

For the HTO deposition (step 13), the recipe, developed by Bayram et al, is used since diamond is present in the structure during the HTO deposition [56,57].

Figure 6:
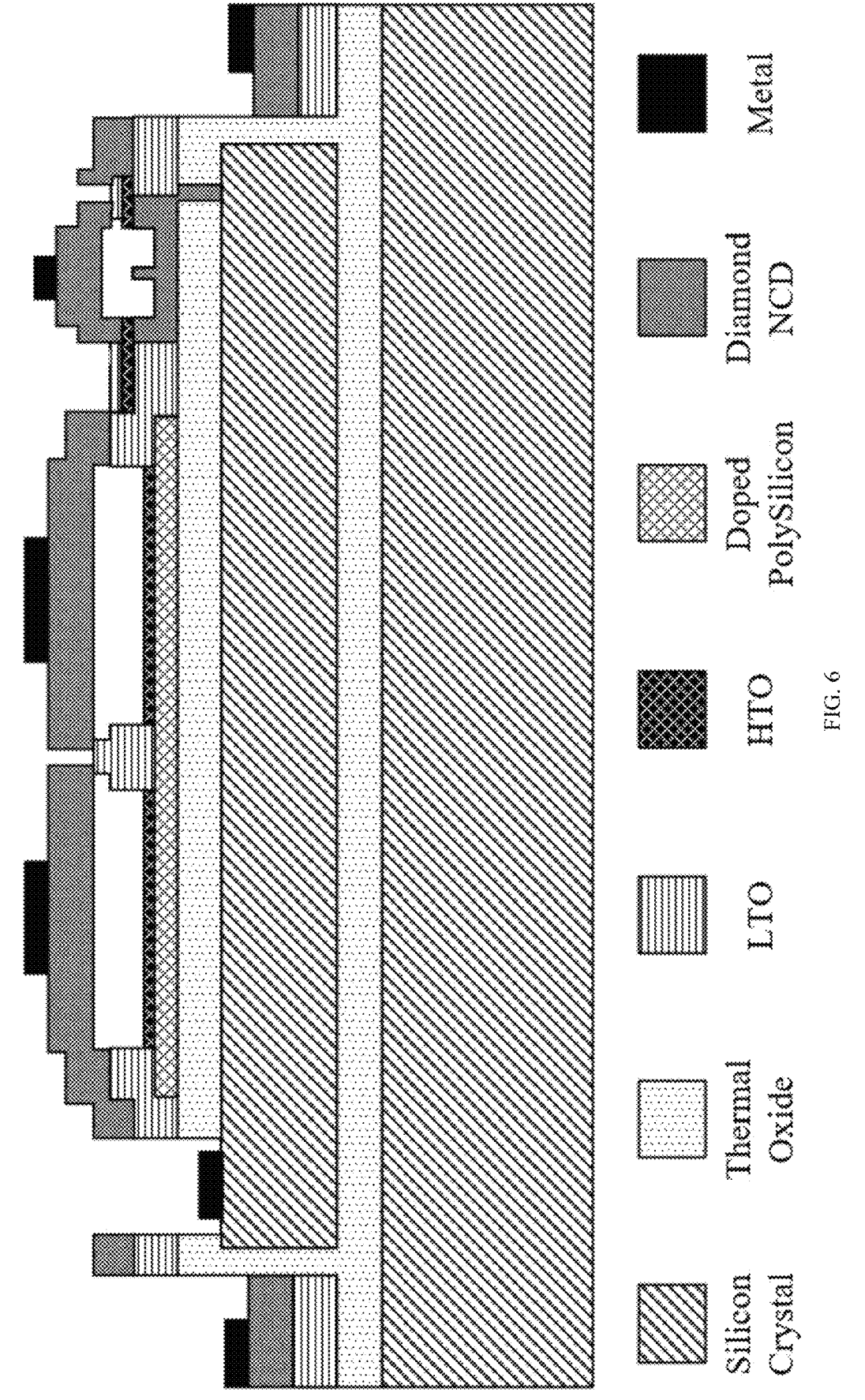
FIG. 6 shows the cross-sectional view of the structure without any dimples (alternate structure by skipping some of the original process steps).

FIG. 6 shows an alternative structure where there is no dimple 538. For this purpose, step 16 in the aforementioned process flow is skipped.

FEA tools of Semulator3D (Coventor, USA), ADS (Keysight, USA), and EMPro (Keysight, USA) were used to observe the capacitive behavior and the electrical crosstalk of the regular CMUT array and the Faraday Caged CMUT array. Simulations were performed for both regular and Faraday Caged CMUT arrays on a workstation (Dell Precision 5820, Dell Inc., USA) with Windows operating system.

Figure 7:
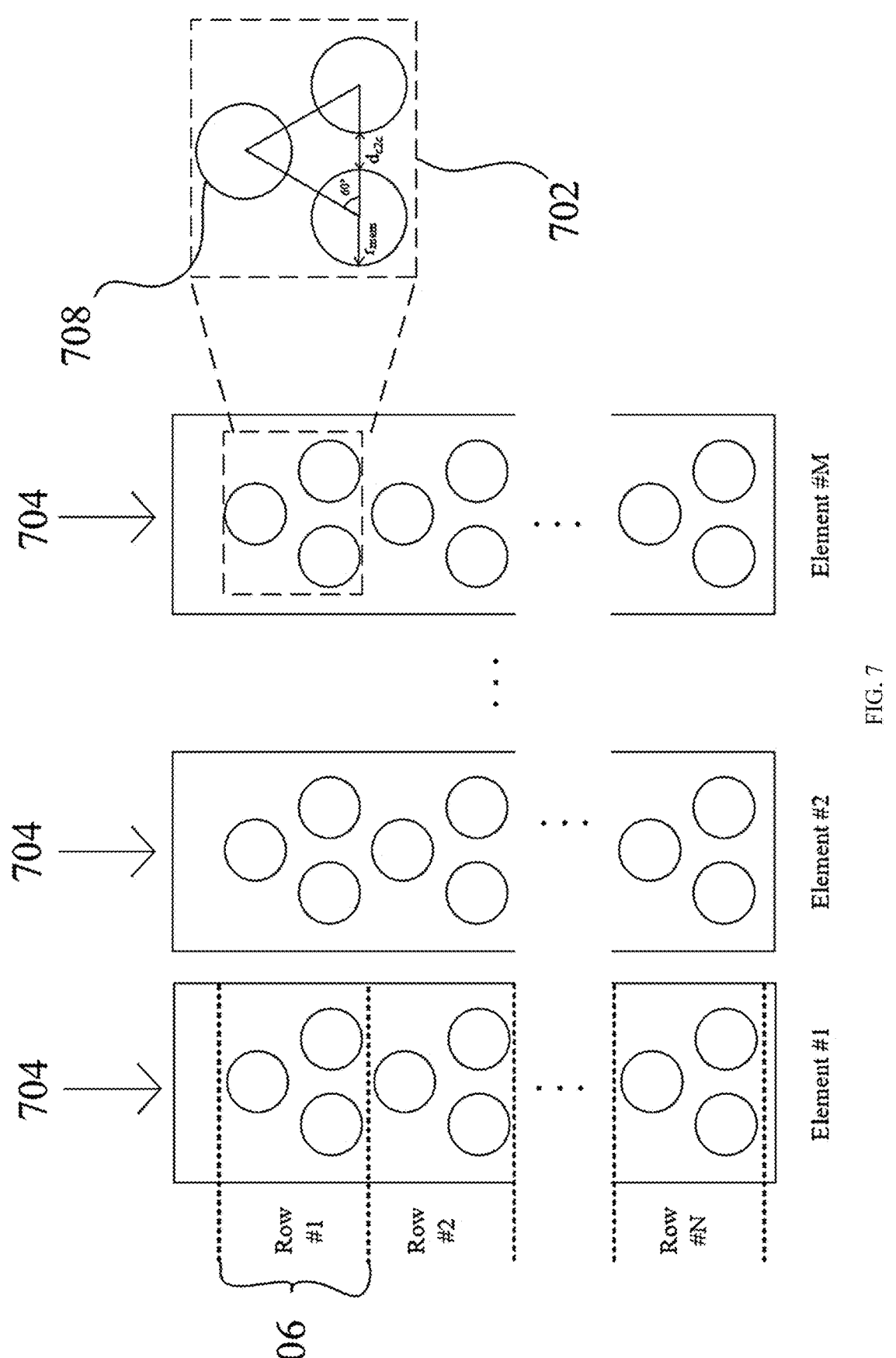
FIG. 7 shows the CMUT cell orientation and arrangement of elements in a CMUT array.

The CMUT cell orientation 702 for a 1-D M-element CMUT array is depicted in FIG. 7, wherein the CMUT array elements 704 are shown. The row number of the CMUT array determines the array height where a single row 706 includes three CMUT cells 708 in which, a CMUT cell can belong to only one row as shown in FIG. 7. This is a representative figure for 1-D CMUT array that is valid for regular and Faraday Caged CMUT arrays and was used as a base for the structures built in the computer environment. Some dimensions have been marked on FIG. 7; where $d_{C2C}$ is the cell to cell distance between CMUT cells 708, $r_{mem}$ is the radius of the circular shaped CMUT cells 708, $d_{A2A}$ is the element to element distance of CMUT arrays, and $w_A$ is the element width of the CMUT arrays.

Figure 8A:
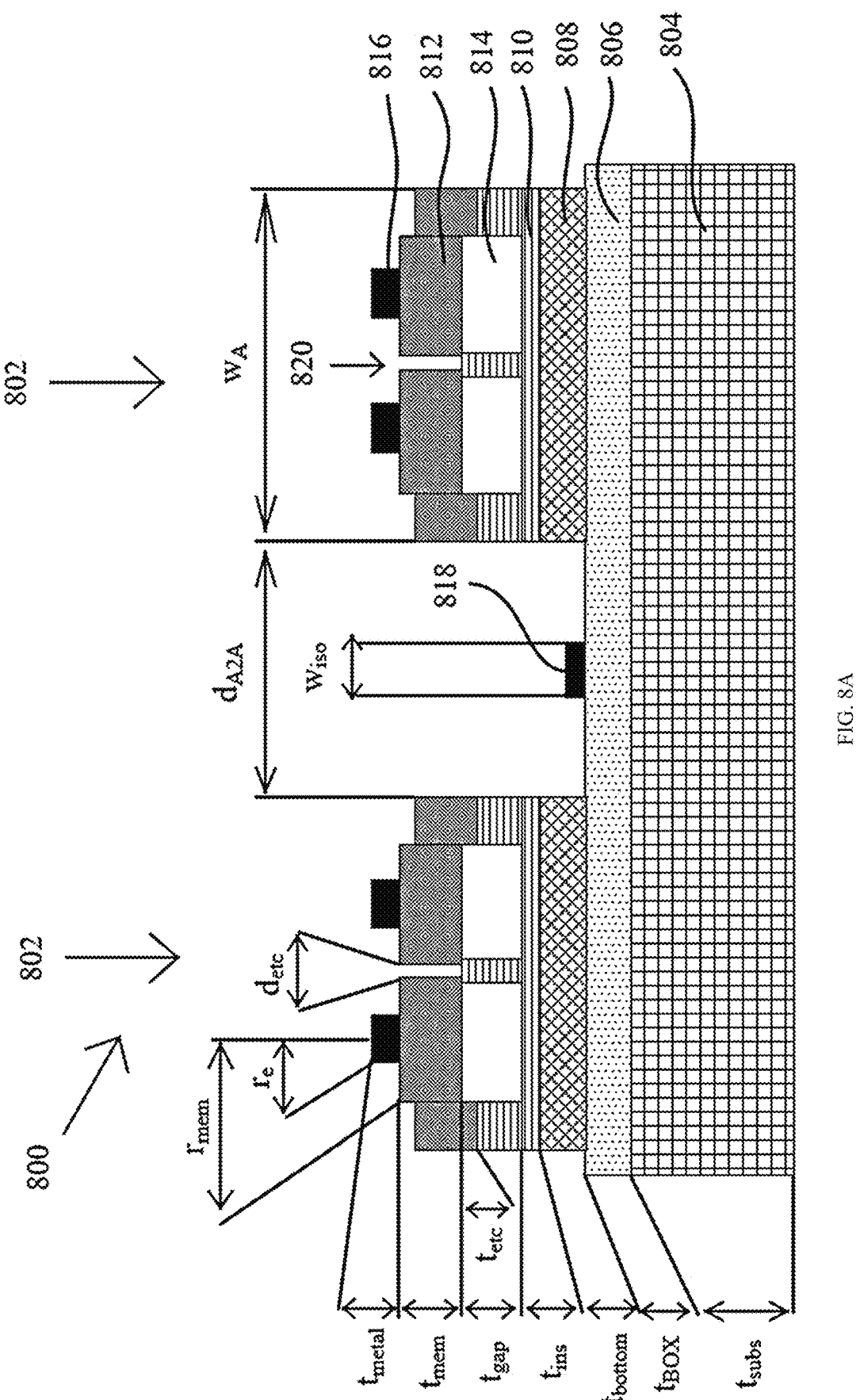
FIGS. 8A-8B show the structures built for regular and Faraday Caged CMUT arrays in computer environment.
Figure 8B:
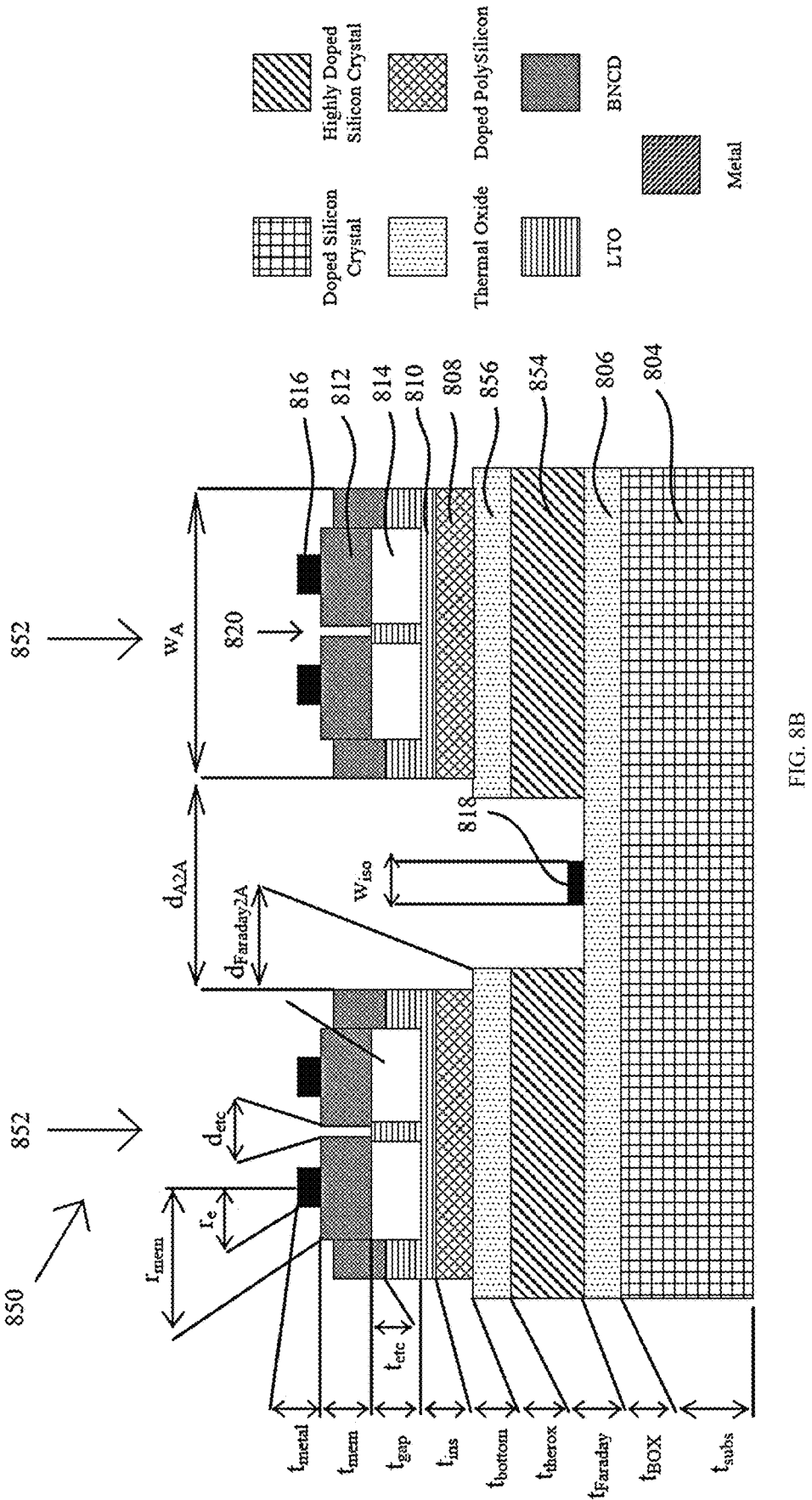

Some dimensions that are marked on the CMUT arrays depicted in FIGS. 8A-8B are also shown in FIG. 7 and have been explained above in detail. The regular CMUT array structure 800 built in the computer environment is depicted in FIG. 8A. The built structure of the regular CMUT array includes two array elements 802. Some dimensions have been marked on the CMUT array depicted in FIG. 8A where; $t_{subs}$ is the substrate 804 thickness, $t_{BOX}$ is the dielectric layer 806 thickness, $t_{bottom}$ is the bottom electrode 808, $t_{ins}$ is the insulator layer 810 thickness, $t_{gap}$ is the cavity gap 812 of the CMUT cell, $t_{etc}$ is the etch channel thickness, $t_{mem}$ is the membrane 814 thickness, $t_{metal}$ is the metal thickness, $r_e$ is the radius of the circular shaped top electrode 816 of the CMUT cell, $w_{iso}$ is the width of the isolation line 818, and $d_{etc}$ is the diameter of the circular shaped etch via 820.

The Faraday Caged CMUT array structure 850 built in the computer environment is as depicted in FIG. 8B. The built structure of the Faraday Caged CMUT array includes two array elements 852. All of the dimensions have been marked on Faraday Caged CMUT array structure as depicted in FIG. 8B. In addition to marked dimensions on regular CMUT array structure, some dimensions have been marked on the Faraday Caged CMUT array as depicted in FIG. 8B, where; $t_{Faraday}$ is the thickness of the Faraday Cage 854, $t_{therox}$ is the thickness of the thermally grown silicon dioxide layer 856 standing on top of the Faraday Cage 854 and $d_{Faraday2A}$ is the distance of Faraday cage border to the bottom electrode border.

Table I and II show the dimension parameter values and material properties of the built structures for regular and Faraday Caged CMUT arrays as depicted in FIGS. 7 and 8A-8B. Semulator3D lets users define a material as conductor and dielectric only, whereas, in ADS and EMPro, a material can be defined as conductor, semiconductor, and dielectric. Thus, the material definitions in these programs were slightly different from each other. This slight difference did not significantly affect the simulation results.

TABLE I

Dimension parameter values of the structures built for regular and Faraday Caged CMUT arrays in computer environment.

| Dimension parameter | Value (µm) |
|---|---|
| $t_{subs}$ | 400 |
| $t_{BOX}$ | 1 |
| $t_{Faraday}$ | 2 |
| $t_{therox}$ | 1 |
| $t_{bottom}$ | 1 |
| $t_{ins}$ | 0.15 |
| $t_{gap}$ | 1.1 |
| $t_{etc}$ | 0.25 |
| $t_{mem}$ | 1 |
| $t_{metal}$ | 0.5 |
| $r_{mem}$ | 18 |
| $r_e$ | 9 |
| $d_{etc}$ | 4 |
| $d_{C2C}$ | 7.3 |
| $d_{Faraday2A}$ | 2 |
| $d_{A2A}$ | 24 |
| $w_A$ | 116 |
| $w_{iso}$ | 10 |

TABLE II

Material definition and properties of the structures built for regular and Faraday Caged CMUT arrays in computer environment.

| | Semulator3D | | | ADS/EMPro | | |
|---|---|---|---|---|---|---|
| | Type | Conductivity (Siemens/m) | Dielectric Constant | Type | Conductivity (Siemens/m) | Dielectric Constant |
| Gold | Conductor | $4.1 \times 10^7$ | — | Conductor | $4.1 \times 10^7$ | — |
| PolySilicon | Conductor | $5.0 \times 10^4$ | — | Conductor | $5.0 \times 10^4$ | — |
| LTO | Dielectric | — | 4.3 | Dielectric | — | 4.3 |
| Thermal Silicon Dioxide | Dielectric | — | 3.9 | Dielectric | — | 3.9 |
| BNCD | Conductor | $5.0 \times 10^3$ | — | Semicond. | $5.0 \times 10^3$ | 5.5 |
| Highly Doped Silicon Crystal | Conductor | $2.0 \times 10^4$ | — | Semicond. | $2.0 \times 10^4$ | 11.9 |

TABLE II-continued

| Material definition and properties of the structures built for regular and Faraday Caged CMUT arrays in computer environment. | | | | | |
|---|---|---|---|---|---|
| | Semulator3D | | | ADS/EMPro | |
| Type | Conductivity (Siemens/m) | Dielectric Constant | Type | Conductivity (Siemens/m) | Dielectric Constant |
| Doped Silicon Crystal | Conductor | 20 | — | Semicond. | 20 | 11.9 |

Semulator3D (Coventor, USA) was used for virtual microfabrication of the structures of regular and Faraday Caged CMUT arrays as depicted in FIGS. 7 and 8A-8B in a computer environment, and then the capacitances were extracted between each node found in the 2-element regular and Faraday Caged CMUT arrays when row number is one, two, and three.

The 2-element regular CMUT array contains 6 nodes which are, the bottom electrode of the first array element (Array1 Signal), the top electrode of the first array element (Array1 Ground), the bottom electrode of the second array element (Array2 Signal), the top electrode of the second array element (Array 2 Ground), the isolation line (Isolation) and the substrate (Silicon Wafer). The capacitance matrices that include the capacitances between each node of the 2-element regular CMUT array when row number is one, two, and three are given in Tables III-V, respectively.

TABLE III

| Capacitance matrix of the regular CMUT array when row number is 1. | | | | | | |
|---|---|---|---|---|---|---|
| Node Names | Array1 Signal (pF) | Array1 Ground (pF) | Array2 Signal (pF) | Array2 Ground (pF) | Isolation (pF) | Silicon Wafer (pF) |
| Array1 Signal | | 6.81E−1 | 5.62E−8 | 4.54E−7 | 2.81E−4 | 7.45E−1 |
| Array1 Ground | 6.81E−1 | | 4.49E−7 | 3.61E−6 | 1.67E−3 | 3.39E−3 |
| Array2 Signal | 5.62E−8 | 4.49E−7 | | 6.81E−1 | 2.80E−4 | 7.45E−1 |
| Array2 Ground | 4.54E−7 | 3.61E−6 | 6.81E−1 | | 1.67E−3 | 3.40E−3 |
| Isolation | 2.81E−4 | 1.67E−3 | 2.80E−4 | 1.67E−3 | | 4.47E−1 |
| Silicon Wafer | 7.45E−1 | 3.39E−3 | 7.45E−1 | 3.40E−3 | 4.47E−1 | |

TABLE IV

| Capacitance matrix of the regular CMUT array when row number is 2. | | | | | | |
|---|---|---|---|---|---|---|
| Node Names | Array1 Signal (pF) | Array1 Ground (pF) | Array2 Signal (pF) | Array2 Ground (pF) | Isolation (pF) | Silicon Wafer (pF) |
| Array1 Signal | | 9.42E−1 | 8.37E−7 | 4.68E−6 | 1.07 | 4.62E−6 |
| Array1 Ground | 9.42E−1 | | 4.61E−6 | 2.60E−5 | 3.61E−3 | 2.55E−5 |
| Array2 Signal | 8.37E−7 | 4.61E−6 | | 9.42E−1 | 4.58E−6 | 1.07 |
| Array2 Ground | 4.68E−6 | 2.60E−5 | 9.42E−1 | | 2.56E−5 | 3.62E−3 |
| Isolation | 1.07 | 3.61E−3 | 4.58E−6 | 2.56E−5 | | 2.54E−5 |
| Silicon Wafer | 4.62E−6 | 2.55E−5 | 1.07 | 3.62E−3 | 2.54E−5 | |

TABLE V

Capacitance matrix of the regular CMUT array when row number is 3.

| Node Names | Array1 Signal (pF) | Array1 Ground (pF) | Array2 Signal (pF) | Array2 Ground (pF) | Isolation (pF) | Silicon Wafer (pF) |
|---|---|---|---|---|---|---|
| Array1 Signal | | 1.20 | 1.09E−6 | 6.15E−6 | 1.40 | 6.02E−6 |
| Array1 Ground | 1.20 | | 6.06E−6 | 3.40E−5 | 4.34E−3 | 3.33E−5 |
| Array2 Signal | 1.09E−6 | 6.06E−6 | | 1.20 | 5.97E−6 | 1.40 |
| Array2 Ground | 6.15E−6 | 3.40E−5 | 1.20 | | 3.34E−5 | 4.35E−3 |
| Isolation | 1.40 | 4.34E−3 | 5.97E−6 | 3.34E−5 | | 3.30E−5 |
| Silicon Wafer | 6.02E−6 | 3.33E−5 | 1.40 | 4.35E−3 | 3.30E−5 | |

The 2-element Faraday Caged CMUT array contains 8 nodes which are, the bottom electrode of the first array element (Array1 Signal), the top electrode of the first array element (Array1 Ground), the Faraday cage of the first array element (Array 1 Faraday Cage), the bottom electrode of the second array element (Array2 Signal), the top electrode of the second array element (Array 2 Ground), the Faraday cage of the second array element (Array 2 Faraday Cage), the isolation line (Isolation) and the substrate (Silicon Wafer). The capacitance matrices that include the capacitances between each node of the 2-element Faraday Caged CMUT array when row number is one, two, and three are given in Tables VI-VIII, respectively.

TABLE VI

Capacitance matrix of the Faraday Caged CMUT array when row number is 1.

| Node Names | Array1 Signal (pF) | Array1 Ground (pF) | Array2 Signal (pF) | Array2 Ground (pF) | Array1 Faraday Cage (pF) | Array2 Faraday Cage (pF) | Isolation (pF) | Silicon Wafer (pF) |
|---|---|---|---|---|---|---|---|---|
| Array1 Signal | | 6.81E−1 | 5.79E−7 | 3.25E−6 | 7.45E−1 | 3.21E−6 | 3.39E−4 | 1.78E−4 |
| Array1 Ground | 6.81E−1 | | 3.21E−6 | 1.80E−5 | 2.88E−3 | 1.78E−5 | 1.39E−3 | 3.52E−4 |
| Array2 Signal | 5.79E−7 | 3.21E−6 | | 6.36E−1 | 3.18E−6 | 7.45E−1 | 3.38E−4 | 1.77E−4 |
| Array2 Ground | 3.25E−6 | 1.80E−5 | 6.36E−1 | | 1.78E−5 | 2.89E−3 | 1.39E−3 | 3.53E−4 |
| Array1 Faraday Cage | 7.45E−1 | 2.88E−3 | 3.18E−6 | 1.78E−5 | | 1.78E−5 | 3.36E−3 | 7.56E−1 |
| Array2 Faraday Cage | 3.21E−6 | 1.78E−5 | 7.45E−1 | 2.89E−3 | 1.78E−5 | | 3.36E−3 | 7.56E−1 |
| Isolation | 3.39E−4 | 1.39E−3 | 3.38E−4 | 1.39E−3 | 3.36E−3 | 3.36E−3 | | 4.44E−1 |
| Silicon Wafer | 1.78E−4 | 3.52E−4 | 1.77E−4 | 3.53E−4 | 7.56E−1 | 7.56E−1 | 4.44E−1 | |

TABLE VII

Capacitance matrix of the Faraday Caged CMUT array when row number is 2.

| Node Names | Array1 Signal (pF) | Array1 Ground (pF) | Array2 Signal (pF) | Array2 Ground (pF) | Array1 Faraday Cage (pF) | Array2 Faraday Cage (pF) | Isolation (pF) | Silicon Wafer (pF) |
|---|---|---|---|---|---|---|---|---|
| Array1 Signal | | 9.42E−1 | 8.37E−7 | 4.68E−6 | 1.07 | 4.62E−6 | 4.23E−4 | 2.22E−4 |
| Array1 Ground | 9.42E−1 | | 4.61E−6 | 2.60E−5 | 3.61E−3 | 2.55E−5 | 1.73E−3 | 4.36E−4 |
| Array2 Signal | 8.37E−7 | 4.61E−6 | | 9.42E−1 | 4.58E−6 | 1.07 | 4.21E−4 | 2.21E−4 |
| Array2 Ground | 4.68E−6 | 2.60E−5 | 9.42E−1 | | 2.56E−5 | 3.62E−3 | 1.74E−3 | 4.37E−4 |

TABLE VII-continued

| Node Names | Array1 Signal (pF) | Array1 Ground (pF) | Array2 Signal (pF) | Array2 Ground (pF) | Array1 Faraday Cage (pF) | Array2 Faraday Cage (pF) | Isolation (pF) | Silicon Wafer (pF) |
|---|---|---|---|---|---|---|---|---|
| | | | Capacitance matrix of the Faraday Caged CMUT array when row number is 2. | | | | | |
| Array1 Faraday Cage | 1.07 | 3.61E−3 | 4.58E−6 | 2.56E−5 | | 2.54E−5 | 4.17E−3 | 1.08 |
| Array2 Faraday Cage | 4.62E−6 | 2.55E−5 | 1.07 | 3.62E−3 | 2.54E−5 | | 4.18E−3 | 1.08 |
| Isolation | 4.23E−4 | 1.73E−3 | 4.21E−4 | 1.74E−3 | 4.17E−3 | 4.18E−3 | | 5.32E−1 |
| Silicon Wafer | 2.22E−4 | 4.36E−4 | 2.21E−4 | 4.37E−4 | 1.08 | 1.08 | 5.32E−1 | |

TABLE VIII

| Node Names | Array1 Signal (pF) | Array1 Ground (pF) | Array2 Signal (pF) | Array2 Ground (pF) | Array1 Faraday Cage (pF) | Array2 Faraday Cage (pF) | Isolation (pF) | Silicon Wafer (pF) |
|---|---|---|---|---|---|---|---|---|
| | | | Capacitance matrix of the Faraday Caged CMUT array when row number is 3. | | | | | |
| Array1 Signal | | 1.20 | 1.09E−6 | 6.15E−6 | 1.40 | 6.02E−6 | 5.07E−4 | 2.66E−4 |
| Array1 Ground | 1.20 | | 6.06E−6 | 3.40E−5 | 4.34E−3 | 3.33E−5 | 2.08E−3 | 5.19E−4 |
| Array2 Signal | 1.09E−6 | 6.06E−6 | | 1.20 | 5.97E−6 | 1.40 | 5.04E−4 | 2.65E−4 |
| Array2 Ground | 6.15E−6 | 3.40E−5 | 1.20 | | 3.34E−5 | 4.35E−3 | 2.08E−3 | 5.20E−4 |
| Array1 Faraday Cage | 1.40 | 4.34E−3 | 5.97E−6 | 3.34E−5 | | 3.30E−5 | 4.99E−3 | 1.40 |
| Array2 Faraday Cage | 6.02E−6 | 3.33E−5 | 1.40 | 4.35E−3 | 3.30E−5 | | 4.99E−3 | 1.40 |
| Isolation | 5.07E−4 | 2.08E−3 | 5.04E−4 | 2.08E−3 | 4.99E−3 | 4.99E−3 | | 6.19E−1 |
| Silicon Wafer | 2.66E−4 | 5.19E−4 | 2.65E−4 | 5.20E−4 | 1.40 | 1.40 | 6.19E−1 | |

Due to computational complexity, the extraction of the capacitance matrix of the structures with high row number value was not feasible in Semulator3D. Thus, the linearity of the capacitive matrices of the regular and Faraday Caged CMUT arrays was examined. For this purpose, the capacitance matrices of regular and Faraday Cage CMUT arrays were extrapolated when row number is three based on the results of the capacitance matrices when row number is one and two. Then the extrapolated matrices were compared with the extracted capacitance matrix of the corresponding CMUT array when row number is three. The linearity examination of the capacitances between each node in regular and Faraday Caged CMUT arrays are given in Tables IX and X, respectively. $C_E$ represents the extrapolated capacitance value, whereas $C_3$ represents the extracted capacitance value.

TABLE IX

| Net Names | | Array1 Signal (pF) | Array1 Ground (pF) | Array2 Signal (pF) | Array2 Ground (pF) | Isolation (pF) | Silicon Wafer (pF) |
|---|---|---|---|---|---|---|---|
| | | | Linearity examination of the capacitances found in regular CMUT array. | | | | |
| Array1 Signal | $C_E$ | | 1.20 | 1.06E−7 | 8.60E−7 | 4.20E−4 | 1.40 |
| | $C_3$ | | 1.20 | 1.06E−7 | 8.57E−7 | 4.20E−4 | 1.40 |
| | | | Linear | Linear | ~Linear | Linear | Linear |
| Array1 Ground | $C_E$ | 1.20 | | 8.57E−7 | 6.81E−6 | 2.50E−3 | 5.10E−3 |
| | $C_3$ | 1.20 | | 8.50E−7 | 6.85E−6 | 2.50E−3 | 5.10E−3 |
| | | Linear | | ~Linear | ~Linear | Linear | Linear |
| Array2 Signal | $C_E$ | 1.06E−7 | 8.57E−7 | | 1.20 | 4.19E−4 | 1.40 |
| | $C_3$ | 1.06E−7 | 8.50E−7 | | 1.20 | 4.19E−4 | 1.40 |
| | | Linear | ~Linear | | Linear | Linear | Linear |

TABLE IX-continued

Linearity examination of the capacitances found in regular CMUT array.

| Net Names | | Array1 Signal (pF) | Array1 Ground (pF) | Array2 Signal (pF) | Array2 Ground (pF) | Isolation (pF) | Silicon Wafer (pF) |
|---|---|---|---|---|---|---|---|
| Array2 Ground | $C_E$ | 8.60E−7 | 6.81E−6 | 1.20 | | 2.50E−3 | 5.11E−3 |
| | $C_3$ | 8.57E−7 | 6.85E−6 | 1.20 | | 2.50E−3 | 5.11E−3 |
| | | ~Linear | ~Linear | Linear | | Linear | Linear |
| Isolation | $C_E$ | 4.20E−4 | 2.50E−3 | 4.19E−4 | 2.50E−3 | | 6.24E−1 |
| | $C_3$ | 4.20E−4 | 2.50E−3 | 4.19E−4 | 2.50E−3 | | 6.24E−1 |
| | | Linear | Linear | Linear | Linear | | Linear |
| Silicon Wafer | $C_E$ | 1.40 | 5.10E−3 | 1.40 | 5.11E−3 | 6.24E−1 | |
| | $C_3$ | 1.40 | 5.10E−3 | 1.40 | 5.11E−3 | 6.24E−1 | |
| | | Linear | Linear | Linear | Linear | Linear | |

TABLE X

Linearity examination of the capacitances found in Faraday Caged CMUT array.

| Net Names | | Array1 Signal (pF) | Array1 Ground (pF) | Array2 Signal (pF) | Array2 Ground (pF) | Array1 Faraday Cage (pF) | Array2 Faraday Cage (pF) | Isolation (pF) | Silicon Wafer (pF) |
|---|---|---|---|---|---|---|---|---|---|
| Array1 Signal | $C_E$ | | 1.20 | 1.09E−6 | 6.15E−6 | 1.40 | 6.02E−6 | 5.07E−4 | 2.66E−4 |
| | $C_3$ | | 1.20 | 1.09E−6 | 6.15E−6 | 1.40 | 6.02E−6 | 5.07E−4 | 2.66E−4 |
| | | | Linear | Linear | Linear | Linear | Linear | Linear | Linear |
| Array1 Ground | $C_E$ | 1.20 | | 6.06E−6 | 3.40E−5 | 4.34E−3 | 3.33E−5 | 2.08E−3 | 5.19E−4 |
| | $C_3$ | 1.20 | | 6.06E−6 | 3.40E−5 | 4.34E−3 | 3.33E−5 | 2.08E−3 | 5.19E−4 |
| | | Linear | | Linear | Linear | Linear | Linear | Linear | Linear |
| Array2 Signal | $C_E$ | 1.09E−6 | 6.06E−6 | | 1.20 | 5.97E−6 | 1.40 | 5.04E−4 | 2.65E−4 |
| | $C_3$ | 1.09E−6 | 6.06E−6 | | 1.20 | 5.97E−6 | 1.40 | 5.04E−4 | 2.65E−4 |
| | | Linear | Linear | | Linear | Linear | Linear | Linear | Linear |
| Array2 Ground | $C_3$ | 6.15E−6 | 3.40E−5 | 1.20 | | 3.34E−5 | 4.35E−3 | 2.08E−3 | 5.20E−4 |
| | $C_3$ | 6.15E−6 | 3.40E−5 | 1.20 | | 3.34E−5 | 4.35E−3 | 2.08E−3 | 5.20E−4 |
| | | Linear | Linear | Linear | | Linear | Linear | Linear | Linear |
| Array1 Faraday Cage | $C_E$ | 1.40 | 4.34E−3 | 5.97E−6 | 3.34E−5 | | 3.30E−5 | 4.99E−3 | 1.40 |
| | $C_3$ | 1.40 | 4.34E−3 | 5.97E−6 | 3.34E−5 | | 3.30E−5 | 4.99E−3 | 1.40 |
| | | Linear | Linear | Linear | Linear | | Linear | Linear | Linear |
| Array2 Faraday Cage | $C_E$ | 6.02E−6 | 3.33E−5 | 1.40 | 4.35E−3 | 3.30E−5 | | 4.99E−3 | 1.40 |
| | $C_3$ | 6.02E−6 | 3.33E−5 | 1.40 | 4.35E−3 | 3.30E−5 | | 4.99E−3 | 1.40 |
| | | Linear | Linear | Linear | Linear | Linear | | Linear | Linear |
| Isolation | $C_E$ | 5.07E−4 | 2.08E−3 | 5.04E−4 | 2.08E−3 | 4.99E−3 | 4.99E−3 | | 6.19E−1 |
| | $C_3$ | 5.07E−4 | 2.08E−3 | 5.04E−4 | 2.08E−3 | 4.99E−3 | 4.99E−3 | | 6.19E−1 |
| | | Linear | Linear | Linear | Linear | Linear | Linear | | Linear |
| Silicon Wafer | $C_3$ | 2.66E−4 | 5.19E−4 | 2.65E−4 | 5.20E−4 | 1.40 | 1.40 | 6.19E−1 | |
| | $C_3$ | 2.66E−4 | 5.19E−4 | 2.65E−4 | 5.20E−4 | 1.40 | 1.40 | 6.19E−1 | |
| | | Linear | Linear | Linear | Linear | Linear | Linear | Linear | |

It is observed that all of the capacitances found in 2-element regular and Faraday Caged CMUT arrays are linear, as depicted in Tables IX-X. Thus, it is possible to extrapolate the capacitance matrix of regular and Faraday Cage CMUT arrays for high row number cases. The capacitance matrix of regular and Faraday Caged CMUT arrays when the row number is 10 were extrapolated as depicted in Table XI and XII, respectively.

TABLE XI

Extrapolated capacitance matrix of the regular CMUT array when the row number is 10.

| Node Names | Array1 Signal (pF) | Array1 Ground (pF) | Array2 Signal (pF) | Array2 Ground (pF) | Isolation (pF) | Silicon Wafer (pF) |
|---|---|---|---|---|---|---|
| Array1 Signal | | 3.03 | 2.82E−7 | 2.28E−6 | 9.08E−4 | 3.68 |
| Array1 Ground | 3.03 | | 2.28E−6 | 1.80E−5 | 5.41E−3 | 1.11E−2 |
| Array2 Signal | 2.82E−7 | 2.28E−6 | | 3.03 | 9.04E−4 | 3.68 |
| Array2 Ground | 2.28E−6 | 1.80E−5 | 3.03 | | 5.42E−3 | 1.11E−2 |

TABLE XI-continued

| | Array1 Signal (pF) | Array1 Ground (pF) | Array2 Signal (pF) | Array2 Ground (pF) | Isolation (pF) | Silicon Wafer (pF) |
|---|---|---|---|---|---|---|
| Node Names | | | | | | |
| Isolation | 9.08E−4 | 5.41E−3 | 9.04E−4 | 5.42E−3 | | 1.24 |
| Silicon Wafer | 3.68 | 1.11E−2 | 3.68 | 1.11E−2 | 1.24 | |

Extrapolated capacitance matrix of the regular
CMUT array when the row number is 10.

TABLE XII

Extrapolated capacitance matrix of the Faraday Caged CMUT array when the row number is 10.

| Node Names | Array1 Signal (pF) | Array1 Ground (pF) | Array2 Signal (pF) | Array2 Ground (pF) | Array1 Faraday Cage (pF) | Array2 Faraday Cage (pF) | Isolation (pF) | Silicon Wafer (pF) |
|---|---|---|---|---|---|---|---|---|
| Array1 Signal | | 3.03 | 2.82E−7 | 2.28E−6 | 9.08E−4 | 3.68 | | 3.03 |
| Array1 Ground | 3.03 | | 2.28E−6 | 1.80E−5 | 5.41E−3 | 1.11E−2 | 3.03 | |
| Array2 Signal | 2.82E−7 | 2.28E−6 | | 3.03 | 9.04E−4 | 3.68 | 2.82E−7 | 2.28E−6 |
| Array2 Ground | 2.28E−6 | 1.80E−5 | 3.03 | | 5.42E−3 | 1.11E−2 | 2.28E−6 | 1.80E−5 |
| Array1 Faraday Cage | 9.08E−4 | 5.41E−3 | 9.04E−4 | 5.42E−3 | | 1.24 | 9.08E−4 | 5.41E−3 |
| Array2 Faraday Cage | 3.68 | 1.11E−2 | 3.68 | 1.11E−2 | 1.24 | | 3.68 | 1.11E−2 |
| Isolation | | 3.03 | 2.82E−7 | 2.28E−6 | 9.08E−4 | 3.68 | | 3.03 |
| Silicon Wafer | 3.03 | | 2.28E−6 | 1.80E−5 | 5.41E−3 | 1.11E−2 | 3.03 | |

For a high row number value, the capacitive behavior of regular and Faraday Cage CMUT arrays had been examined to compare the characteristics of the CMUT arrays regardless of the row number. For this purpose, the capacitance matrices of the arrays with a high row number value were extrapolated as given in Tables XIII and XIV, respectively.

TABLE XIII

Extrapolated capacitance matrix of the regular
CMUT array with a high row number value (N).

| Node Names | Array1 Signal (×N pF) | Array1 Ground (×N pF) | Array2 Signal (×N pF) | Array2 Ground (×N pF) | Isolation (×N pF) | Silicon Wafer (×N pF) |
|---|---|---|---|---|---|---|
| Array1 Signal | | 2.61E−1 | 2.51E−9 | 2.03E−7 | 6.97E−5 | 3.26E−1 |
| Array1 Ground | 2.61E−1 | | 2.04E−7 | 1.60E−6 | 4.16E−4 | 8.54E−4 |
| Array2 Signal | 2.51E−9 | 2.04E−7 | | 2.61E−1 | 6.93E−5 | 3.26E−1 |
| Array2 Ground | 2.03E−7 | 1.60E−6 | 2.61E−1 | | 4.17E−4 | 8.57E−4 |
| Isolation | 6.97E−5 | 4.16E−4 | 6.93E−5 | 4.17E−4 | | 8.83E−2 |
| Silicon Wafer | 3.26E−1 | 8.54E−4 | 3.26E−1 | 8.57E−4 | 8.83E−2 | |

TABLE XIV

| Node Names | Array1 Signal (×N pF) | Array1 Ground (×N pF) | Array2 Signal (×N pF) | Array2 Ground (×N pF) | Array1 Faraday Cage (×N pF) | Array2 Faraday Cage (×N pF) | Isolation (×N pF) | Silicon Wafer (×N pF) |
|---|---|---|---|---|---|---|---|---|
| | | | | | | | | |
| Extrapolated capacitance matrix of the Faraday Caged CMUT array with a high row number value (N). | | | | | | | | |
| Array1 Signal | | 6.81E−1 | 5.79E−7 | 3.25E−6 | 7.45E−1 | 3.21E−6 | 3.39E−4 | 1.78E−4 |
| Array1 Ground | 6.81E−1 | | 3.21E−6 | 1.80E−5 | 2.88E−3 | 1.78E−5 | 1.39E−3 | 3.52E−4 |
| Array2 Signal | 5.79E−7 | 3.21E−6 | | 6.36E−1 | 3.18E−6 | 7.45E−1 | 3.38E−4 | 1.77E−4 |
| Array2 Ground | 3.25E−6 | 1.80E−5 | 6.36E−1 | | 1.78E−5 | 2.89E−3 | 1.39E−3 | 3.53E−4 |
| Array1 Faraday Cage | 7.45E−1 | 2.88E−3 | 3.18E−6 | 1.78E−5 | | 1.78E−5 | 3.36E−3 | 7.56E−1 |
| Array2 Faraday Cage | 3.21E−6 | 1.78E−5 | 7.45E−1 | 2.89E−3 | 1.78E−5 | | 3.36E−3 | 7.56E−1 |
| Isolation | 3.39E−4 | 1.39E−3 | 3.38E−4 | 1.39E−3 | 3.36E−3 | 3.36E−3 | | 4.44E−1 |
| Silicon Wafer | 1.78E−4 | 3.52E−4 | 1.77E−4 | 3.53E−4 | 7.56E−1 | 7.56E−1 | 4.44E−1 | |

Figure 9A:
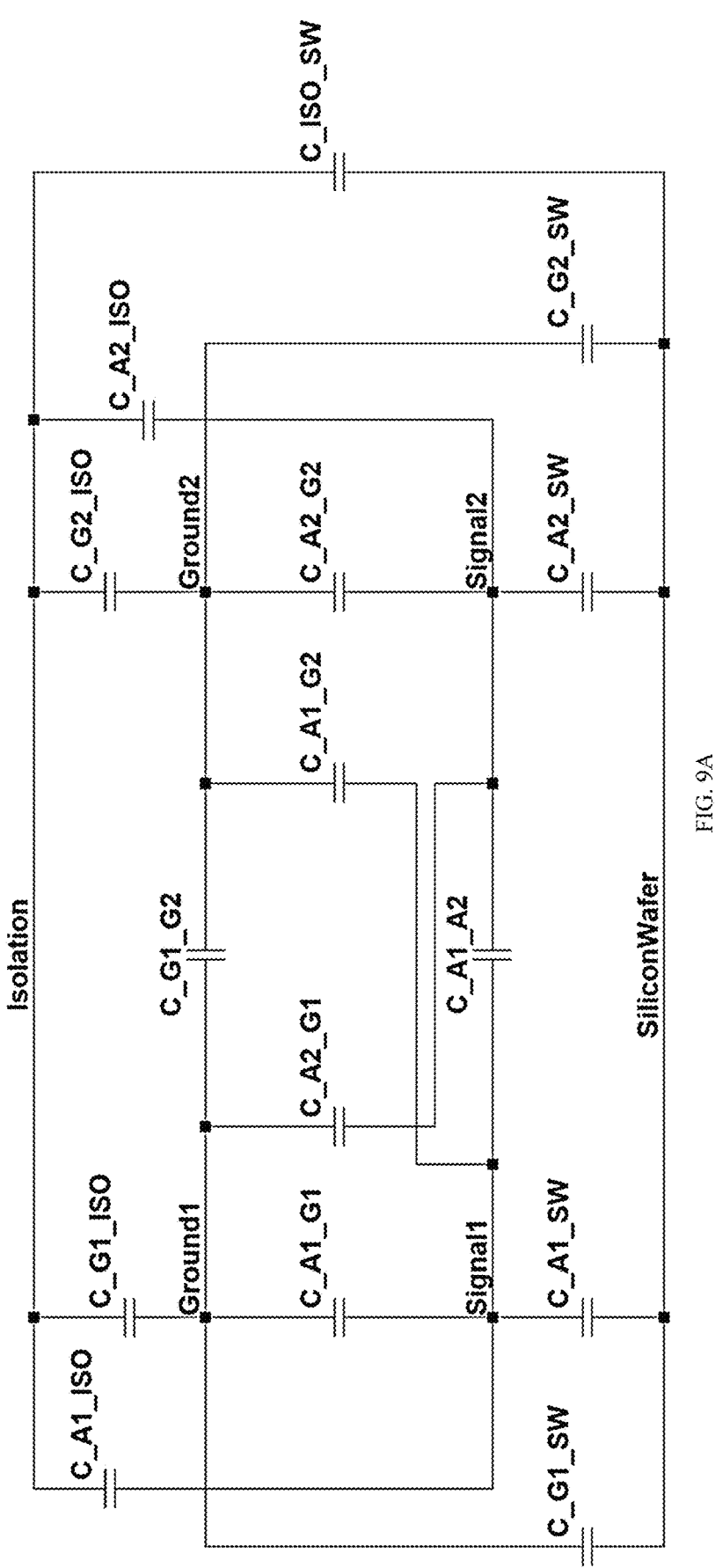
FIGS. 9A-9B show the capacitance circuitries of the 2-element regular CMUT array.
Figure 9B:
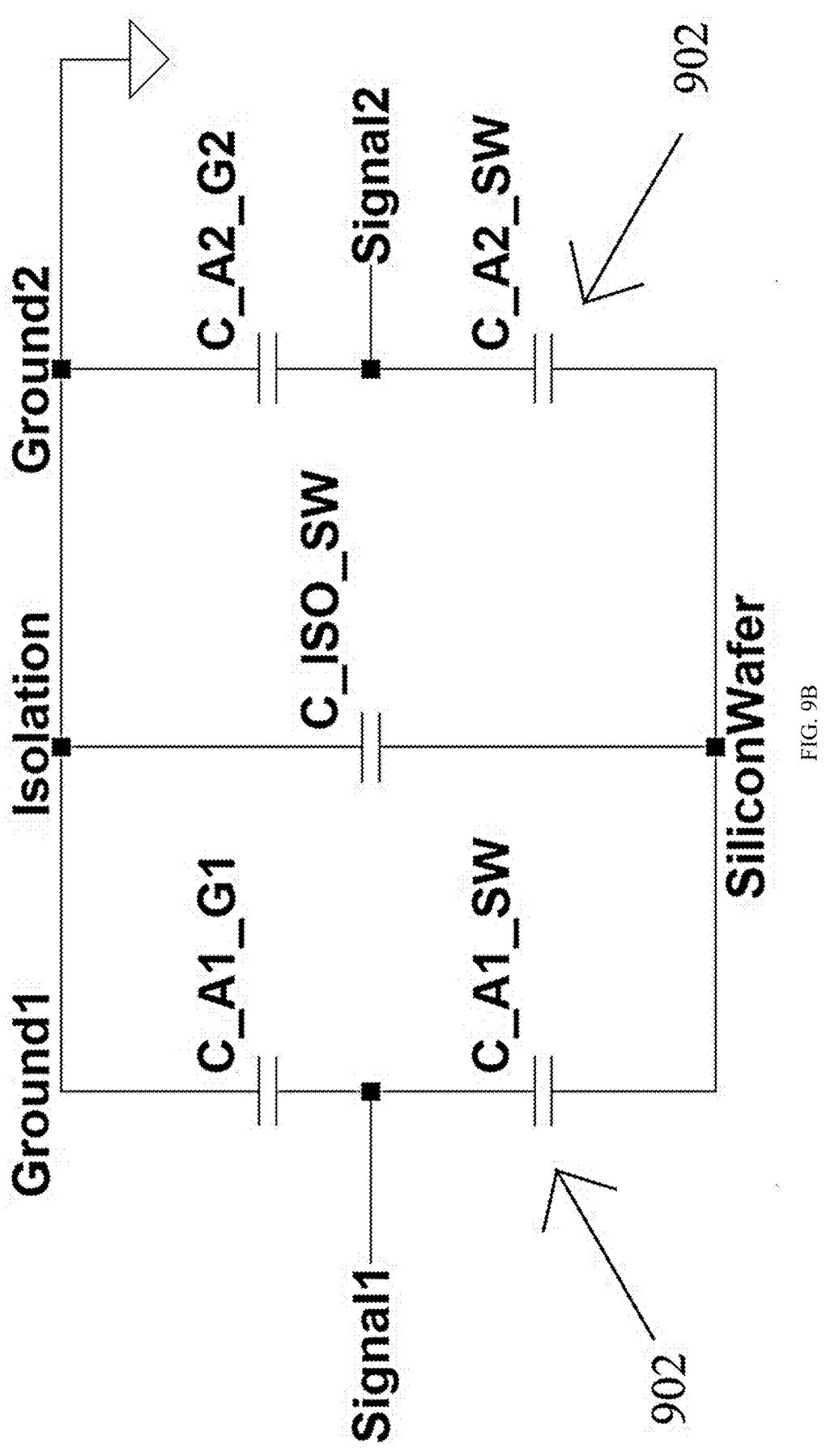

The capacitance circuitries were constructed from the extracted or extrapolated capacitance matrices of the regular CMUT array using the circuit scheme depicted in FIG. 9A. Since there are 6 nodes in the 2-element regular CMUT array structure, there are 15 capacitances between those nodes in total. Some nodes have been marked on capacitance circuitry of 2-element regular CMUT array as depicted in FIGS. 9A-9B where; "Array1" is the pin of the bottom electrode of the first array element (Array1 Signal, short notation: "A1"), "Ground1" is the pin of the top electrode of the first array element (Array1 Ground, short notation: "G1"), "Signal2" is the pin of the bottom electrode of the second array element (Array2 Signal, short notation: "A2"), "Ground2" is the pin of the top electrode of the second array element (Array 2 Ground, short notation: "G2"), "Isolation" is the pin of the isolation line (Isolation, short notation: "ISO") and "SiliconWafer" is the pin of the substrate (Silicon Wafer, short notation: "SW"). The capacitance between any node "X" and node "Y" is notated as "C_x_y" on the capacitance circuitry of the regular CMUT array as depicted in FIGS. 9A-9B, in which "x" and "y" are the short notation of the nodes "X" and "Y", respectively.

From the capacitance matrices of regular CMUT array, it is observed that some capacitances are infinitesimal compared to others. For the ease of the theoretical calculations, capacitances with a value 100 times smaller than the most significant capacitance on that capacitance matrices were treated as an open circuit. Furthermore, in the regular CMUT array operation, the isolation line, the top electrode of the first array and second elements are grounded, whereas the substrate can be floating or grounded. The simpler version of representative capacitance circuitry of the regular CMUT array is depicted in FIG. 9B based on the above information. For the theoretical calculation of the total array to ground capacitance ($C_{Tot}$) and the parasitic capacitance ($C_{Par}$) of the regular CMUT array, equations (1-2) (for floating substrate) and equations (3-4) (for grounded substrate) were used. For the theoretical calculation of the coupling capacitance ($C_{Coupling}$) of the regular CMUT array equation (5) was used.

$$C_{TOT} = C_{A1\_G1} + \left(C_{A1\_SW}//\left(C_{ISO\_SW} + \left(C_{A2\_SW}//C_{A2\_G2}\right)\right)\right) \quad (1)$$

$$C_{PAR} = C_{TOT} - C_{A1\_G1} = \left(C_{A1\_SW}//\left(C_{ISO\_SW} + \left(C_{A2\_SW}//C_{A2\_G2}\right)\right)\right) \quad (2)$$

$$C_{TOT} = C_{A1\_G1} + C_{A1\_SW} \quad (3)$$

$$C_{PAR} = C_{TOT} - C_{A1\_G1} = C_{A1\_SW} \quad (4)$$

$$C_{Coupling} = (C_{A1\_G1} + C_{A1\_SW})/2 \quad (5)$$

Figure 10A:
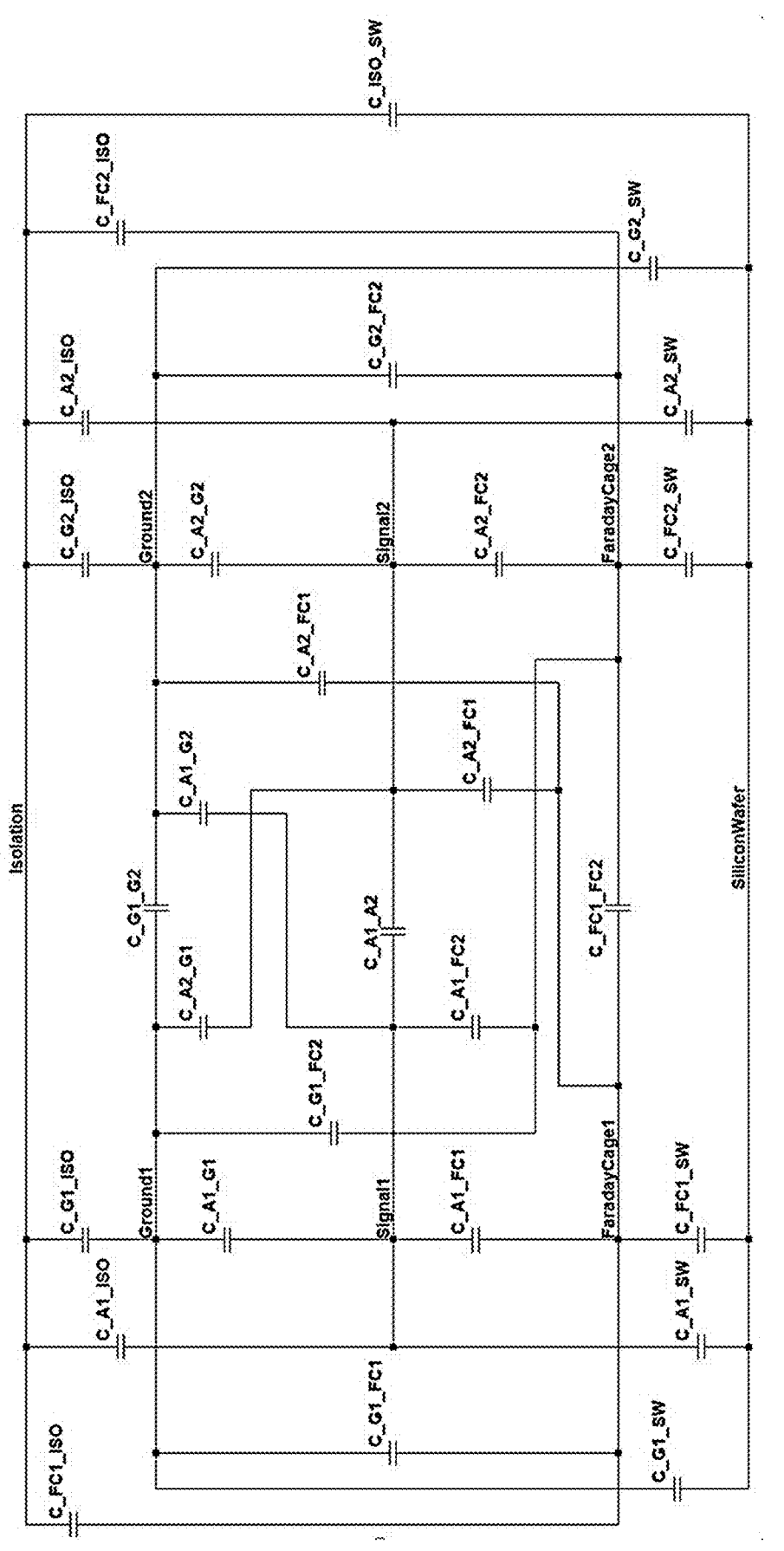
FIGS. 10A-10B show the capacitance circuitries of the 2-element Faraday Caged CMUT array.
Figure 10B:
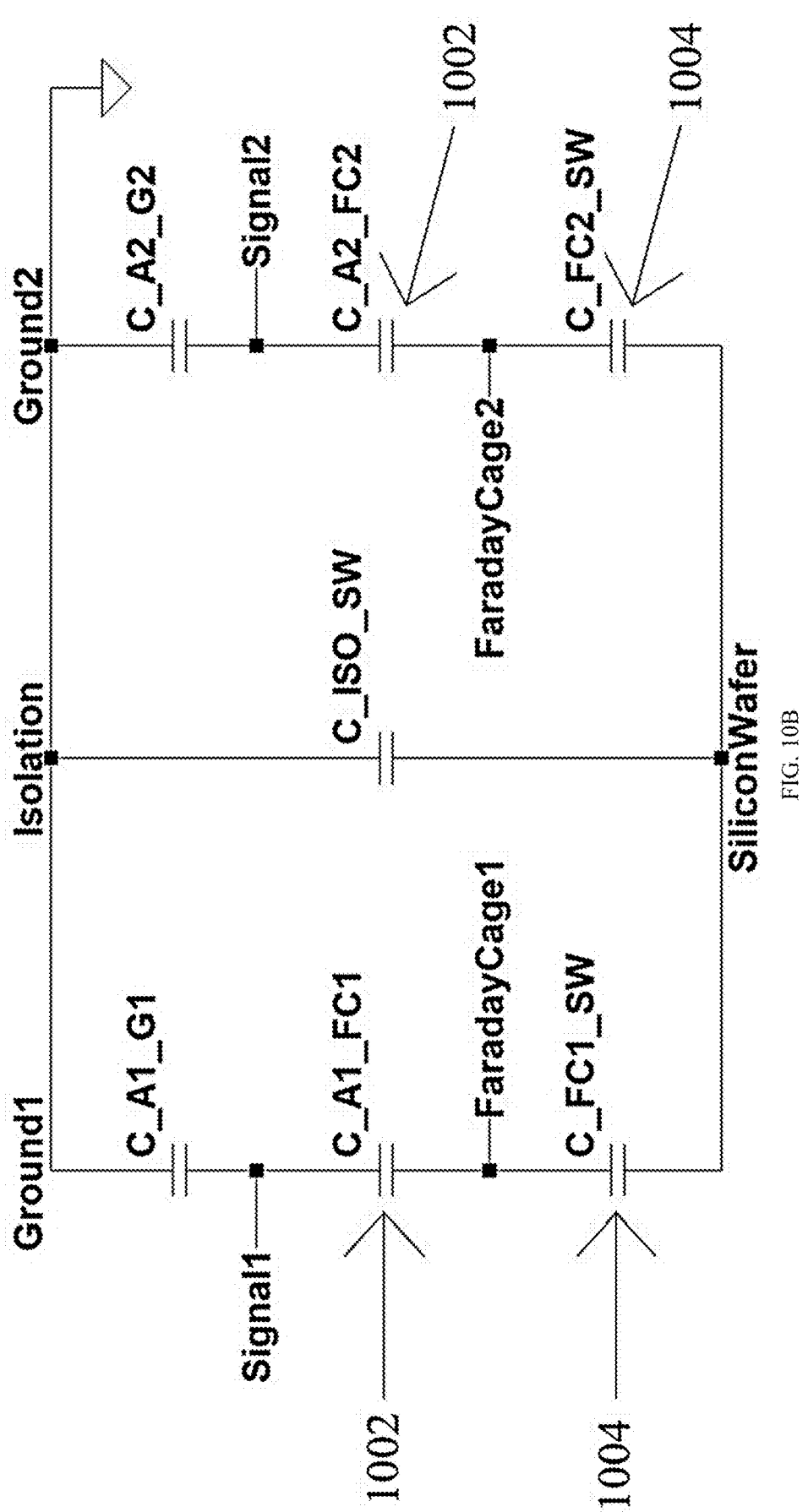

The capacitance circuitries were constructed from the extracted or extrapolated capacitance matrices of the Faraday Caged CMUT array using the circuit scheme depicted in FIG. 10A. Since there are 8 nodes in the 2-element regular CMUT array structure, there are 28 capacitances between those nodes in total. Some nodes have been marked on capacitance circuitry of 2-element Faraday Caged CMUT array as depicted in FIGS. 9A-9B where; "Signal1" is the pin of the bottom electrode of the first array element (Array1 Signal, short notation: "A1"), "Ground1" is the pin of the top electrode of the first array element (Array 1 Ground, short notation: "G1"), "Signal2" is the pin of the bottom electrode of the second array element (Array2 Signal, short notation: "A2"), "Ground2" is the pin of the top electrode of the second array element (Array2 Ground, short notation: "G2"), "FaradayCage1" is the pin of the Faraday cage of the first array element (Array 1 Faraday Cage, short notation: "FC1"), "FaradayCage2" is the pin of the Faraday cage of the second array element (Array 2 Faraday Cage, short notation: "FC2"), "Isolation" is the pin of the isolation line (Isolation, short notation: ISO) and "SiliconWafer" is the pin of the substrate (Silicon Wafer, short notation: "SW"). The capacitance between any node "X" and node "Y" is notated as "C_x_y" on the capacitance circuitry of Faraday Caged CMUT array as depicted in FIGS. 10A-10B, wherein "x" and "y" are short notation of the nodes "X" and "Y", respectively.

From the capacitance matrices of the Faraday Caged CMUT array, it is observed that some capacitances are infinitesimal compared to others. For the case of the theoretical calculations, capacitances with a value 100 times smaller than the most significant capacitance on that capacitance matrices were treated as an open circuit. Furthermore, in the Faraday Caged CMUT array operation, the isolation line, the top electrode of the first array element, and the top electrode of the second array element, are grounded whereas the Faraday cage of the first array element, the Faraday cage of the second array element, and the substrate can be floating or grounded. Based on the above information, the simpler version of representative capacitance circuitry of Faraday Caged CMUT array is depicted in FIG. 10B. For the theoretical calculation of the total array to ground capacitance ($C_{Tot}$), the parasitic capacitance ($C_{Par}$), and the coupling capacitance ($C_{Coupling}$) during the grounded operation the Faraday cages of the 2-element Faraday Caged CMUT array when the equations (6-8) (for floating and grounded substrate) were used. Since Faraday cages are grounded, the floating or grounded substrate operation does not affect the capacitive behavior of the CMUT array.

$$C_{TOT} = C_{A1\_G1} + C_{A1\_FC1} \tag{6}$$

$$C_{PAR} = C_{TOT} - C_{A1\_G1} = C_{A1\_FC1} \tag{7}$$

$$C_{Coupling} = (C_{A1\_G1} + C_{A1\_FC1})/2 \tag{8}$$

For the theoretical calculation of the total array to ground capacitance ($C_{Tot}$), and the parasitic capacitance ($C_{Par}$) during the floating operation of the Faraday cages of the 2-element Faraday Caged CMUT array, equations (9-10) (for floating substrate) and equations (11-12) (for grounded substrate) were used. For the theoretical calculation of the coupling capacitance ($C_{Coupling}$) during the floating operation of the Faraday cages of the 2-element Faraday Caged CMUT array equation (13) were used n the floating Faraday cage operation of the Faraday Caged CMUT array, between the bottom electrode and substrate, there are two capacitances (bottom electrode to Faraday cage 1002 and Faraday cage to substrate 1004) in series connection as depicted in FIG. 10B. In contrast, in the regular CMUT array there is one capacitance between bottom electrode to substrate 902. The capacitance values of bottom electrode to Faraday cage 1002, Faraday cage to substrate 1004 and bottom electrode to substrate 902 are expected to be similar. Thus, it had been expected that the floating operation of the Faraday cages of the Faraday Caged CMUT array would decrease the capacitive effects on the bottom electrode coming through the substrate compared to the regular CMUT array.

$$C_{TOT} = C_{A1\_G1} + \tag{9}$$
$$\left(\left(C_{A1\_FC1}//C_{FC1\_SW}\right)//\left(C_{ISO\_SW} + \left(\left(C_{A2\_FC2}//C_{FC2\_SW}\right)//C_{A2\_G2}\right)\right)\right)$$

$$C_{PAR} = C_{TOT} - C_{A1_{G1}} = \tag{10}$$
$$= \left(\left(C_{A1\_FC1}//C_{FC1\_SW}\right)//\left(C_{ISO\_SW} + \left(\left(C_{A2\_FC2}//C_{FC2\_SW}\right)//C_{A2\_G2}\right)\right)\right)$$

$$C_{TOT} = C_{A1\_G1} + \left(C_{A1\_FC1}//C_{FC1\_SW}\right) \tag{11}$$

$$C_{PAR} = C_{TOT} - C_{A1\_G1} = \left(C_{A1\_FC1}//C_{FC1\_SW}\right) \tag{12}$$

$$C_{Coupling} = \left(C_{A1\_G1} + \left(C_{A1\_FC1}//C_{FC1\_SW}\right)\right)/2 \tag{13}$$

ADS (Keysight, USA) was used as a circuit simulator to observe the capacitive behavior (total array to ground, parasitic and coupling capacitances) of the capacitive circuitries of the regular and Faraday Caged CMUT arrays. Based on the extracted or extrapolated capacitance matrices of regular and Faraday Caged CMUT arrays, the capacitance circuitries were constructed in ADS accordingly to the representative circuit schemes given in FIG. 9A and FIG. 10A, respectively.

In ADS two different configurations were used to examine the capacitive behavior of the capacitance circuitries. For the total array to ground capacitance characterization, the pin of the "Array1 Signal" was connected to a signal source with 50 Ohm input resistance, whereas the pin of the "Array2 Signal" was floating. Another configuration was required for coupling capacitance characterization, where a signal source with 50 Ohm input resistance is connected between the pins of the "Array1 Signal" and "Array2 Signal. The parasitic capacitance was found by subtracting the "Array1 Signal" to "Array1 Ground" capacitance from the found total array to ground capacitance. The capacitance seen by the signal source in both configurations was found using equations (14-17). The frequency input for the characterization of the capacitance circuitries is from 1 MHz to 10 MHz which is reasonable for CMUT array characterization.

$$Z_{Complex} = Z_{in}(S_{11}) \tag{14}$$

$$R = \text{Real}(Z_{Complex}) \tag{15}$$

$$I = \text{Imag}(Z_{Complex}) \tag{16}$$

$$C = \text{abs}\left(\frac{1}{I \times 2\pi f}\right) \tag{17}$$

Since the capacitances are almost constant over the frequency range, the mean values were used as the numerical result.

EMPro (Keysight, USA) was used to provide EM solutions for the 3-D built structures of the regular and Faraday Caged CMUT arrays for different row numbers. Then with the provided EM solution of the 3-D built structures of regular and Faraday Caged CMUT arrays from EMPro, the characterization of the 3-D built structure of the arrays was performed in ADS. Since ADS and EMPro can work coherently, the exported EM solution results found through EMPro were imported into ADS. Then the same configurations constructed for capacitive behavior (array to ground and coupling capacitance) analysis of capacitance circuitries was constructed for the capacitive behavior analysis of the 3-D built structures.

Building the 3-D structures of regular and Faraday Caged CMUT array require a feasible layout design. Because a CMUT array design with a very high row number value is not feasible (since an actual number is not assigned as row number) and because of the computational complexity, EM solutions of 3-D built structures of the regular and Faraday Caged CMUT arrays with a very high row number value (N) were not provided. Instead, EM solution of 3-D built structures of the regular and Faraday Caged CMUT arrays when row number is 10 (as a high row number approximation) were used to compare the crosstalk performance of the arrays regardless of the row number.

The total array to ground ($C_{Tot}$) and the parasitic capacitance ($C_{Par}$) found through theoretical calculations, circuit simulator, and EM solution of the 3-D built structure of the regular CMUT array is given in Table XV. The coupling capacitance ($C_{Coupling}$) found through theoretical calculations, circuit simulator, and EM solution of 3-D built structure of the regular CMUT array is given in Table XVI. It is observed that the capacitive behavior of the regular CMUT array, found through the different sources, (theory, circuit simulation and EM simulation) are in agreement with each other. Thus, it is concluded that the capacitive feature of the capacitance circuitry for a high row number case can represent the capacitive feature of the regular CMUT array regardless of the row number.

TABLE XV

The total array to ground ($C_{Tot}$) and parasitic capacitance ($C_{Par}$) of the regular CMUT array found through several evaluation types.

| | | Substrate Type | | | | | |
| | | Floating (pF) | | | Grounded (pF) | | |
| | | Result Type | | | | | |
| | | Theoretical Result | Circuit Simulator | EM Simulator (EMPro) | Theoretical Result | Circuit Simulator | EM Simulator (EMPro) |
|---|---|---|---|---|---|---|---|
| Row # 1 | $C_{Tot}$ | 1.07 | 1.07 | 1.09 | 1.43 | 1.43 | 1.43 |
| | $C_{Par}$ | 0.39 | 0.39 | — | 0.75 | 0.75 | — |
| Row # 2 | $C_{Tot}$ | 1.47 | 1.47 | 1.52 | 2.01 | 2.01 | 2.01 |
| | $C_{Par}$ | 0.53 | 0.53 | — | 1.07 | 1.07 | — |
| Row # 3 | $C_{Tot}$ | 1.87 | 1.88 | 1.87 | 2.60 | 2.61 | 2.64 |
| | $C_{Par}$ | 0.67 | 0.68 | — | 1.40 | 1.40 | — |
| Row # 10 | $C_{Tot}$ | 4.66 | 4.66 | 4.79 | 6.70 | 6.71 | 6.77 |
| | $C_{Par}$ | 1.63 | 1.63 | — | 3.67 | 3.68 | — |
| Row # N | $C_{Tot}$ | 0.40 | 0.40 | — | 0.59 | 0.59 | — |
| (High N) (×N) | $C_{Par}$ | 0.14 | 0.14 | — | 0.33 | 0.33 | — |

TABLE XVI

The coupling capacitance ($C_{Coupling}$) of the regular CMUT array found through several evaluation types.

| | Substrate Type | | | | | |
| | Floating (pF) | | | Grounded (pF) | | |
| | Result Type | | | | | |
| | Theoretical Result | Circuit Simulator | EM Simulator (EMPro) | Theoretical Result | Circuit Simulator | EM Simulator (EMPro) |
|---|---|---|---|---|---|---|
| Row # 1 | 0.71 | 0.71 | 0.71 | 0.71 | 0.71 | 0.72 |
| Row # 2 | 1.01 | 1.01 | 1.01 | 1.01 | 1.01 | 1.00 |
| Row # 3 | 1.30 | 1.31 | 1.28 | 1.30 | 1.31 | 1.31 |
| Row # 10 | 3.35 | 3.36 | 3.34 | 3.35 | 3.36 | 3.39 |
| Row # N (High N) (×N) | 0.29 | 0.29 | — | 0.29 | 0.29 | — |

The total array to ground ($C_{Tot}$) and parasitic capacitance ($C_{Par}$) found through theoretical calculations, circuit simulator, and EM solution of 3-D built structure of the Faraday Caged CMUT array during grounded operation of the Faraday cages is given in Table XVII. The coupling capacitance ($C_{Coupling}$) found through theoretical calculations, circuit simulator, and EM solution of 3-D built structure of the Faraday Caged CMUT array during grounded operation of the Faraday cages is given in Table XVIII. It is observed that the capacitive behavior of the Faraday Caged CMUT array for the grounded operation of the Faraday cages, found through different sources (theory, circuit simulation and EM simulation), are in agreement with each other. Thus, it is concluded that the capacitive feature of the capacitance circuitry for a high row number case can represent the capacitive feature during the grounded operation of the Faraday cages of the Faraday Caged CMUT array regardless of the row number.

TABLE XVII

The total array to ground ($C_{Tot}$) and parasitic capacitance
($C_{Par}$) of the Faraday Caged CMUT array during grounded operation
of the Faraday cages found through several evaluation types.

| | | Substrate Type | | | | |
| | | Floating (pF) | | | Grounded (pF) | | |
| | | | | Result Type | | | |
| | | Theoretical Result | Circuit Simulator | EM Simulator (EMPro) | Theoretical Result | Circuit Simulator | EM Simulator (EMPro) |
|---|---|---|---|---|---|---|---|
| Row # 1 | $C_{Tot}$ | 1.43 | 1.43 | 1.40 | 1.43 | 1.43 | 1.40 |
| | $C_{Par}$ | 0.75 | 0.75 | — | 0.75 | 0.75 | — |
| Row # 2 | $C_{Tot}$ | 2.01 | 2.01 | 1.98 | 2.01 | 2.01 | 2.01 |
| | $C_{Par}$ | 1.07 | 1.07 | — | 1.07 | 1.07 | — |
| Row # 3 | $C_{Tot}$ | 2.61 | 2.60 | 2.56 | 2.61 | 2.60 | 2.56 |
| | $C_{Par}$ | 1.40 | 1.35 | — | 1.40 | 1.35 | — |
| Row # 10 | $C_{Tot}$ | 6.70 | 6.70 | 6.61 | 6.70 | 6.70 | 6.61 |
| | $C_{Par}$ | 3.67 | 3.67 | — | 3.67 | 3.67 | — |
| Row # N (High N) (×N) | $C_{Tot}$ | 0.59 | 0.59 | — | 0.59 | 0.59 | — |
| | $C_{Par}$ | 0.33 | 0.33 | — | 0.33 | 0.33 | — |

TABLE XVIII

The coupling capacitance ($C_{Coupling}$) of the Faraday
Caged CMUT array during grounded operation of the Faraday
cages found through several evaluation types.

| | Substrate Type | | | | | |
| | Floating (pF) | | | Grounded (pF) | | |
| | | | Result Type | | | |
| | Theoretical Result | Circuit Simulator | EM Simulator (EMPro) | Theoretical Result | Circuit Simulator | EM Simulator (EMPro) |
|---|---|---|---|---|---|---|
| Row # 1 | 0.71 | 0.71 | 0.71 | 0.71 | 0.71 | 0.72 |
| Row # 2 | 1.01 | 1.01 | 1.01 | 1.01 | 1.01 | 1.00 |
| Row # 3 | 1.31 | 1.31 | 1.28 | 1.30 | 1.31 | 1.31 |
| Row # 10 | 3.35 | 3.35 | 3.31 | 3.35 | 3.35 | 3.31 |
| Row # N (High N) (×N) | 0.29 | 0.29 | — | 0.29 | 0.29 | — |

The total array to ground ($C_{Tot}$) and parasitic capacitance ($C_{Par}$) found through theoretical calculations, circuit simulator, and EM solution of 3-D built structure of the Faraday Caged CMUT array during floating operation of the Faraday cages is given in Table XIX. The coupling capacitance ($C_{Coupling}$) found through theoretical calculations, circuit simulator and EM solution of 3-D built structure of the Faraday Caged CMUT array during floating operation of the Faraday cages is given in Table XX. It is observed that the capacitive behavior of the Faraday Caged CMUT array for the grounded operation of the Faraday cages, found through different sources (theory, circuit simulation and EM simulation), holds each other. Thus, it is concluded that the capacitive feature of the capacitance circuitry for a high row number case can represent the capacitive feature during the floating operation of the Faraday cages of the Faraday Caged CMUT array regardless of the row number.

TABLE XIX

The total array to ground ($C_{Tot}$) and parasitic capacitance
($C_{Par}$) of the Faraday Caged CMUT array for floating operation
of the Faraday cages found through several evaluation types.

| | | Substrate Type | | | | | |
| | | Floating (pF) | | | Grounded (pF) | | |
| | | | | Result Type | | | |
| | | Theoretical Result | Circuit Simulator | EM Simulator (EMPro) | Theoretical Result | Circuit Simulator | EM Simulator (EMPro) |
|---|---|---|---|---|---|---|---|
| Row # 1 | $C_{Tot}$ | 0.92 | 0.93 | 0.94 | 1.06 | 1.06 | 1.04 |
| | $C_{Par}$ | 0.24 | 0.25 | — | 0.38 | 0.38 | — |
| Row # 2 | $C_{Tot}$ | 1.27 | 1.28 | 1.31 | 1.48 | 1.48 | 1.48 |
| | $C_{Par}$ | 0.33 | 0.34 | — | 0.54 | 0.54 | — |
| Row # 3 | $C_{Tot}$ | 1.63 | 1.62 | 1.68 | 1.91 | 1.90 | 1.90 |
| | $C_{Par}$ | 0.43 | 0.42 | — | 0.71 | 0.70 | — |
| Row # 10 | $C_{Tot}$ | 4.06 | 4.07 | 4.18 | 4.86 | 4.87 | 4.88 |
| | $C_{Par}$ | 1.03 | 1.04 | — | 1.83 | 1.84 | — |
| Row # N | $C_{Tot}$ | 0.35 | 0.35 | — | 0.42 | 0.42 | — |
| (High N) | $C_{Par}$ | 0.09 | 0.09 | — | 0.16 | 0.16 | — |
| (×N) | | | | | | | |

TABLE XX

The coupling capacitance ($C_{Coupling}$) of the Faraday Caged CMUT array for floating
operation of the Faraday cages found through several evaluation types.

| | Substrate Type | | | | | |
| | Floating (pF) | | | Grounded (pF) | | |
| | | | Result Type | | | |
| | Theoretical Result | Circuit Simulator | EM Simulator (EMPro) | Theoretical Result | Circuit Simulator | EM Simulator (EMPro) |
|---|---|---|---|---|---|---|
| Row # 1 | 0.53 | 0.53 | 0.53 | 0.53 | 0.53 | 0.52 |
| Row # 2 | 0.74 | 0.74 | 0.74 | 0.74 | 0.74 | 0.74 |
| Row # 3 | 0.96 | 0.95 | 0.95 | 0.96 | 0.95 | 0.95 |
| Row # 10 | 2.43 | 2.44 | 2.43 | 2.43 | 2.44 | 2.44 |
| Row # N | 0.21 | 0.21 | — | 0.21 | 0.21 | — |
| (High N) | | | | | | |
| (×N) | | | | | | |

Based on the circuit simulations, the parasitic capacitance ($C_{Par}$) and the coupling capacitance ($C_{Coupling}$) of the Faraday Caged CMUT array for grounded and floating operation of the Faraday cages were compared with the capacitive behavior of regular CMUT array. The comparison was performed between the corresponding substrate type of the CMUT arrays. It is observed that for high row number case when the substrate is floating, the floating operation of Faraday cages of the Faraday Caged CMUT array offers 35.7% less parasitic and 27.6% less coupling capacitance compared to regular CMUT array. It is observed that for high row number case when the substrate is grounded, the floating operation of Faraday cages of the Faraday Caged CMUT array offers 51.4% less parasitic and 27.6% less coupling capacitance compared to regular CMUT array.

The electrical crosstalk analyses of the regular and Faraday Caged CMUT array were performed using the EM solutions provided by EMPro and constructing the required configuration in ADS. For electrical crosstalk analysis, the pin of the "Array1 Signal" was connected to a signal source with 50 Ohm input resistance, whereas the pin of the "Array2 Signal" was connected to another signal source with 50 Ohm input resistance. Then the S12 parameter is examined over 1 MHz to 10 MHZ.

Figure 11A:
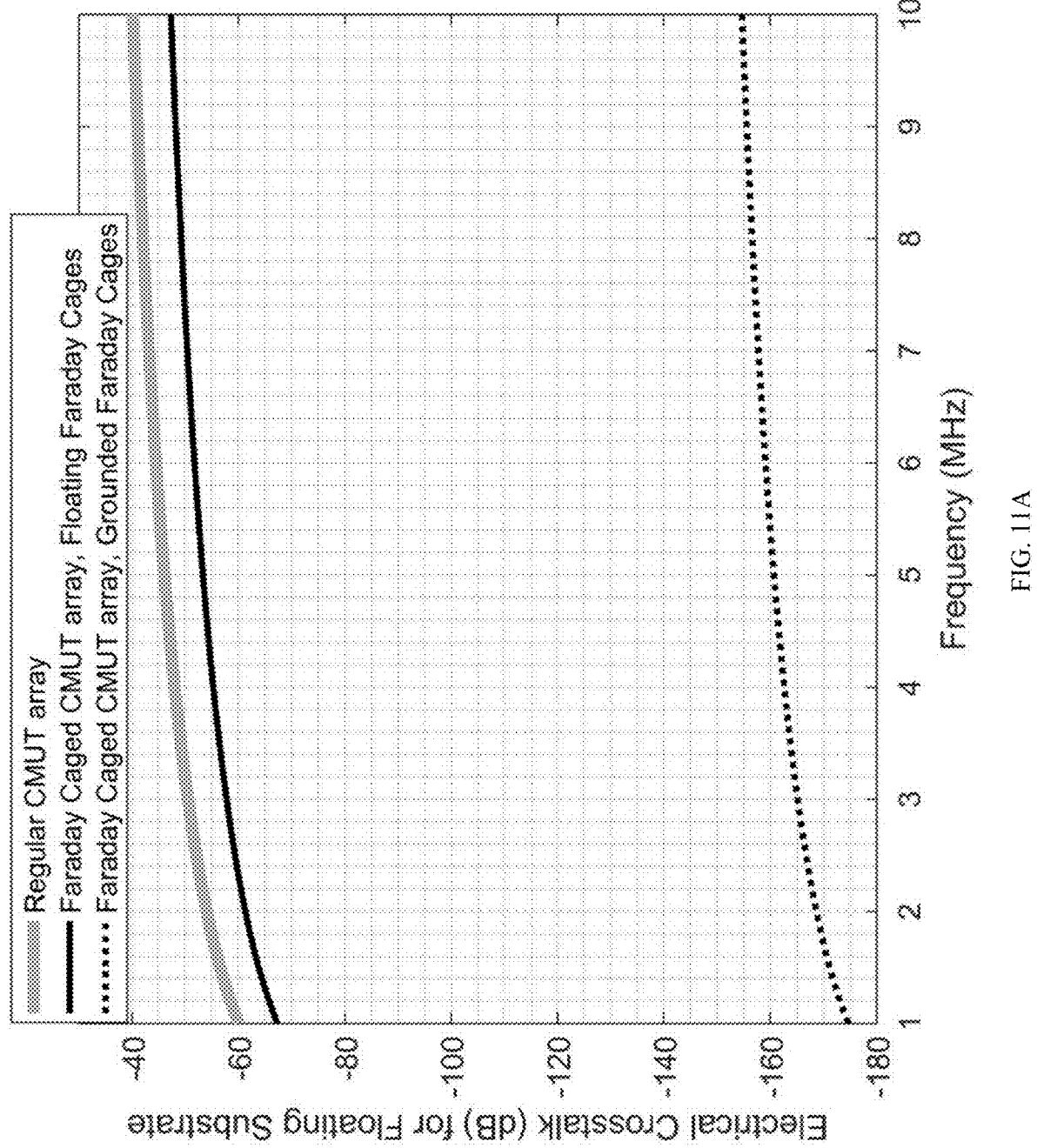
FIGS. 11A-11B show the electrical crosstalk performance based on the capacitance circuitries of the regular and Faraday Caged CMUT arrays.
Figure 11B:
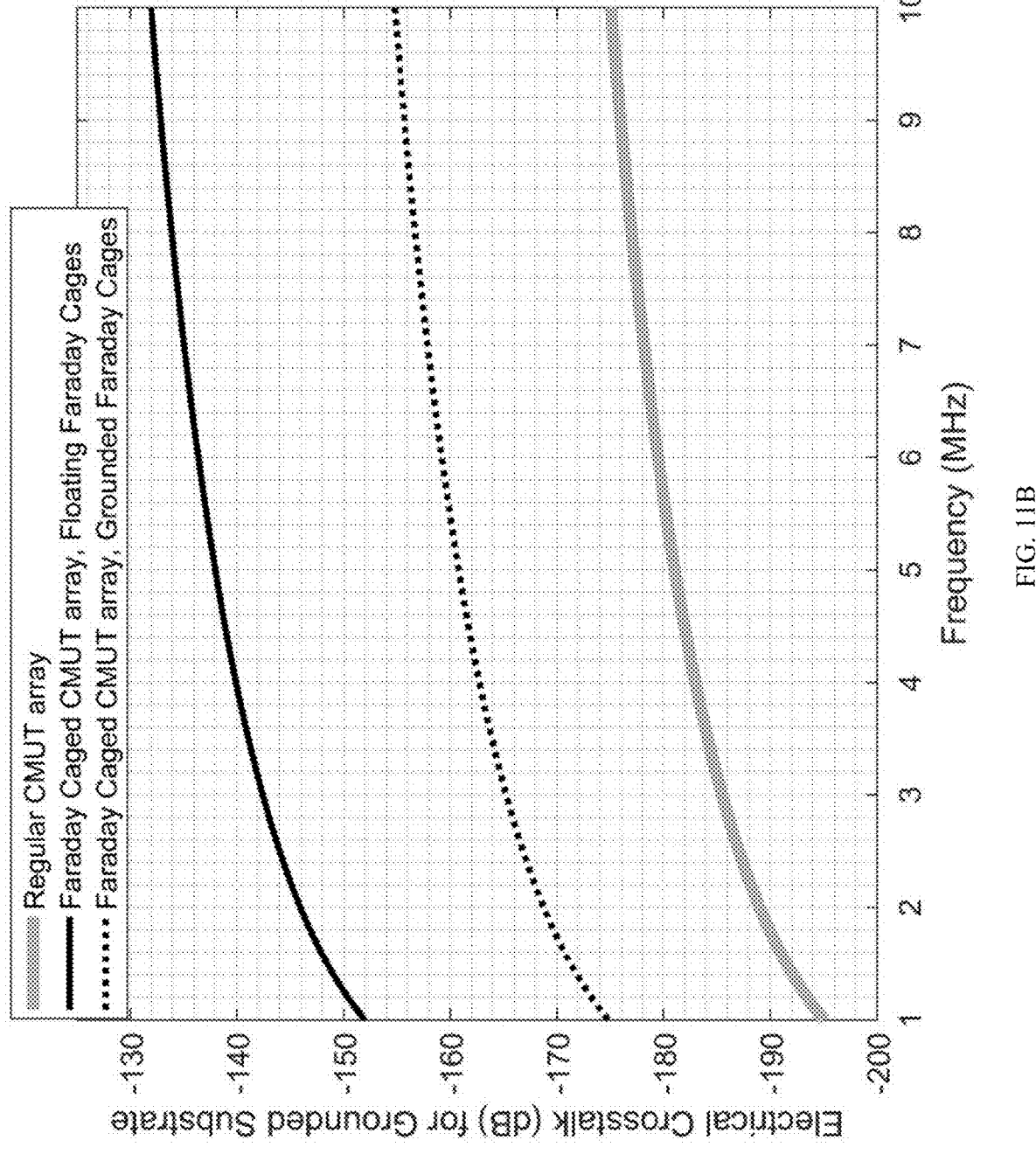
Figure 12A:
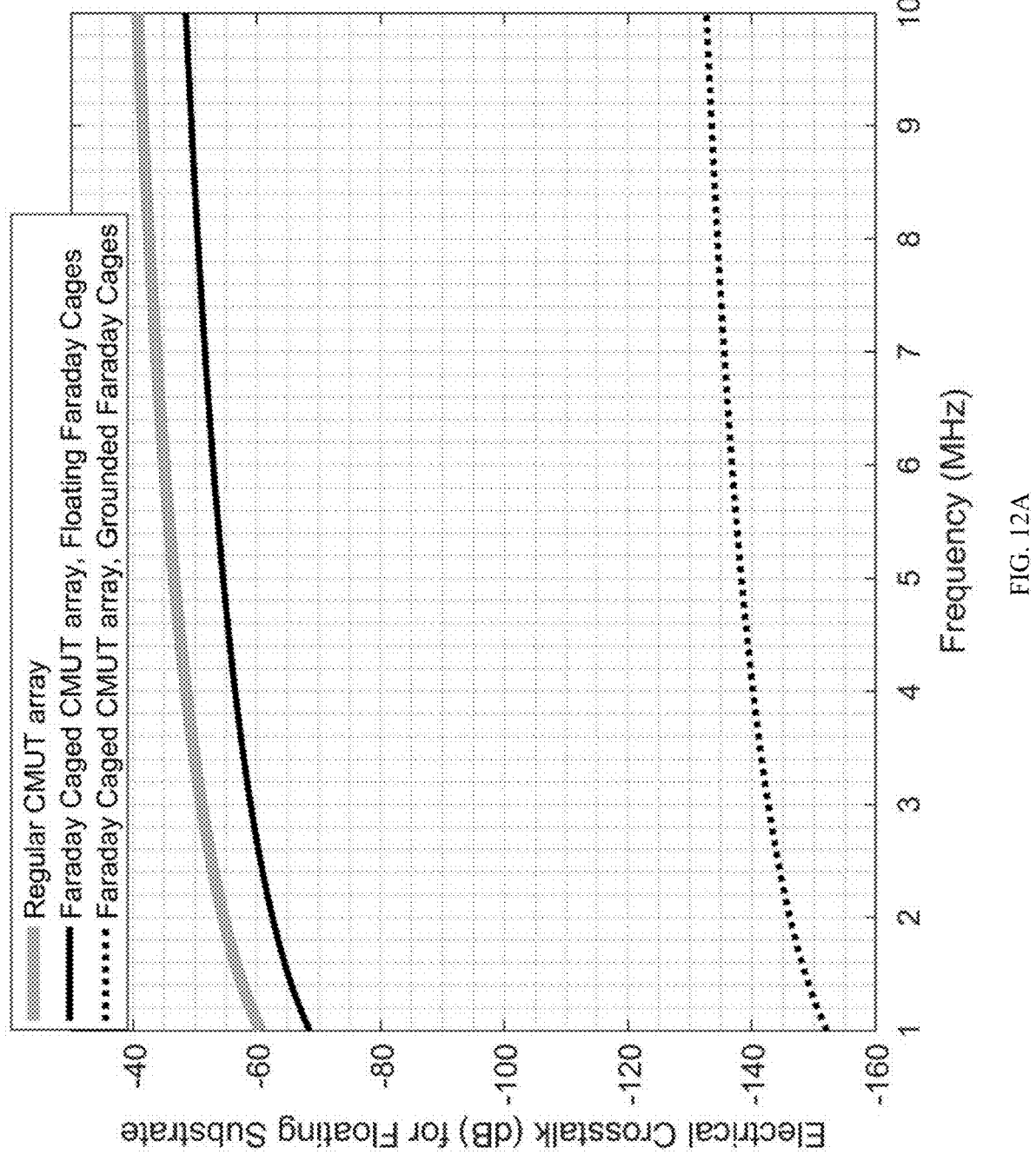
FIGS. 12A-12B show the electrical crosstalk performance based on the 3-D built structures of the regular and Faraday Caged CMUT arrays.
Figure 12B:
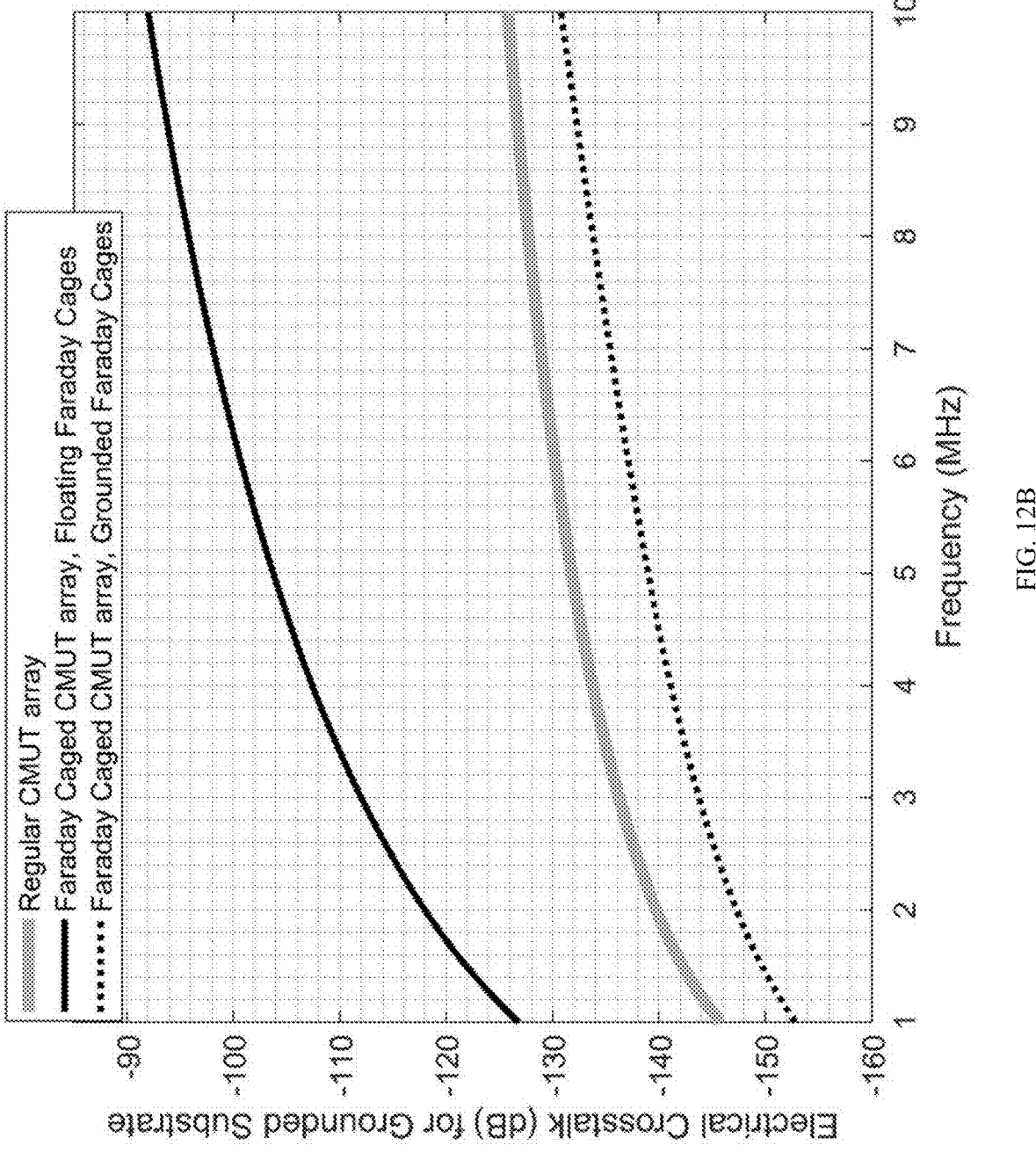

The electrical crosstalk of the capacitance circuitries of the regular and Faraday Caged CMUT arrays for operation of the Faraday cages (grounded and floating) when the row number is 10 was extracted for floating and grounded substrate as depicted in FIG. 11A and FIG. 11B, respectively. The electrical crosstalk of the 3-D built structures of the regular and Faraday Caged CMUT array for both operation of the Faraday cages (grounded and floating) when the row number is 10 was extracted for floating and grounded substrate as depicted in FIG. 12A and FIG. 12B, respectively. It is observed that the electrical crosstalk increases with frequency. For grounded substrate there is a significant difference between the crosstalk analysis of circuitries and 3-D built structures. Because the crosstalk in those cases is very low, the effect of resistivity of the materials is observed in the crosstalk examination of the 3-D built structures. Since, the resistivity of substrate (handle wafer, 5 Ohm·cm) is higher than the resistivity of the Faraday cage (device layer, 0.005 Ohm·cm), the regular CMUT array and floating Faraday cage operation of the Faraday Caged CMUT array are affected more from the resistivity effect compared to grounded Faraday cage operation of the Faraday Caged CMUT array. For floating substrate, except the grounded Faraday cage operation of the Faraday Caged CMUT array, the crosstalk of circuit and 3-D built structures are similar since the crosstalk due the resistivity of the materials is not dominant.

The minimum, mean and maximum crosstalk value of the capacitance circuitries of the regular and Faraday Caged CMUT array for floating and grounded operation when the row number is 10 is given in Table XXI. The minimum, mean and maximum crosstalk value of the 3-D built structures of the regular and Faraday Caged CMUT array for floating and grounded operation when the row number is 10 is given in Table XXII.

TABLE XXI

The electrical crosstalk feature of capacitance circuitries of the regular CMUT array and the Faraday Caged CMUT array for floating and grounded operation of Faraday cages.

| | Regular CMT array | | Faraday Caged CMUT array | | | |
| | | | Floating Faraday Cage Substrate Type | | Grounded Faraday Cage | |
| | Floating (dB) | Grounded (dB) | Floating (dB) | Grounded (dB) | Floating (dB) | Grounded (dB) |
| --- | --- | --- | --- | --- | --- | --- |
| Min (at 1 MHz) | −60.11 | −195.03 | −67.36 | −151.97 | −174.68 | −174.79 |
| Max (at 10 MHz) | −40.12 | −175.04 | −47.36 | −131.97 | −154.68 | −154.79 |
| Mean | −46.58 | −181.50 | −53.83 | −138.44 | −161.14 | −161.25 |

TABLE XXII

The electrical crosstalk feature of 3-D built structures of the regular CMUT array and Faraday Caged CMUT array for floating and grounded operation of Faraday cages.

| | Regular CMT array | | Faraday Caged CMUT array | | | |
| | | | Floating Faraday Cage Substrate Type | | Grounded Faraday Cage | |
| | Floating (dB) | Grounded (dB) | Floating (dB) | Grounded (dB) | Floating (dB) | Grounded (dB) |
| --- | --- | --- | --- | --- | --- | --- |
| Min (at 1 MHz) | −60.64 | −145.78 | −68.55 | −126.78 | −152.14 | −152.79 |
| Max (at 10 MHz) | −40.67 | −125.81 | −48.56 | −92.02 | −132.70 | −130.78 |
| Mean | −47.11 | −132.25 | −55.02 | −104.25 | −138.83 | −139.00 |

It is observed from the crosstalk analyses of 3-D built structures of the regular and Faraday Caged CMUT array that, the grounded operation of Faraday cages of the Faraday Caged CMUT array offers 97.72 dB and 6.75 dB decrease in overall over the frequency range of 1 MHz to 10 MHz compared to floating operation of the Faraday cages of the Faraday Caged CMUT array for floating and grounded substrate, respectively. The crosstalk difference between the grounded operation of Faraday cages of the Faraday Caged CMUT array and the regular CMUT array for grounded substrate is due to effect of resistivity difference between the substrate and Faraday cage.

It is observed that, the grounded operation of Faraday cages of the Faraday Caged CMUT array offers 83.81 dB and 34.75 dB decrease in overall over the frequency range of 1 MHz to 10 MHZ compared to floating operation of the Faraday cages of the Faraday Caged CMUT array for floating and grounded substrate, respectively.

Various embodiments and applications employing the principles of the present invention can be implemented. Therefore, the scope of this invention is not limited to the examples above but determined by the following claims.

REFERENCES

[1] R. S. Moorthy, "Doppler ultrasound," Medical Journal Armed Forces India, 2002, 58(1), 1-2.

[2] R. Sigrist, J. Liau, A. E. Kaffas, M. C. Chammas, and J. K. Willmann, "Ultrasound Elastography: Review of Techniques and Clinical Applications," Theranostics, 2017, 7(5), 1303-1329.

[3] P. Santos, A. M. Petrescu, J. P. Pedrosa, M. Orlowska, V. Komini, J. U. Voigt, and J. D'hooge, "Natural Shear Wave Imaging in the Human Heart: Normal Values, Feasibility, and Reproducibility," in IEEE Transactions on Ultrasonics, Ferroelectrics, and Frequency Control, vol. 66, no. 3, pp. 442-452, March 2019.

[4] M. Tanter, and M. Fink, "Ultrafast imaging in biomedical ultrasound. IEEE transactions on ultrasonics, ferroelectrics, and frequency control", 2014, 61(1), 102-119.

[5] J. Brown, K. Christensen-Jeffries, S. Harput, G. Zhang, J. Zhu, C. Dunsby, M. X. Tang, and R. J. Eckersley, "Investigation of Microbubble Detection Methods for Super-Resolution Imaging of Microvasculature," in IEEE Transactions on Ultrasonics, Ferroelectrics, and Frequency Control, vol. 66, no. 4, pp. 676-691, April 2019.

[6] K. Christensen-Jeffries, O. Couture, P. A. Dayton, Y. C. Eldar, K. Hynynen, F. Kiessling, M. O'Reilly, G. F. Pinton, G. Schmitz, M.-X. Tang, M. Tanter, R. J. G. van Sloun, "Super-resolution Ultrasound Imaging," Ultrasound in Medicine & Biology, Volume 46, Issue 4, 2020, Pages 865-891, ISSN 0301-5629.

[7] X. Qian, H. Kang, R. Li, G. Lu, Z. Du, K. K. Shung, M. S. Humayun, and Q. Zhou, "In vivo Visualization of Eye Vasculature using Super-resolution Ultrasound Microvessel Imaging," in IEEE Transactions on Biomedical Engineering, doi: 10.1109/TBME.2020.2972514.

[8] D. Buonsenso, A. Piano, F. Raffaelli, N. Bonadia, K. D. G. Donati, and F. Franceschi, "Point-of-Care Lung Ultrasound findings in novel coronavirus disease-19 pnemoniae: a case report and potential applications during COVID-19 outbreak," European Review for Medical and Pharmacological Sciences, 2020, 24:2776-2780.

[9] P. Chen, T. Yang, L. Kuo, C. Shih and C. Huang, "Characterization of Hand Tendons Through High-Frequency Ultrasound Elastography," in IEEE Transactions on Ultrasonics, Ferroelectrics, and Frequency Control, vol. 67, no. 1, pp. 37-48, January 2020, doi: 10.1109/TUFFC.2019.2938147.

[10] S. P. Arjunan, and M. C. Thomas, "A Review of Ultrasound Imaging Techniques for the Detection of Down Syndrome", IRBM, Volume 41, Issue 2, 2020, Pages 115-123.

[11] A. Nabavizadeh, T. Payen, A. C. Iuga, I. R. Sagalovskiy, D. Desrouilleres, N. Saharkhiz, C. F. Palermo, S. A. Sastra, P. E. Oberstein, V. Rosario, M. D. Kluger, B. A. Schrope, J. A. Chabot, K. P. Olive, and E. E. Konofagou, "Noninvasive Young's modulus visualization of fibrosis progression and delineation of pancreatic ductal adenocarcinoma (PDAC) tumors using Harmonic Motion Elastography (HME) in vivo," Theranostics, 2020, 10(10), 4614-4626.

[12] C. Rabut, M. Correia, V. Finel, S. Pezet, M. Pernot, T. Deffieux, and M. Tanter, "4D functional ultrasound imaging of whole-brain activity in rodents", Nat Methods 2019, 16, 994-997.

[13] A. Novell, H. A. S. Kamimura, A. Cafarelli, M. Gerstenmayer, J. Flament, J. Valette, P. Agou, A. Conti, E. Selingue, R. Aron Badin, P. Hantraye, and B. Larrat, "A new safety index based on intrapulse monitoring of ultraharmonic cavitation during ultrasound-induced blood-brain barrier opening procedures," Sci Rep, 2020, 10, 10088.

[14] Y. Tian, Z. Liu, H. Tan, J. Hou, X. Wen, F. Yang, and W. Cheng, "New Aspects of Ultrasound-Mediated Targeted Delivery and Therapy for Cancer", International journal of nanomedicine, 2020, 15, 401-418.

[15] M. I. Haller, and B. T. Khuri-Yakub, "A surface micromachined electrostatic ultrasonic air transducer," in Ultrasonics Symposium, 1994. Proceedings., 1994 IEEE, 1-4 Nov. 1994, vol. 2, pp. 1241-1244.

[16] P. C. Eccardt, K. Niederer, T. Scheiter, and C. Hierold, "Surface micromachined ultrasound transducers in CMOS technology," in Proc. IEEE Ultrasonics Symp., 1996, vol. 2, pp. 959-962.

[17] B. Bayram, E. Hæggstrom, G. G. Yaralioglu, and B. T. Khuri-Yakub, "A new regime for operating capacitive micromachined ultrasonic transducers," IEEE Trans. on Ultrason. Ferroelect. Freq. Contr., vol. 50, no. 9, pp. 1184-1190 September 2003.

[18] B. Bayram. O. Oralkan, A. S. Ergun, E. Hæggstrom, G. G. Yaralioglu, and B. T. Khuri-Yakub "Capacitive micromachined ultrasonic transducer design for high power transmission," IEEE Trans. on Ultrason. Ferroelect. Freq. Contr., vol. 52, no. 2, pp. 326-339, February 2005.

[19] K. Brenner, A. S. Ergun, K. Firouzi, M. F. Rasmussen, Q. Stedman, and B. T. Khuri-Yakub, "Advances in Capacitive Micromachined Ultrasonic Transducers", Micromachines 2019, 10, 152.

[20] R. Schaijk, "CMUT and PMUT: New technology platform for medical ultrasound," Philips Innovation Services MEMS&Micro Devices Report, 2018.

[21] A. Sako, K. Ishida, M. Fukada, K. Asafusa, S. Sano and M. Izumi, "Development of ultrasonic transducer 'Mappie' with cMUT technology", MEDIX Hitachi Med. Corp. Japan, vol. 51, pp. 31-34, 2009.

[22] B. Bayram, O. Oralkan, and B. T. Khuri-Yakub. "Method and system for operating capacitive membrane ultrasonic transducers," U.S. Pat. No. 7,274,623 B2, patent date: 25 Sep. 2007.

[23] B. Bayram, and A. B. Sahin, "MEMS Airborne Ultrasonic Transducer System for Detecting Brain Haemorrhage", PCT Application No: PCT/TR2019/051050, International filing date: 9 Dec. 2019.

[24] A. Pirouz, and F. L. Degertekin, "An analysis method for capacitive micromachined ultrasound transducer (CMUT) energy conversion during large signal operation," Sensors, vol. 19, no. 4, pp. 876-890, February 2019.

[25] G. G. Yaralioglu, A. S. Ergun, B. Bayram, E. Haeggström, and B. T. Khuri-Yakub, "Calculation and Measurement of Electromechanical Coupling Coefficient of Capacitive Micromachined Ultrasonic Transducers," IEEE Trans. Ultrason., Ferroelect., Freq. Cont., vol. 50, pp. 449-456, April 2003.

[26] B. Bayram, M. Kupnik, G. G. Yaralioglu, O. Oralkan, A. S. Ergun, D. S. Lin. S. H. Wong, and B. T. Khuri- Yakub, "Finite element modeling and experimental characterization of crosstalk in 1-D CMUT arrays," IEEE Trans. on Ultrason. Ferroelect. Freq. Contr., vol. 54, no. 2, pp. 418-430, February 2007.

[27] B. Bayram, and B. T. Khuri-Yakub. "Acoustic crosstalk reduction for capacitive micromachined ultrasonic transducers in immersion," U.S. Pat. No. 7,745,973, patent date: 29 Jun. 2010.

[28] A. Sampaleanu, P. Zhang, A. Kshirsagar, W. Moussa, and R J Zemp. "Top-orthogonal-to-bottom-electrode (TOBE) CMUT arrays for 3-D ultrasound imaging." IEEE Trans. on Ultrason. Ferroelect. Freq. Contr., vol. 61, no. 2, pp 266-276, February 2014.

[29] A. Buhrdorf, A. Lohfink, S. Junge, P. C. Eccardt, and W. Benecke. "Fabrication and characterization of a new capacitive micromachined ultrasonic transducer (cMUT) using polysilicon as membrane and sacrificial layer material," In IEEE Symposium on Ultrasonics, vol. 2, pp. 1951-1954, 2003.

[30] X. Zhuang. A. S. Ergun, O. Oralkan, Y. Huang, I. O. Wygant, G. G. Yaralioglu, and B. T. Khuri-Yakub. "Through-wafer trench-isolated electrical interconnects for CMUT arrays". IEEE Ultrasonics Symposium, Vol. 1, pp. 475-478. September 2005.

[31] X. Zhuang. A. S. Ergun, O. Oralkan, I. O. Wygant, and B. T. Khuri-Yakub. "Interconnection and packaging for 2D capacitive micromachined ultrasonic transducer arrays based on through-wafer trench isolation," 19th IEEE International Conference on Micro Electro Mechanical Systems, pp. 270-273, 2006.

[32] X. Zhuang, A. S. Ergun, Y. Huang, I. O. Wygant, O. Oralkan, and B. T. Khuri-Yakub. "Integration of trench-isolated through-wafer interconnects with 2D capacitive micromachined ultrasonic transducer arrays," Sensors and Actuators A: Physical, vol. 138, no. 1, pp. 221-229, July 2007.

[33] X. Zhuang, O Oralkan, B. T. Khuri-Yakub, A. S. Ergun, and D. S. Lin. "Trench-isolated CMUT arrays with a supporting frame". IEEE Ultrasonics Symposium, pp. 1955-1958, 2006.

[34] X. Zhuang. I. O. Wygant, D. S. Lin, M. Kupnik, O. Oralkan, and B. T. Khuri-Yakub. "Trench-Isolated CMUT Arrays with a Supporting Frame: Characterization and Imaging Results," IEEE Ultrasonics Symposium Proceedings, pp. 507-510, 2007.

[35] X Zhuang, I. O. Wygant. D. S. Lin, M. Kupnik, O. Oralkan, and B. T. Khuri-Yakub. "Wafer-bonded 2-D CMUT arrays incorporating through-wafer trench-isolated interconnects with a supporting frame," IEEE Trans. on Ultrason. Ferroelect. Freq. Contr., vol. 56, no. 1, pp. 182-192, January 2009.

[36] B. T. Khuri-Yakub, T. Butrus, X. Zhuang, and A. S. Ergun. "Trench isolated capacitive micromachined ultrasonic transducer arrays with a supporting frame," U.S. Pat. No. 7,741,686, patent date: 22 Jun. 2010.

[37] X. Zhuang, D. S. Lin, O. Oralkan, and B. T. Khuri-Yakub. "Fabrication of flexible transducer arrays with through-wafer electrical interconnects based on trench refilling with PDMS," Journal of Microelectromechanical Systems, vol. 17, no. 2, pp. 446-452, April 2008.

[38] P. Zhang, G. Fitzpatrick, T. Harrison, W. A. Moussa, and R. J. Zemp. "Double-SOI wafer-bonded CMUTs with improved electrical safety and minimal roughness of dielectric and electrode surfaces," Journal of microelectromechanical systems, vol. 21, no. 3, pp. 668-680, June 2012.

43

[39] S. Berg, K. Chapagain, J. Due-Hansen, K. A. Ingebrigt-
sen, G. U. Jensen, K. Midtbø, E. U. Poppe. A. Rønnekleiv,
and D. T. Wang, "Wafer bond cmut array with conductive
vias," Patent Application No: US 2012/0074509 A1. App.
date: 29 Mar. 2012.
[40] B. C. Lee, A. Nikoozadeh, K. K. Park, and B. T,
Khuri-Yakub. "Fabrication of CMUTs with substrate-
embedded springs," IEEE International Ultrasonics Sym-
posium (IUS), (pp. 1733-1736), 2013.
[41] F. L. Degertekin, "Harmonic cMUT devices and fab-
rication methods," Patent No: U.S. Pat. No. 8,398,554 B2.
Patent date: 19 Mar. 2013.
[42] R. O. Guldiken "Dual-electrode capacitive microma-
chined ultrasonic transducers for medical ultrasound
applications," (Doctoral dissertation, Georgia Institute of
Technology), 2008.
[43] R. K. W. Chee, A. Sampaleanu, D. Rishi and R J. Zemp,
"Top orthogonal to bottom electrode (TOBE) 2-D CMUT
arrays for 3-D photoacoustic imaging," IEEE Trans. on
Ultrason. Ferroelect. Freq. Contr., vol. 61, no. 8. pp.
1393-1395 August 2014.
[44] A. Hajati, D. Latev, D. Gardner, and H. S. Law,
"Micromachined ultrasonic transducer devices with
metal-semiconductor contact for reduced capacitive
crosstalk," Patent No. U.S. Pat. No. 9,375,850. patent
date: 28 Jun. 2016.
[45] J. C. Hwang, "Reliability of electrostatically actuated
RF MEMS switches," In 2007 IEEE International Work-
shop on Radio-Frequency Integration Technology, pp.
168-171, 2007.
[46] S. Falabella, "Amorphous-diamond electron emitter,"
U.S. Pat. No. 6,204,595. patent date: 20 Mar. 2001.
[47] O. A. Ivanov, S. A. Bogdanov, A. L. Vikharev, V. V.
Luchinin, V. A. Golubkov, A. S. Ivanov, and V. A. Ilyin.
"Emission properties of undoped and boron-doped nanoc-
rystalline diamond films coated silicon carbide field emit-
ter arrays," Journal of Vacuum Science & Technology B,
Nanotechnology and Microelectronics: Materials, Pro-
cessing, Measurement, and Phenomena, vol. 36, no. 2,
March 2018.
[48] F. Giubileo, A., Di Bartolomeo, L. Iemmo, G. Luongo,
and F. Urban, "Field emission from carbon nanostruc-
tures," Applied Sciences, vol. 8, no. 4, pp. 526-546,
March 2018.
[49] K. J. Sankaran, M. Ficek, K. Panda, C. J. Yeh, M.
Sawczak, J. Ryl, K. Leou, J. Y. Park, I. Lin, R. Bogdano-
wicz, and K. Haenen. "Boron-Doped Nanocrystalline
Diamond-Carbon Nanospike Hybrid Electron Emission
Source," ACS Applied Materials & Interfaces, vol. 11, no.
51, pp. 48612-48623, December 2019.
[50] X. Jiang, F. C. Au, and S. T. Lee, S. T. "Ultrahigh boron
doping of nanocrystalline diamond films and their elec-
tron field emission characteristics," Journal of applied
physics, vol. 92, no. 5, pp. 2880-2883 June 2002.
[51] V. T. Srikar, and S. M. Spearing, "Materials selection in
micromechanical design: an application of the Ashby
approach," Journal of Microelectromechanical Systems,
vol. 12, no. 1, pp. 3-10. February 2003.
[52] P. Ashcheulov, J. Šebera, A. Kovalenko, V. Petrák, F.
Fendrych, M. Nesládek, A. Taylor, Z. V. Zivcova, O.
Frank, L. Kavan, M. Dracinsky, P. Hubík, J. Vacík, & I.
Kratochvílová, "Conductivity of boond-doped polycrys-
talline diamond films: influence of specific boron
defects," The European Physical Journal B, vol. 86, no.
10, pp. 1-9, October 2013.
[53] B. Bayram, O. Akar, and T. Akin, "Plasma-activated
Direct Bonding of Diamond-on-insulator wafers to Ther-

44 mal Oxide grown Silicon Wafers," Diam. Relat. Mater.,
vol. 19, no. 11, pp. 1431-1435 November 2010.
[54] B. Bayram, and H. S. Altinoluk, "Microfabrication of
vacuum-sealed cavities with nanocrystalline and ultranan-
ocrystalline diamond membranes and their characteris-
tics," Diam. Relat. Mater., vol. 20, no. 8, pp. 1149-1154
August 2011.
[55] B. Bayram, "Fabrication of SiO₂-stacked diamond
membranes and their characteristics for microelectrome-
chanical applications," Diam. Relat. Mater., vol. 20, no. 4,
pp. 459-463, April 2011.
[56] B. Bayram, "Diamond-based capacitive microma-
chined ultrasonic transducers," Diam. Relat. Mater., vol.
22, no. 2, pp. 6-11, February 2012.
[57] B. Bayram, "Method for microfabrication of a capaci-
tive micromachined ultrasonic transducer comprising a
diamond membrane and a transducer thereof," patent no:
U.S. Pat. No. 8,421,170 B2, patent date: 16 Apr. 2013.
[58] A. M. Cetin, and B. Bayram, "Diamond-based capaci-
tive micromachined ultrasonic transducers in immersion,"
IEEE Trans. Ultrason. Ferroelect. Freq. Contr., vol. 60,
no. 2, pp. 414-420, February 2013.
[59] U. I. Can, and B. Bayram, "Plasma-activated direct
bonding of patterned silicon-on-insulator wafers to dia-
mond-coated wafers under vacuum," Diam. Relat. Mater.,
vol. 47, pp. 53-57, August 2014.
[60] B. Bayram, "Bir elmas membran ve bir çevirgeçten
oluşan bir kapasitif mikroüretilmiş ultrasonik çevirgecin
mikroüretim yöntemi," patent no: TR 2013 12896 B,
patent date: 21 Aug. 2014.
[61] B. Bayram, "A Method for microfabrication of a
capacitive micromachined ultrasonic transducer compris-
ing a diamond membrane and a transducer thereof,"
patent no: EP 2,697,160 B1, patent date: 6 May 2015.

What is claimed is:

1. A capacitive micromachined ultrasonic transducer
(CMUT) array comprising:
a) at least two array elements, wherein each of the at least
two array elements features a plurality of CMUT cells
and a single lightning rod structure,
b) each of the plurality of CMUT cells having a top-to-
bottom stack of a top electrode conductor, a membrane,
a vacuum cavity, a first insulation dielectric layer, a
bottom electrode conductor, a second insulation dielec-
tric layer, a Faraday cage electrode conductor, a third
insulation layer and a substrate, wherein the Faraday
cage electrode conductor is electrically isolated from
the bottom electrode conductor and the substrate by the
first insulation dielectric layer and the third insulation
dielectric layer, respectively,
c) each of the lightning rod structures having a top-to-
bottom stack of a grounded electrode conductor, a
conductive diamond membrane, a cavity, a conductive
diamond emitter and the Faraday cage electrode con-
ductor of the array element.
2. The CMUT array according to claim 1, wherein
a) the Faraday cage electrode conductor is conductive and
common to the plurality of CMUT cells and the light-
ning rod structure of the array element, and the Faraday
cage electrode conductor is electrically isolated from
Faraday cage electrode conductors of other array ele-
ments,
b) the Faraday cage electrode conductor is selectively
connectable to grounded state and selectively discon-
nect-able from ground to define a floating state,
c) the Faraday cage electrode conductor is unique to the
array element, and the Faraday cage electrode conductor is fully isolated from Faraday cage electrode conductors of the other array elements, wherein for M array elements there are M corresponding Faraday cage electrode conductors, and the M corresponding Faraday cage electrode conductors are isolated from each other, d) the grounded state of the Faraday cage electrode suppresses an effect of the substrate on a bottom electrode and reduces electrical crosstalk between neighboring array elements, e) the floating state of the Faraday cage electrode reduces a parasitic capacitance of the array element and a cross-coupling capacitance of the array element and the neighboring array element, f) the CMUT array is operable such that, during a transmit operation of the array element, the Faraday cage electrode conductor is in the grounded state, and during a receive operation of the array element, the Faraday cage electrode conductor is in the floating state, g) in the floating state, the Faraday cage electrode conductor accumulates charges in time due to a leakage current through the second insulation dielectric layer as a result of an applied voltage on the bottom electrode.

3. The CMUT array according to claim 1, wherein a) each of the at least two array elements is independently operable, based on whether the array element is operating in the transmit operation or the receive operation, with the unique Faraday cage electrode conductor of the each of the at least two array elements in the grounded state or the floating state regardless of the operational status of the other array elements, b) CMUT cells are operable in conventional, collapse, resistive-collapse and collapse-snapback modes.

4. The CMUT array according to claim 1, wherein the lightning rod structure comprises a) a movable grounded conductive diamond membrane separated by a gap from the fixed conductive diamond emitter, the movable grounded conductive diamond membrane is electrically connected to ground, b) the gap is vacuum-sealed or air-filled, wherein pressure in the cavity ranges from atmospheric pressure down to low pressure, c) a movable membrane, wherein the movable membrane is configured to deflect towards the conductive diamond emitter due to electrostatic force to close the gap to facilitate safe intermittent discharging through the conductive diamond emitter, the lightning rod structure operating as a charge-controlled capacitive device, d) the conductive diamond emitter having a low work function, a high enhancement factor, and electrical conductivity to enable stable discharging at high emission current density, e) an insulator layer on a periphery of the conductive diamond membrane providing mechanical support.

5. A method for microfabrication of the CMUT array according to claim 1, comprising;

a) performing patterning of a conductive device layer of a silicon-on-insulator (SOI) wafer to construct a Faraday cage of the array element with lithography and deep reactive ion etching (DRIE), b) performing thermal growth of silicon dioxide to provide electrical isolation of Faraday Cage from the other electrodes of the array element, c) performing polysilicon layer deposition, comprising the operation of doping and patterning with lithography and reactive ion etching (RIE) to construct a bottom electrode, d) performing low temperature oxide (LTO) layer deposition, comprising the operation of patterning with lithography and RIE to construct an anchor of the CMUT cell, e) performing patterning of the thermal grown silicon dioxide with lithography and RIE to provide electrical contact between the Faraday cage and the conductive diamond emitter, f) performing first boron-doped nanocrystalline diamond (BNCD) layer deposition, comprising the operation of patterning with lithography and RIE (using LTO as hard mask) to form the conductive diamond emitters, g) performing high temperature oxide (HTO) deposition, comprising the operation of patterning with lithography and RIE to form the first insulation dielectric layer above the bottom electrode, h) performing polysilicon layer deposition, comprising the operation of doping and patterning with lithography and RIE as a sacrificial layer in an active area of the CMUT cell, i) performing polysilicon layer deposition, comprising the operation of doping and patterning with lithography and RIE as a sacrificial layer to define etch channels and to construct dimple spacing, j) performing second BNCD layer deposition, comprising the operation of patterning with lithography and RIE using LTO as hard mask to construct the membrane having dimples of the CMUT cell and the membrane having dimples of the lightning rod structure and to define an etch via for sacrificial etch of polysilicon, an opening for metal pad connections, and a separation zone between membrane of the CMUT cell and membrane of a lightning rod, k) performing sacrificial etching of polysilicon in XeF$_2$ plasma, l) Performing LTO layer deposition to provide sealing of the CMUT cell cavity and lightning rod cavity, m) performing patterning of silicon dioxide with lithography and buffered hydrofluoric acid (BHF) etching for removal of unnecessary silicon dioxide, n) performing metallization and patterning of electrode pads with metal lift-off technique.

* * * * *